(12) United States Patent
Makower et al.

(10) Patent No.: US 9,161,749 B2
(45) Date of Patent: Oct. 20, 2015

(54) METHOD AND APPARATUS FOR TREATING SEXUAL DYSFUNCTION

(75) Inventors: Joshua Makower, Los Altos, CA (US); Thedoore C. Lamson, Pleasanton, CA (US); Joseph Catanese, III, San Leandro, CA (US)

(73) Assignee: NeoTract, Inc., Pleasanton, CA (US)

( * ) Notice: Subject to any disclaimer, the term of this patent is extended or adjusted under 35 U.S.C. 154(b) by 468 days.

(21) Appl. No.: 13/445,184

(22) Filed: Apr. 12, 2012

(65) Prior Publication Data

US 2012/0265006 A1    Oct. 18, 2012

Related U.S. Application Data

(60) Provisional application No. 61/475,516, filed on Apr. 14, 2011.

(51) Int. Cl.
A61B 17/04 (2006.01)
A61B 17/42 (2006.01)
A61B 17/06 (2006.01)

(52) U.S. Cl.
CPC ......... *A61B 17/0401* (2013.01); *A61B 17/0482* (2013.01); *A61B 17/42* (2013.01); *A61B 2017/0419* (2013.01); *A61B 2017/06052* (2013.01)

(58) Field of Classification Search
USPC ........................................ 600/38–41; 128/898
See application file for complete search history.

(56) References Cited

U.S. PATENT DOCUMENTS

| | | |
|---|---|---|
| 659,422 A | 10/1900 | Shidler |
| 780,392 A | 1/1905 | Wanamaker |
| 789,467 A | 5/1905 | West |
| 2,485,531 A | 10/1949 | William |
| 2,579,192 A | 12/1951 | Kohl |
| 2,646,298 A | 7/1953 | Leary |
| 2,697,624 A | 12/1954 | Thomas |
| 2,734,299 A | 2/1956 | Masson |
| 2,825,592 A | 3/1958 | McKenzie |
| 3,326,586 A | 6/1967 | Frost |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs |
| 3,713,680 A | 1/1973 | Pagano |
| 3,716,058 A | 2/1973 | Tanner |
| 3,756,638 A | 9/1973 | Stockberger |

(Continued)

FOREIGN PATENT DOCUMENTS

| | | |
|---|---|---|
| DE | 10159470 A1 | 6/2003 |
| EP | 0246836 | 12/1991 |

(Continued)

OTHER PUBLICATIONS

Bachavora, O.A., "The Effect of Rhodiolae Rosea Extract on Incidence Rate of Superficial Bladder Carcinoma Relapses", Kozin, (Jan. 1, 1995), 3 pgs.

(Continued)

*Primary Examiner* — Samuel Gilbert

(57) ABSTRACT

A system and associated method for manipulating tissues and anatomical or other structures in medical applications for the purpose of treating sexual dysfunction. In one aspect, the system includes a delivery device configured to deploy and implant anchor devices for such purposes.

12 Claims, 45 Drawing Sheets

(56) References Cited

U.S. PATENT DOCUMENTS

| | | |
|---|---|---|
| 3,873,140 A | 3/1975 | Bloch |
| 3,875,648 A | 4/1975 | Bone |
| 3,886,933 A | 6/1975 | Mori |
| 3,931,667 A | 1/1976 | Merser |
| 3,976,079 A | 8/1976 | Samuels |
| 4,006,747 A | 2/1977 | Kronenthal |
| 4,137,920 A | 2/1979 | Bonnet |
| 4,164,225 A | 8/1979 | Johnson |
| 4,210,148 A | 7/1980 | Stivala |
| 4,235,238 A | 11/1980 | Ogiu |
| 4,291,698 A | 9/1981 | Fuchs |
| 4,409,974 A | 10/1983 | Freedland |
| 4,419,094 A | 12/1983 | Patel |
| 4,493,323 A | 1/1985 | Albright |
| 4,513,746 A | 4/1985 | Aranyi |
| 4,621,640 A | 11/1986 | Mulhollan |
| 4,655,771 A | 4/1987 | Wallsten |
| 4,657,461 A | 4/1987 | Smith |
| 4,669,473 A | 6/1987 | Richards |
| 4,705,040 A | 11/1987 | Mueller |
| 4,714,281 A | 12/1987 | Peck |
| 4,738,255 A | 4/1988 | Goble |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,899,743 A | 2/1990 | Nicholson |
| 4,926,860 A | 5/1990 | Stice |
| 4,946,468 A | 8/1990 | Li |
| 4,955,913 A | 9/1990 | Robinson |
| 4,968,315 A | 11/1990 | Gatturna |
| 5,002,550 A | 3/1991 | Li |
| 5,019,032 A | 5/1991 | Robertson |
| 5,041,129 A | 8/1991 | Hayhurst |
| 5,046,513 A | 9/1991 | Gatturna |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen |
| 5,100,421 A | 3/1992 | Christoudias |
| 5,123,914 A | 6/1992 | Cope |
| 5,127,393 A | 7/1992 | McFarlin |
| 5,129,912 A | 7/1992 | Noda |
| 5,133,713 A | 7/1992 | Huang |
| 5,159,925 A | 11/1992 | Neuwirth |
| 5,160,339 A | 11/1992 | Chen |
| 5,192,303 A | 3/1993 | Gatturna |
| 5,203,787 A | 4/1993 | Noblitt |
| 5,207,672 A | 5/1993 | Roth |
| 5,217,470 A | 6/1993 | Weston |
| 5,217,486 A | 6/1993 | Rice |
| 5,234,454 A | 8/1993 | Bangs |
| 5,236,445 A | 8/1993 | Hayhurst |
| 5,237,984 A | 8/1993 | Williams |
| 5,258,015 A | 11/1993 | Li |
| 5,267,960 A | 12/1993 | Hayman |
| 5,269,802 A | 12/1993 | Garber |
| 5,269,809 A | 12/1993 | Hayhurst |
| 5,300,099 A | 4/1994 | Rudie |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler |
| 5,354,271 A | 10/1994 | Voda |
| 5,358,511 A | 10/1994 | Gatturna |
| 5,364,408 A | 11/1994 | Gordon |
| 5,366,490 A | 11/1994 | Edwards |
| 5,368,599 A | 11/1994 | Hirsch |
| 5,370,646 A | 12/1994 | Reese |
| 5,380,334 A | 1/1995 | Torrie |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash |
| 5,417,691 A | 5/1995 | Hayhurst |
| 5,435,805 A | 7/1995 | Edwards |
| 5,470,337 A | 11/1995 | Moss |
| 5,472,446 A | 12/1995 | de la Torre |
| 5,480,406 A | 1/1996 | Nolan |
| 5,499,994 A | 3/1996 | Tihon |
| 5,501,690 A | 3/1996 | Measamer |
| 5,507,754 A | 4/1996 | Green |
| 5,522,846 A | 6/1996 | Bonutti |
| 5,531,763 A | 7/1996 | Mastri |
| 5,536,240 A | 7/1996 | Edwards |
| 5,540,704 A | 7/1996 | Gordon |
| 5,545,171 A | 8/1996 | Sharkey |
| 5,545,178 A | 8/1996 | Kensey |
| 5,550,172 A | 8/1996 | Regula |
| 5,554,162 A | 9/1996 | DeLange |
| 5,554,171 A | 9/1996 | Gatturna |
| 5,562,689 A | 10/1996 | Green |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon |
| 5,591,177 A | 1/1997 | Lehrer |
| 5,593,421 A | 1/1997 | Bauer |
| 5,611,515 A | 3/1997 | Benderev |
| 5,626,614 A | 5/1997 | Hart |
| 5,630,824 A | 5/1997 | Hart |
| 5,647,836 A | 7/1997 | Blake |
| 5,665,109 A | 9/1997 | Yoon |
| 5,667,488 A | 9/1997 | Lundquist |
| 5,669,917 A | 9/1997 | Sauer |
| 5,690,649 A | 11/1997 | Li |
| 5,690,677 A | 11/1997 | Schmieding |
| 5,697,950 A | 12/1997 | Fucci |
| 5,707,386 A * | 1/1998 | Schnepp-Pesch et al. .... 606/194 |
| 5,707,394 A | 1/1998 | Miller |
| 5,716,368 A | 2/1998 | de la Torre |
| 5,718,717 A | 2/1998 | Bonutti |
| 5,725,556 A | 3/1998 | Moser |
| 5,725,557 A | 3/1998 | Gatturna |
| 5,733,306 A | 3/1998 | Bonutti |
| 5,741,276 A | 4/1998 | Poloyko |
| 5,746,753 A | 5/1998 | Sullivan |
| 5,749,846 A | 5/1998 | Edwards |
| 5,749,889 A | 5/1998 | Bacich |
| 5,752,963 A | 5/1998 | Allard |
| 5,782,862 A | 7/1998 | Bonutti |
| 5,782,864 A | 7/1998 | Lizardi |
| 5,800,445 A | 9/1998 | Ratcliff |
| 5,807,403 A | 9/1998 | Beyar |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus |
| 5,830,221 A | 11/1998 | Stein |
| 5,845,645 A | 12/1998 | Bonutti |
| 5,846,254 A | 12/1998 | Schulze |
| 5,861,002 A | 1/1999 | Desai |
| 5,868,762 A | 2/1999 | Cragg |
| 5,873,891 A | 2/1999 | Sohn |
| 5,879,357 A | 3/1999 | Heaton |
| 5,897,574 A | 4/1999 | Bonutti |
| 5,899,911 A | 5/1999 | Carter |
| 5,899,921 A | 5/1999 | Caspari |
| 5,904,679 A | 5/1999 | Clayman |
| 5,904,696 A | 5/1999 | Rosenman |
| 5,908,428 A | 6/1999 | Scirica |
| 5,908,447 A | 6/1999 | Schroeppel |
| 5,919,198 A | 7/1999 | Graves |
| 5,919,202 A | 7/1999 | Yoon |
| 5,921,982 A | 7/1999 | Lesh |
| 5,921,986 A | 7/1999 | Bonutti |
| 5,928,252 A | 7/1999 | Steadman |
| 5,931,844 A | 8/1999 | Thompson |
| 5,944,739 A | 8/1999 | Zlock |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |

(56) References Cited

U.S. PATENT DOCUMENTS

| | | |
|---|---|---|
| 5,964,732 A | 10/1999 | Willard |
| 5,971,447 A | 10/1999 | Steck |
| 6,010,514 A | 1/2000 | Burney |
| 6,011,525 A | 1/2000 | Piole |
| 6,015,428 A | 1/2000 | Pagedas |
| 6,030,393 A | 2/2000 | Corlew |
| 6,033,413 A | 3/2000 | Mikus |
| 6,033,430 A | 3/2000 | Bonutti |
| 6,036,701 A | 3/2000 | Rosenman |
| 6,048,351 A | 4/2000 | Gordon |
| 6,053,908 A | 4/2000 | Crainich |
| 6,056,722 A | 5/2000 | Jayaraman |
| 6,056,772 A | 5/2000 | Bonutti |
| 6,066,160 A | 5/2000 | Colvin |
| 6,068,648 A | 5/2000 | Cole |
| 6,080,167 A | 6/2000 | Lyell |
| 6,086,608 A | 7/2000 | Ek |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li |
| 6,120,539 A | 9/2000 | Eldridge |
| 6,132,438 A | 10/2000 | Fleischman |
| 6,139,555 A | 10/2000 | Hart |
| RE36,974 E | 11/2000 | Bonutti |
| 6,143,006 A | 11/2000 | Chan |
| 6,152,935 A | 11/2000 | Kammerer |
| 6,156,044 A | 12/2000 | Kammerer |
| 6,159,207 A | 12/2000 | Yoon |
| 6,159,234 A | 12/2000 | Bonutti |
| 6,200,329 B1 | 3/2001 | Fung |
| 6,206,895 B1 | 3/2001 | Levinson |
| 6,206,907 B1 | 3/2001 | Marino |
| 6,228,096 B1 | 5/2001 | Marchand |
| 6,258,124 B1 | 7/2001 | Darois |
| 6,261,302 B1 | 7/2001 | Voegele |
| 6,270,530 B1 | 8/2001 | Eldridge |
| 6,280,460 B1 | 8/2001 | Bolduc |
| 6,287,317 B1 | 9/2001 | Makower |
| 6,290,711 B1 | 9/2001 | Caspari |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff |
| 6,398,795 B1 | 6/2002 | McAlister |
| 6,425,900 B1 | 7/2002 | Knodel |
| 6,428,562 B2 | 8/2002 | Bonutti |
| 6,436,107 B1 | 8/2002 | Wang |
| 6,461,355 B2 | 10/2002 | Svejkovsky |
| 6,482,235 B1 | 11/2002 | Lambrecht |
| 6,488,691 B1 | 12/2002 | Carroll |
| 6,491,707 B2 | 12/2002 | Makower |
| 6,494,888 B1 | 12/2002 | Cruz et al. |
| 6,500,184 B1 | 12/2002 | Chan |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus |
| 6,527,702 B2 | 3/2003 | Whalen |
| 6,527,794 B1 | 3/2003 | McDevitt |
| 6,530,932 B1 | 3/2003 | Swayze |
| 6,533,796 B1 | 3/2003 | Sauer |
| 6,544,230 B1 | 4/2003 | Flaherty |
| 6,547,725 B1 | 4/2003 | Paolitto |
| 6,551,328 B2 | 4/2003 | Kortenbach |
| 6,551,333 B2 | 4/2003 | Kuhns |
| 6,565,578 B1 | 5/2003 | Peifer |
| 6,569,187 B1 | 5/2003 | Bonutti |
| 6,572,626 B1 | 6/2003 | Knodel |
| 6,572,635 B1 | 6/2003 | Bonutti |
| 6,572,653 B1 | 6/2003 | Simonson |
| 6,582,453 B1 | 6/2003 | Tran |
| 6,592,609 B1 | 7/2003 | Bonutti |
| 6,596,013 B2 | 7/2003 | Yang |
| 6,599,311 B1 | 7/2003 | Biggs |
| 6,626,913 B1 | 9/2003 | McKinnon |
| 6,626,916 B1 | 9/2003 | Yeung |
| 6,626,919 B1 | 9/2003 | Swanstrom |
| 6,629,534 B1 | 10/2003 | Dell et al. |
| 6,641,592 B1 | 11/2003 | Sauer |
| 6,656,182 B1 | 12/2003 | Hayhurst |
| 6,660,008 B1 | 12/2003 | Foerster |
| 6,660,023 B2 | 12/2003 | McDevitt |
| 6,663,589 B1 | 12/2003 | Halevy |
| 6,663,633 B1 | 12/2003 | Pierson |
| 6,663,639 B1 | 12/2003 | Laufer |
| 6,669,707 B1 * | 12/2003 | Swanstrom et al. .......... 606/153 |
| 6,699,263 B2 | 3/2004 | Cope |
| 6,702,846 B2 | 3/2004 | Mikus |
| 6,706,047 B2 | 3/2004 | Trout |
| 6,709,493 B2 | 3/2004 | DeGuiseppi |
| 6,715,804 B2 | 4/2004 | Beers |
| 6,719,709 B2 | 4/2004 | Whalen |
| 6,730,112 B2 | 5/2004 | Levinson |
| 6,736,823 B2 | 5/2004 | Darois |
| 6,736,854 B2 | 5/2004 | Vadurro |
| 6,740,098 B2 | 5/2004 | Abrams |
| 6,767,037 B2 | 7/2004 | Wenstrom |
| 6,770,076 B2 | 8/2004 | Foerster |
| 6,773,438 B1 | 8/2004 | Knodel |
| 6,773,441 B1 | 8/2004 | Laufer |
| 6,790,213 B2 | 9/2004 | Cherok |
| 6,802,846 B2 | 10/2004 | Hauschild |
| 6,821,282 B2 | 11/2004 | Perry |
| 6,821,285 B2 | 11/2004 | Laufer |
| 6,821,291 B2 | 11/2004 | Bolea |
| 6,835,200 B2 | 12/2004 | Laufer |
| 6,905,475 B2 | 6/2005 | Hauschild |
| 6,908,473 B2 | 6/2005 | Skiba |
| 6,921,361 B2 | 7/2005 | Suzuki |
| 6,926,732 B2 | 8/2005 | Derus |
| 6,951,565 B2 | 10/2005 | Keane |
| 6,986,775 B2 | 1/2006 | Morales |
| 6,986,784 B1 | 1/2006 | Weiser |
| 6,991,596 B2 | 1/2006 | Whalen |
| 6,991,647 B2 | 1/2006 | Jadhav |
| 6,997,940 B2 | 2/2006 | Bonutti |
| 7,001,327 B2 | 2/2006 | Whalen |
| 7,008,381 B2 | 3/2006 | Janssens |
| 7,011,688 B2 | 3/2006 | Gryska |
| 7,015,253 B2 | 3/2006 | Escandon |
| 7,041,111 B2 | 5/2006 | Chu |
| 7,048,698 B2 | 5/2006 | Whalen |
| 7,048,747 B2 | 5/2006 | Arcia |
| 7,060,077 B2 | 6/2006 | Gordon |
| 7,063,715 B2 | 6/2006 | Onuki |
| 7,081,126 B2 | 7/2006 | McDevitt |
| 7,083,638 B2 | 8/2006 | Foerster |
| 7,087,073 B2 | 8/2006 | Bonutti |
| 7,089,064 B2 | 8/2006 | Manker |
| 7,090,690 B2 | 8/2006 | Foerster |
| 7,093,601 B2 | 8/2006 | Manker |
| 7,105,004 B2 | 9/2006 | DiCesare |
| 7,108,655 B2 | 9/2006 | Whalen |
| 7,141,038 B2 | 11/2006 | Whalen |
| 7,153,314 B2 | 12/2006 | Laufer |
| 7,179,225 B2 | 2/2007 | Shluzas |
| 7,226,558 B2 | 6/2007 | Nieman |
| 7,232,448 B2 | 6/2007 | Battles |
| 7,255,675 B2 | 8/2007 | Gertner |
| 7,288,063 B2 | 10/2007 | Petros |
| 7,303,108 B2 | 12/2007 | Shelton |
| 7,320,701 B2 | 1/2008 | Haut |
| 7,322,974 B2 | 1/2008 | Swoyer |
| 7,326,221 B2 | 2/2008 | Sakamoto |
| 7,334,822 B1 | 2/2008 | Hines |
| 7,340,300 B2 | 3/2008 | Christopherson |
| 7,399,304 B2 | 7/2008 | Gambale |
| 7,402,166 B2 | 7/2008 | Feigl |
| 7,416,554 B2 | 8/2008 | Lam |
| 7,417,175 B2 | 8/2008 | Oda |
| 7,481,771 B2 | 1/2009 | Fonseca |
| 7,553,317 B2 | 6/2009 | Weisenburgh |
| 7,608,108 B2 | 10/2009 | Bhatnagar |

(56) References Cited

U.S. PATENT DOCUMENTS

| | | | |
|---|---|---|---|
| 7,645,286 B2* | 1/2010 | Catanese et al. | 606/151 |
| 7,658,311 B2 | 2/2010 | Boudreaux | |
| 7,674,275 B2 | 3/2010 | Martin | |
| 7,695,494 B2 | 4/2010 | Foerster | |
| 7,704,261 B2 | 4/2010 | Sakamoto | |
| 7,727,248 B2 | 6/2010 | Smith | |
| 7,736,374 B2 | 6/2010 | Vaughan | |
| 7,758,594 B2* | 7/2010 | Lamson et al. | 606/139 |
| 7,766,923 B2* | 8/2010 | Catanese et al. | 606/139 |
| 7,780,682 B2* | 8/2010 | Catanese et al. | 606/139 |
| 7,896,891 B2 | 3/2011 | Catanese | |
| 7,905,889 B2 | 3/2011 | Catanese | |
| 7,914,542 B2* | 3/2011 | Lamson et al. | 606/139 |
| 7,951,158 B2* | 5/2011 | Catanese et al. | 606/151 |
| 8,007,503 B2* | 8/2011 | Catanese et al. | 606/151 |
| 8,043,309 B2 | 10/2011 | Catanese | |
| 8,157,815 B2 | 4/2012 | Catanese | |
| 8,216,254 B2 | 7/2012 | McLean | |
| 8,333,776 B2* | 12/2012 | Cheng et al. | 606/139 |
| 8,394,113 B2 | 3/2013 | Wei | |
| 8,425,535 B2* | 4/2013 | McLean et al. | 606/139 |
| 8,491,606 B2 | 7/2013 | Tong | |
| 8,628,542 B2 | 1/2014 | Merrick et al. | |
| 8,715,239 B2* | 5/2014 | Lamson et al. | 604/164.01 |
| 8,715,298 B2* | 5/2014 | Catanese et al. | 606/139 |
| 8,834,492 B2* | 9/2014 | McLean et al. | 606/139 |
| 2001/0041916 A1 | 11/2001 | Bonutti | |
| 2001/0044639 A1 | 11/2001 | Levinson | |
| 2002/0095154 A1 | 7/2002 | Atkinson | |
| 2002/0107540 A1 | 8/2002 | Whalen | |
| 2002/0128684 A1 | 9/2002 | Foerster | |
| 2002/0161382 A1 | 10/2002 | Neisz | |
| 2002/0193809 A1 | 12/2002 | Meade | |
| 2003/0109769 A1 | 6/2003 | Lowery | |
| 2003/0191497 A1 | 10/2003 | Cope | |
| 2003/0199860 A1 | 10/2003 | Loeb | |
| 2003/0204195 A1 | 10/2003 | Keane | |
| 2003/0236535 A1 | 12/2003 | Onuki | |
| 2004/0030217 A1 | 2/2004 | Yeung | |
| 2004/0043052 A1 | 3/2004 | Hunter | |
| 2004/0078046 A1 | 4/2004 | Barzell | |
| 2004/0122456 A1 | 6/2004 | Saadat | |
| 2004/0122474 A1 | 6/2004 | Gellman | |
| 2004/0147958 A1 | 7/2004 | Lam | |
| 2004/0193191 A1 | 9/2004 | Starksen | |
| 2004/0193194 A1 | 9/2004 | Laufer | |
| 2004/0194790 A1 | 10/2004 | Laufer | |
| 2004/0243178 A1 | 12/2004 | Haut | |
| 2004/0243179 A1 | 12/2004 | Foerster | |
| 2004/0243180 A1 | 12/2004 | Donnelly | |
| 2004/0243227 A1 | 12/2004 | Starksen | |
| 2004/0260345 A1 | 12/2004 | Foerster | |
| 2005/0010203 A1 | 1/2005 | Edwards | |
| 2005/0055087 A1 | 3/2005 | Starksen | |
| 2005/0065550 A1 | 3/2005 | Starksen | |
| 2005/0107811 A1 | 5/2005 | Starksen | |
| 2005/0107812 A1 | 5/2005 | Starksen | |
| 2005/0154401 A1 | 7/2005 | Weldon | |
| 2005/0165272 A1 | 7/2005 | Okada | |
| 2005/0177181 A1 | 8/2005 | Kagan | |
| 2005/0203344 A1 | 9/2005 | Orban | |
| 2005/0203550 A1 | 9/2005 | Laufer | |
| 2005/0216040 A1 | 9/2005 | Gertner | |
| 2005/0216078 A1 | 9/2005 | Starksen | |
| 2005/0251157 A1 | 11/2005 | Saadat | |
| 2005/0251177 A1 | 11/2005 | Saadat | |
| 2005/0267405 A1 | 12/2005 | Shah | |
| 2005/0273138 A1 | 12/2005 | To | |
| 2006/0025750 A1 | 2/2006 | Starksen | |
| 2006/0025784 A1 | 2/2006 | Starksen | |
| 2006/0025789 A1 | 2/2006 | Laufer | |
| 2006/0025819 A1 | 2/2006 | Nobis | |
| 2006/0026750 A1 | 2/2006 | Ballance | |
| 2006/0030884 A1 | 2/2006 | Yeung | |
| 2006/0058817 A1 | 3/2006 | Starksen | |
| 2006/0089646 A1 | 4/2006 | Bonutti | |
| 2006/0167477 A1 | 7/2006 | Arcia | |
| 2006/0241694 A1 | 10/2006 | Cerundolo | |
| 2006/0265042 A1 | 11/2006 | Catanese | |
| 2006/0276871 A1 | 12/2006 | Lamson | |
| 2006/0282081 A1 | 12/2006 | Fanton | |
| 2007/0049929 A1 | 3/2007 | Catanese | |
| 2007/0049970 A1 | 3/2007 | Belef | |
| 2007/0060931 A1 | 3/2007 | Hamilton | |
| 2007/0088362 A1 | 4/2007 | Bonutti | |
| 2007/0112385 A1 | 5/2007 | Conlon | |
| 2007/0142846 A1 | 6/2007 | Catanese | |
| 2007/0173888 A1 | 7/2007 | Gertner | |
| 2007/0260259 A1 | 11/2007 | Fanton | |
| 2008/0009888 A1 | 1/2008 | Ewers | |
| 2008/0021445 A1 | 1/2008 | Elmouelhi | |
| 2008/0033458 A1 | 2/2008 | McLean | |
| 2008/0033488 A1 | 2/2008 | Catanese | |
| 2008/0039874 A1 | 2/2008 | Catanese | |
| 2008/0039893 A1 | 2/2008 | McLean | |
| 2008/0039894 A1 | 2/2008 | Catanese | |
| 2008/0045978 A1 | 2/2008 | Kuhns | |
| 2008/0058710 A1 | 3/2008 | Wilk | |
| 2008/0065120 A1 | 3/2008 | Zannis | |
| 2008/0082113 A1 | 4/2008 | Bishop | |
| 2008/0086172 A1 | 4/2008 | Martin | |
| 2008/0091220 A1 | 4/2008 | Chu | |
| 2008/0091237 A1 | 4/2008 | Schwartz | |
| 2008/0119874 A1 | 5/2008 | Merves | |
| 2008/0154378 A1 | 6/2008 | Pelo | |
| 2008/0195145 A1 | 8/2008 | Bonutti | |
| 2008/0208220 A1 | 8/2008 | Shiono | |
| 2008/0228202 A1 | 9/2008 | Cropper | |
| 2008/0269737 A1 | 10/2008 | Elmouelhi | |
| 2009/0012537 A1 | 1/2009 | Green | |
| 2009/0112537 A1 | 4/2009 | Okumura | |
| 2010/0010631 A1 | 1/2010 | Otte | |
| 2010/0030262 A1 | 2/2010 | McLean | |
| 2010/0063542 A1 | 3/2010 | van Der Burg | |
| 2010/0114162 A1 | 5/2010 | Bojarski | |
| 2010/0286106 A1 | 11/2010 | Gat | |
| 2010/0286679 A1 | 11/2010 | Hoey | |
| 2011/0040312 A1 | 2/2011 | Lamson | |
| 2011/0046648 A1 | 2/2011 | Johnston | |
| 2011/0160747 A1 | 6/2011 | McLean | |
| 2011/0166564 A1 | 7/2011 | Merrick | |
| 2013/0096582 A1 | 4/2013 | Cheng | |
| 2013/0211431 A1 | 8/2013 | Wei | |
| 2013/0267772 A1 | 10/2013 | Catanese | |
| 2013/0274799 A1 | 10/2013 | Catanese | |
| 2013/0289342 A1 | 10/2013 | Tong | |
| 2013/0296889 A1 | 11/2013 | Tong | |
| 2013/0296935 A1 | 11/2013 | McLean | |

FOREIGN PATENT DOCUMENTS

| | | |
|---|---|---|
| EP | 0632999 A1 | 1/1995 |
| EP | 0464480 | 3/1995 |
| EP | 1082941 | 3/2005 |
| EP | 1016377 | 4/2006 |
| EP | 1006909 | 1/2007 |
| EP | 1852071 A2 | 11/2007 |
| EP | 1584295 | 2/2008 |
| EP | 1670361 | 4/2008 |
| EP | 1331886 | 12/2008 |
| EP | 1884198 | 3/2010 |
| EP | 1884199 | 1/2011 |
| EP | 1484023 | 5/2011 |
| FR | 2750031 A1 | 12/1997 |
| JP | 5836559 A | 3/1983 |
| JP | 09122134 A | 5/1997 |
| JP | 2004344427 A | 12/2004 |
| RU | 2062121 C1 | 10/1989 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | WO-8701270 | 3/1987 |
| WO | WO-9210142 | 6/1992 |

(56) References Cited

FOREIGN PATENT DOCUMENTS

| | | |
|---|---|---|
| WO | WO-9304727 | 3/1993 |
| WO | WO-9315664 | 8/1993 |
| WO | WO-0126588 | 4/2001 |
| WO | WO-0195818 | 12/2001 |
| WO | WO-0230335 | 4/2002 |
| WO | WO-0232321 | 4/2002 |
| WO | WO-0128432 | 8/2002 |
| WO | WO-03039334 | 5/2003 |
| WO | WO-03077772 | 9/2003 |
| WO | WO-0228289 | 11/2003 |
| WO | WO-2004017845 | 3/2004 |
| WO | WO-2004019787 | 3/2004 |
| WO | WO-2004019788 | 3/2004 |
| WO | WO-2004030569 | 4/2004 |
| WO | WO-2004103189 | 12/2004 |
| WO | WO-2005034738 | 4/2005 |
| WO | WO-2005065412 | 7/2005 |
| WO | WO-2005094447 | 10/2005 |
| WO | WO-2007053516 | 5/2007 |
| WO | WO-2007064906 | 6/2007 |
| WO | WO-2008006084 | 1/2008 |
| WO | WO-2008043044 | 4/2008 |
| WO | WO-2008043917 | 4/2008 |
| WO | WO-2009009617 | 1/2009 |
| WO | WO-2010011832 | 1/2010 |
| WO | WO-2012091954 | 7/2012 |

OTHER PUBLICATIONS

Berges, Richard, "Alternative Minimalinvasive Therapien Beim Benignen Prostatasyndrom", medizin, Jg, 104 heft 37, (Sep. 14, 2007), 12 pgs.

Borzhievski, "Tactics of the Surgical Treatment of Patients With Prostatic Adenoma and Acute Urinary Retention", Urologia Nefrol (Mosk), (1), (Jan. 1, 1987), 39-43.

European Application Serial No. 06770621, Supplementary European Search Report mailed Sep. 20, 2012, 3 pgs.

European Application Serial No. 06845991.6, Extended European Search Report mailed 0322-2013, 7 pgs.

European Application Serial No. 07840462.1, Extended European Search Report mailed May 29, 2012, 8 pgs.

European Application Serial No. 08729001.1, Extended European Search Report mailed Feb. 4, 2014, 6 pgs.

European Application Serial No. 08729001.1, Supplementary European Search Report mailed Feb. 21, 2014, 1 pg.

European Application Serial No. 11154962.1, European Search Report mailed May 19, 2011, 2 pgs.

European Application Serial No. 11154976, European Search Report mailed May 19, 2011, 2 pgs.

Hartung, Rudolf, "Instrumentelle Therapie der benegnen Prostatahyperplasie", Medizin, Deutsches Arzteblatt 97, Heft 15 (Apr. 14, 2000), 8 pgs.

Hofner, Klaus, "Operative Therapie des benignen Prostatasyndroms", Medizin, Dtsch Arztebl, 194(36), (Jan. 1, 2007), 6 pgs.

Hubmann R, "Geschichte der transurethralen Prostataeingriffe", Geschichte der Medizin, Urologe (B), 40, (Jan. 1, 2000), 152-160.

International Application Serial No. PCT/US06/19372, International Search Report mailed May 2, 2008, 1 pg.

International Application Serial No. PCT/US06/48962, International Search Report mailed Dec. 10, 2008, 2 pgs.

International Application Serial No. PCT/US2007/74019, International Search Report mailed on Jul. 25, 2008, 1 pg.

International Application Serial No. PCT/US2008/053001, International Search Report mailed Jun. 17, 2008, 3 pg.

International Application Serial No. PCT/US2008/069560, International Search Report mailed Sep. 8, 2008, 1 pg.

International Application Serial No. PCT/US2009/052271, International Search Report mailed Mar. 4, 2010, 6 pgs.

International Application Serial No. PCT/US2009/052275, International Search Report mailed Oct. 9, 2009, 4 pgs.

International Application Serial No. PCT/US2011/041200, International Search Report mailed Feb. 17, 2012, 5 pgs.

International Application Serial No. PCT/US2011/065348, International Search Report mailed Jun. 21, 2012, 5 pgs.

International Application Serial No. PCT/US2011/065358, International Search Report mailed Jun. 21, 2012, 9 pgs.

International Application Serial No. PCT/US2011/065377, International Search Report mailed Aug. 29, 2012, 11 pgs.

International Application Serial No. PCT/US2011065386, International Search Report mailed Jun. 28, 2012, 4 pgs.

Japanese Application Serial No. 2012-104915, Office Action mailed Mar. 17, 2014, 2 pgs.

Jonas, U, "Benigne Prostatahyperplasie", Der Urologe, 45, (Jan. 1, 2006), 134-144.

Kruck, S, "Aktuelle Therapiemoglichkeiten des Benignen Prostata-Syndroms", J Urol Urogynakol 209, 16 (1), (Jan. 1, 2009), 19-22.

Miyake, Osamu, "Medical Examination and Treatment For BPH", Pharma Med, vol. 22, No. 3, (Jan. 1, 2004), 97-103.

Reich, O, "Benignes Prostatasyndrom (BPS)", Der Urologe, A Issue, vol. 45, No. 6, (Jun. 1, 2006), 769-782.

Schauer, P, "New applications for endoscopy: the emerging field of endoluminal and transgastric bariatric surgery", Surgical Endoscopy, (Apr. 24, 2006), 10 pgs.

Sharp, Howard T, "Instruments and Methods—The 4-S Modification of the Roeder Knot: How to Tie It", Obstetrics & Gynecology, vol. 90, No. 6, (Dec. 1, 1997), 1004-1006.

Takashi, Daito, "Low-Invasive Treatment for BPH", Medico vol. 34, No. 10, 366-369.

Teruhisa, Osamu, "Urinary Dysfunction by Lower Urinary Tract Obstraction in Male", Pharma Medica, vol. 8, No. 8, (1990), 35-39.

Tomohiko, Koyanagi, "Surgery View of 21st Century", Urological Surgery, vol. 84, No. 1, (2001), 47-53.

Trapeznikov, "New Technologies in the Treatment of Benign Prostatic Hyperplasia", Urologia Nefrol(Mosk), (4), (Jul. 1, 1996), 41-47.

Yeung, Jeff, "Treating Urinary Stress Incontinence Without Incision with Endoscopic Suture Anchor & Approximating Device", Aleeva Medical, Inc, (Jan. 1, 2007), 31 pgs.

* cited by examiner

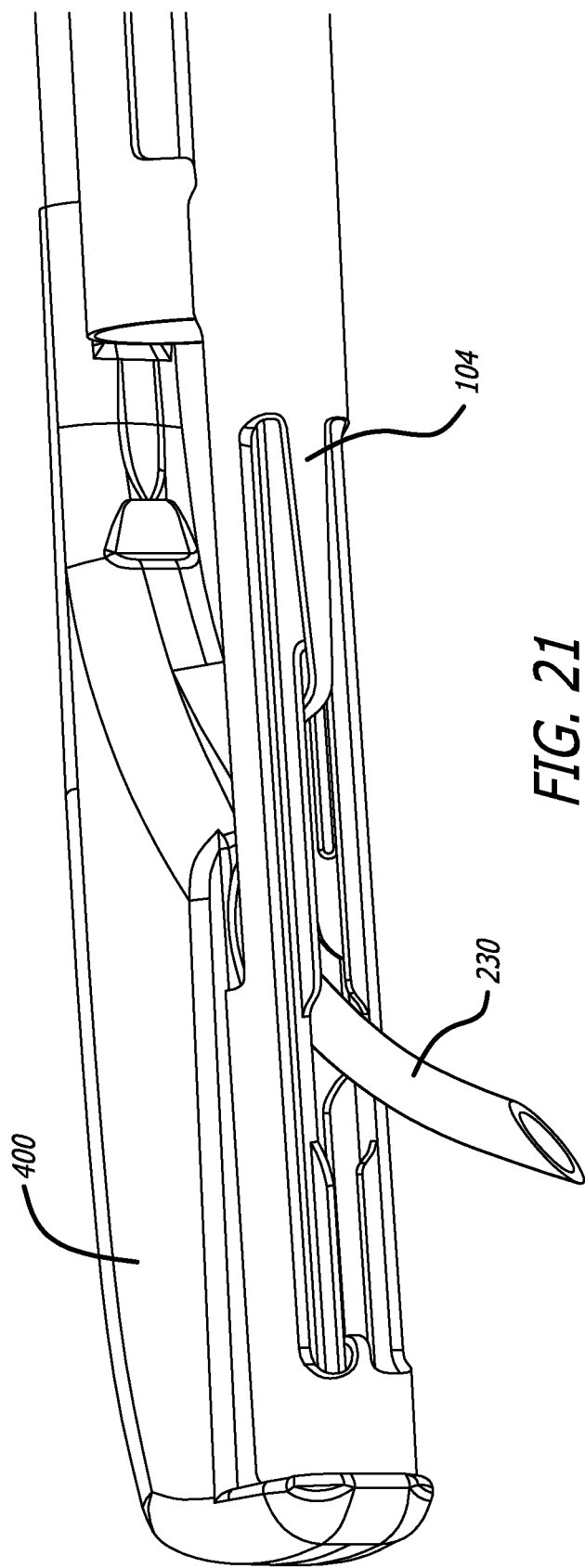

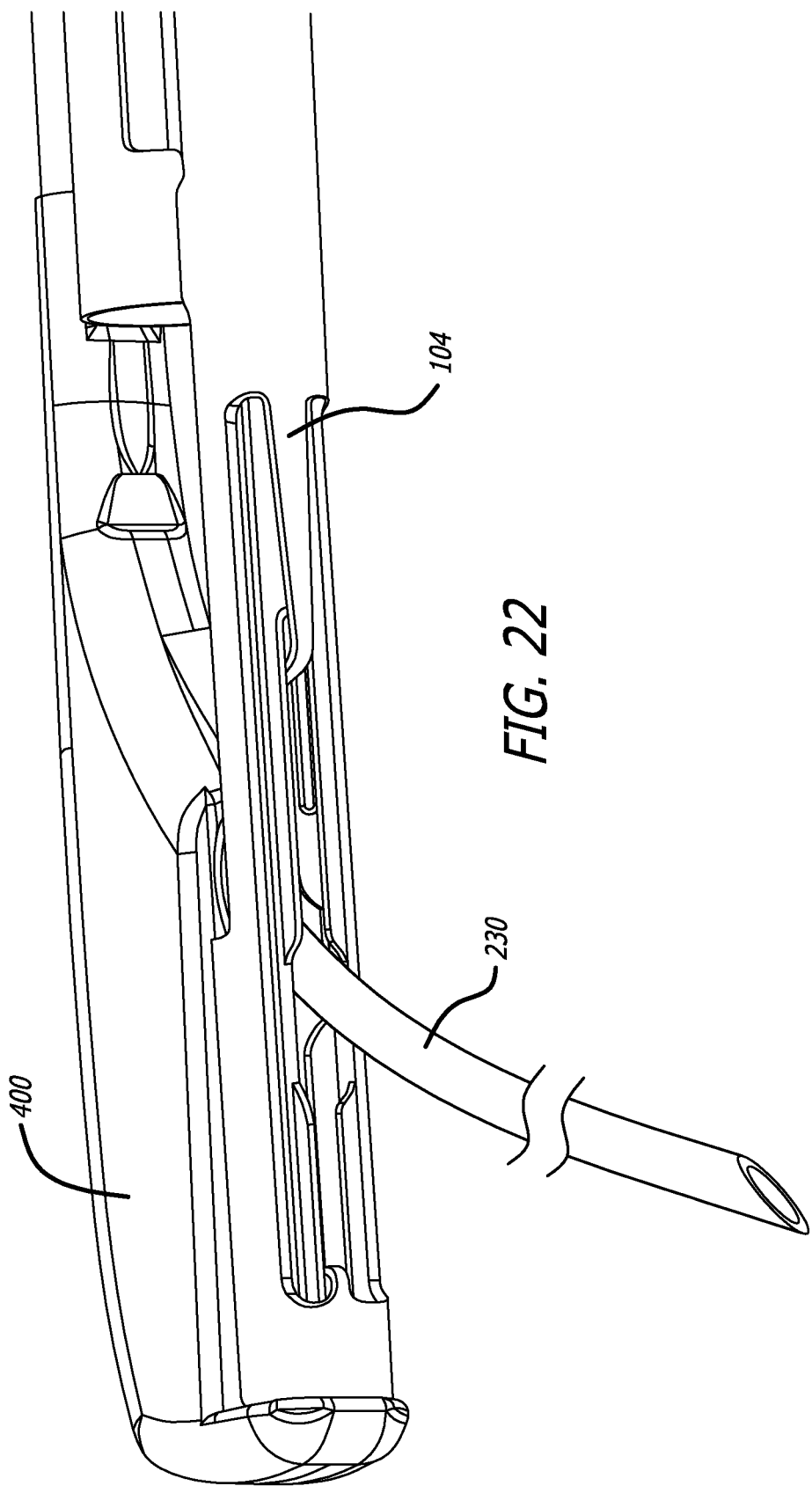

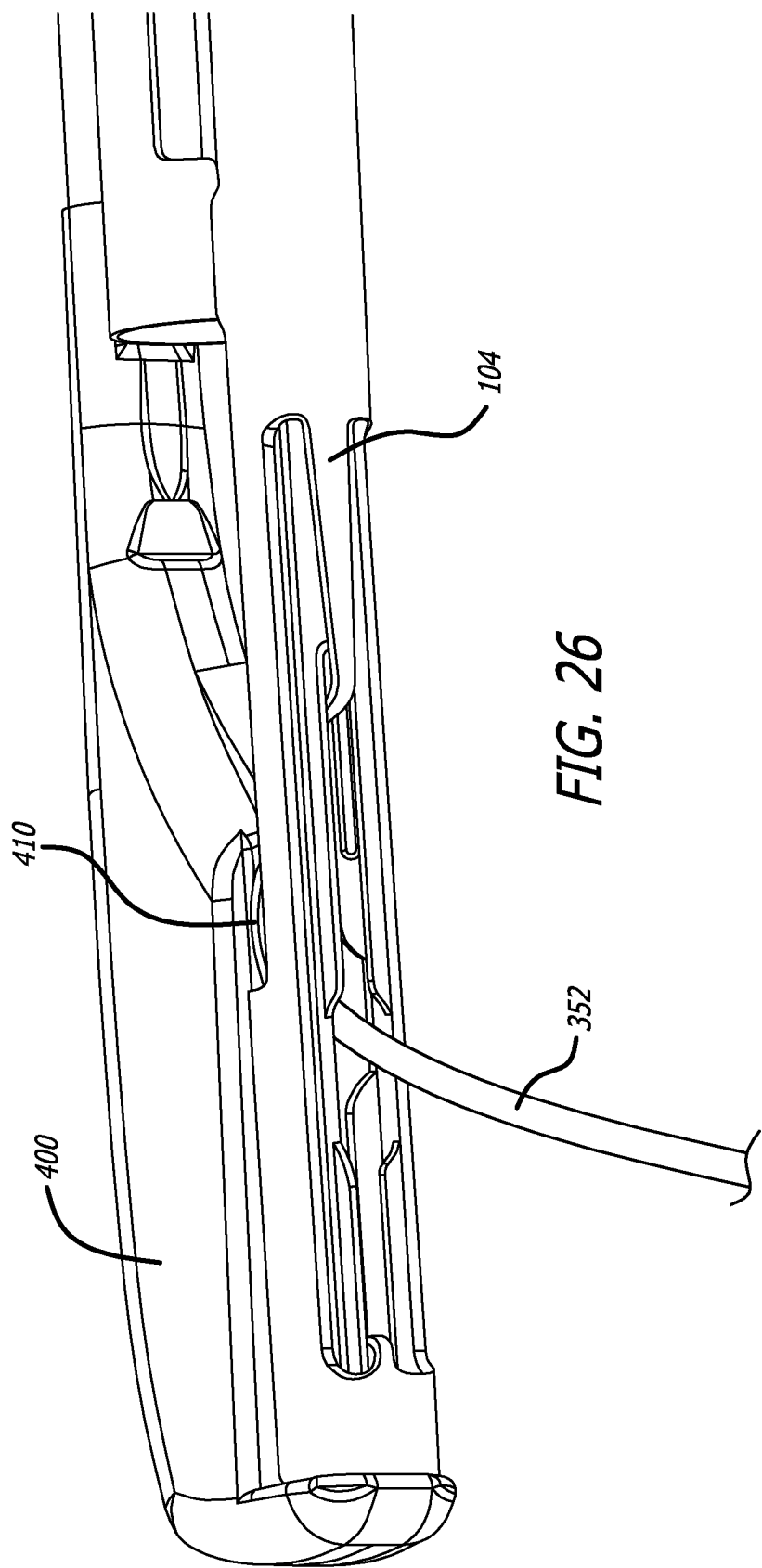

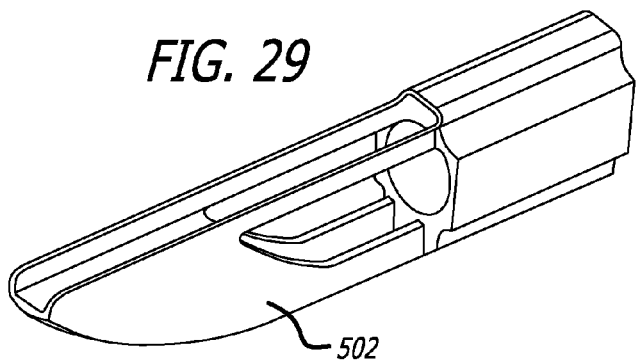
FIG. 29
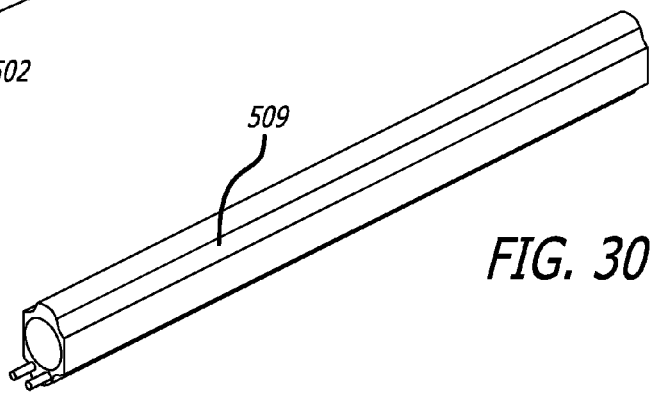
FIG. 30
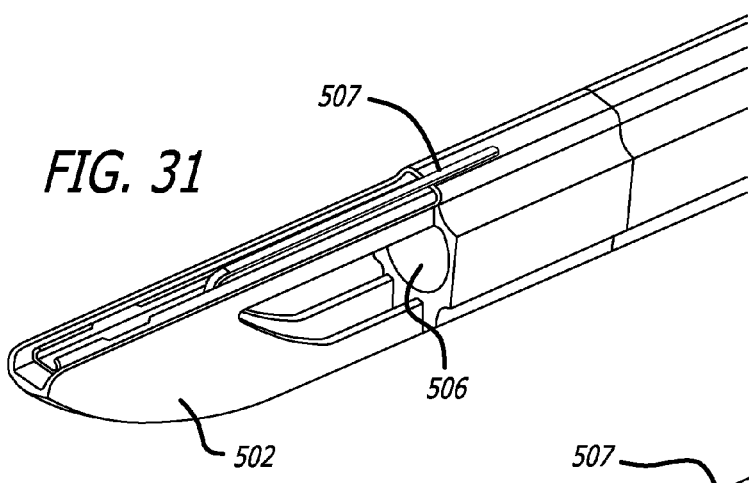
FIG. 31
FIG. 32

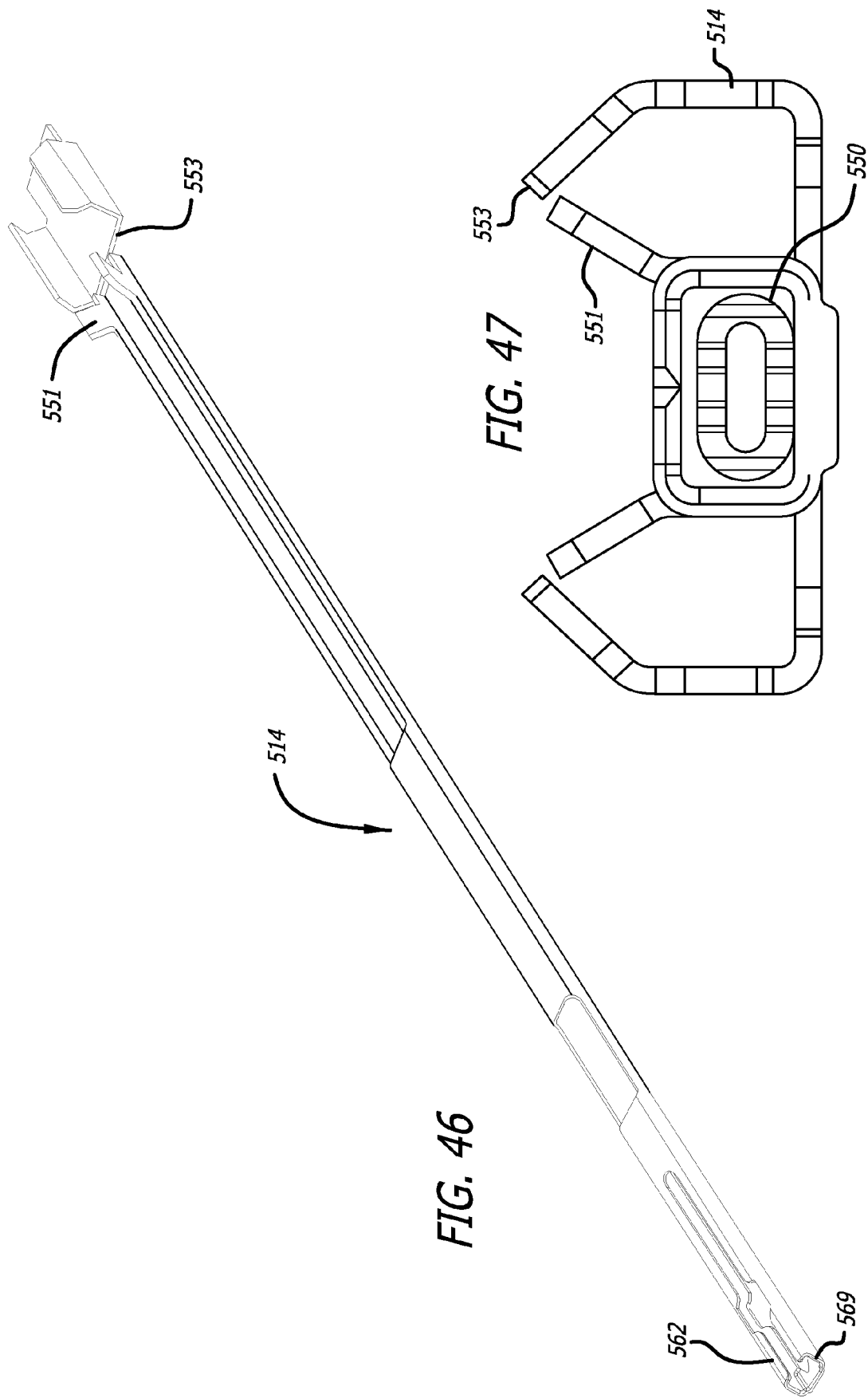

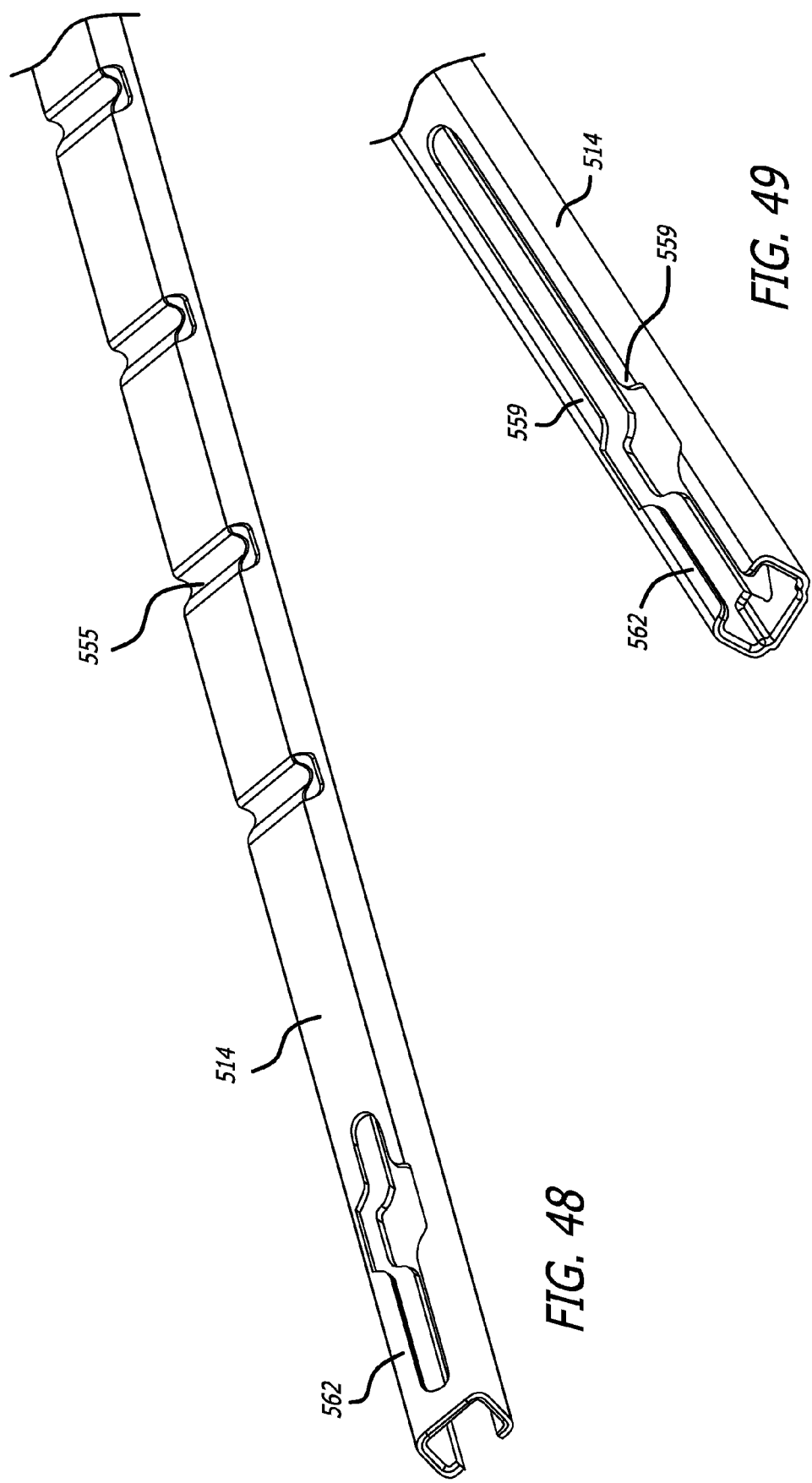

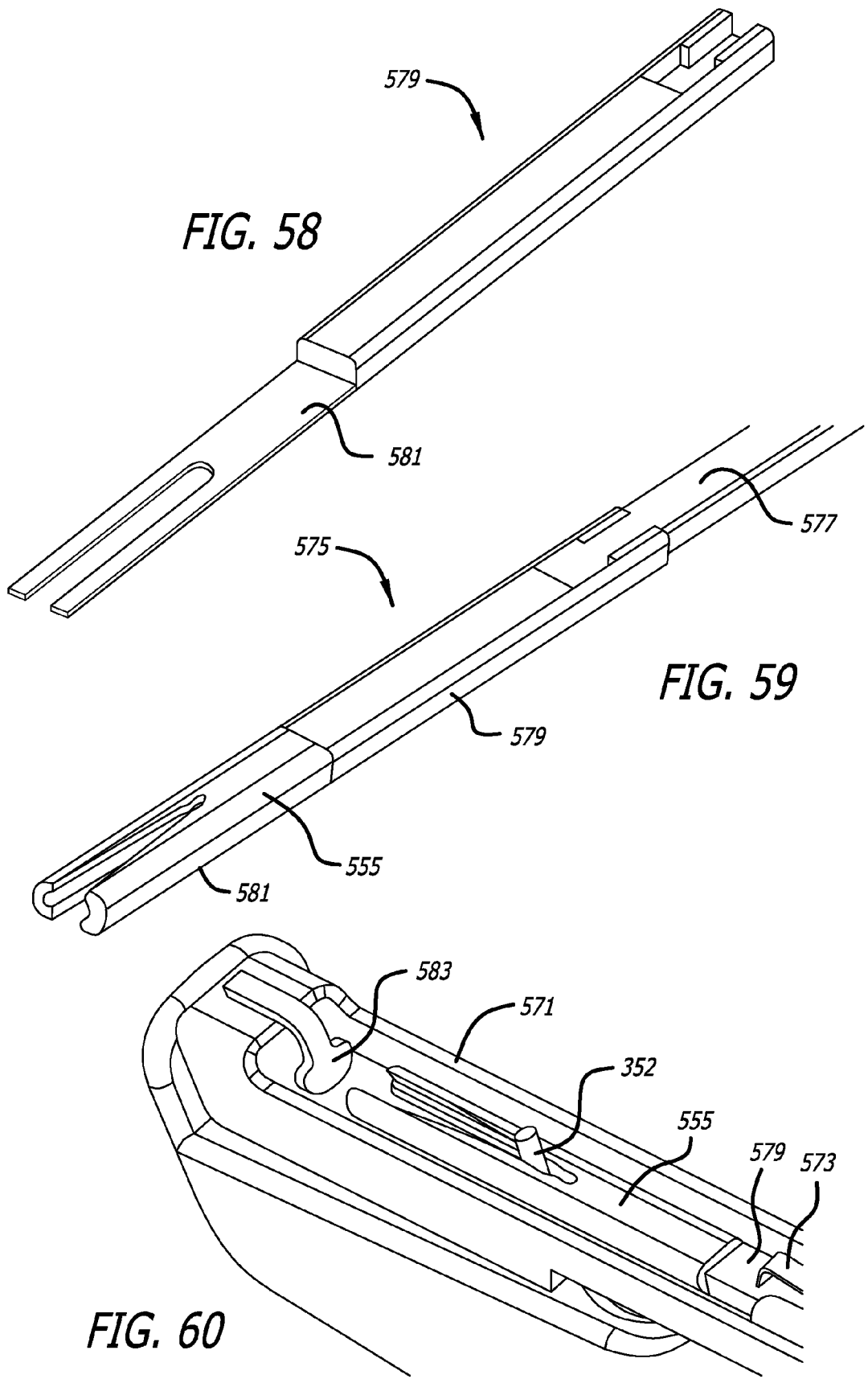

Mean erectile function score of IIEF

Mean score of MSHQ question 1 to

METHOD AND APPARATUS FOR TREATING SEXUAL DYSFUNCTION

FIELD OF THE INVENTION

The present invention relates generally to medical devices and methods, and more particularly to systems and associated methods for manipulating or retracting tissues and anatomical or other structures within the body of human or animal subjects for the purpose of treating sexual dysfunction.

BACKGROUND

Sexual dysfunction or sexual malfunction refers to a difficulty experienced by an individual or a couple during any stage of a normal sexual activity, including desire, arousal or orgasm. For men, erectile dysfunction or impotence is a sexual dysfunction characterized by the inability to develop or maintain an erection of the penis. There are various underlying causes, such as damage to the nervi erigentes which prevents or delays erection, or diabetes, which simply decreases blood flow to the tissue in the penis, many of which are medically reversible. There are many factors which may result in a person experiencing a sexual dysfunction. These may result from emotional or physical causes.

Sexual dysfunction may arise from emotional factors, including interpersonal or psychological problems. Interpersonal problems may arise from marital or relationship problems, or from a lack of trust and open communication between partners, and psychological problems may be the result of depression, sexual fears or guilt, past sexual trauma, sexual disorders, among others. Sexual dysfunction is especially common among people who have anxiety disorders. Ordinary anxiousness can obviously cause erectile dysfunction in men without psychiatric problems, but clinically diagnosable disorders such as panic disorder commonly cause avoidance of intercourse and premature ejaculation.

Physical damage can of course be a major contribution to sexual dysfunction. One leading physical cause of ED is continual or severe damage taken to the nervi erigentes. These nerves course beside the prostate arising from the sacral plexus and can be damaged in prostatic and colo-rectal surgeries.

In fact, the relationship between lower urinary tract symptoms (LUTS) and sexual dysfunction is well established and highly prevalent (Rosen R., Altwein J., Boyle P., et al. Lower urinary tract symptoms and male sexual dysfunction: the multinational survey of the aging male (MSAM-7). Eur Urol 2003; 44:637-49). Both disorders can impact quality of life and may share a common pathophysiology (McVary K. Lower urinary tract symptoms and sexual dysfunction: epidemiology and pathophysiology. BJU Int 2006; 97 (Suppl 2): 23-8, discussion 44-5). The efficacy of surgical treatments such as transurethral resection of the prostate (TURP) on LUTS due to benign prostatic hyperplasia (BPH) is well established. However, the effect of surgical treatment of bladder outlet obstruction (BOO) due to BPH on sexual function is not clear. Several authors have found that surgical treatment of BOO can impair sexual function (Muntener, M., Aellig, S., Kuettel R., Gehrlach C., Susler T., Strebel R. Sexual Function after Transurethral Resection of the Prostate (TURP): Results of an Independent Prospective Multicentre Assessment of Outcome. European Urology 52 (2007) 510-516; Briganti A., Naspro R., Gallina A., Salonia A., Vavassori I., Hurle R., Scattoni E., Rigatti P., Montorsi F. Impact on Sexual Function of Holmium Laser Enucleation Versus Transurethral Resection of the Prostate: Results of a Prosspective, 2-Center, Randomized Trial. The Journal of Urology. Vol. 175, May 2006: 1817-1821; Arai Y., Aoiki Y., Okubo K., Maeda H., Terada N., Matsuta Y., Maekawa S., Ogura K. Impact of Interventional Therapy for Benign Prostatic Hyperplasia on Quality of Life and Sexual Function: A Prospective Study. Journal of Urology. Vol. 164, 1206-1211 October 2000.) In contrast Brooks et al. found that sexual function can improve after surgical treatment (Brooks S., Donovan J., Peters T., Abramas P., Neal D. Sexual dysfunction in men after treatment for lower urinary tract symptoms: evidence from randomized controlled trial. BMJ. Vol. 324, May 2002).

There are a wide variety of situations in which it is desirable to lift, compress or otherwise reposition normal or aberrant tissues or anatomical structures (e.g., organs, ligaments, tendons, muscles, tumors, cysts, fat pads, etc.) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, etc.) and/or for cosmetic purposes (e.g., face lifts, breast lifts, brow lifts, etc.) and/or for research and development purposes (e.g., to create animal models that mimic various pathological conditions).

One particular example of a condition where it is desirable to lift, compress or otherwise remove a pathologically enlarged tissue is BPH. BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include BOO, weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

Although BPH is rarely life threatening, it can lead to numerous clinical conditions including urinary retention, renal insufficiency, recurrent urinary tract infection, incontinence, hematuria, bladder stones, and sexual dysfunction.

Surgical procedures for treating BPH symptoms include Transurethral Resection of Prostate (TURP), Transurethral Electrovaporization of Prostate (TVP), Transurethral Incision of the Prostate (TUIP), Laser Prostatectomy and Open Prostatectomy. Such invasive approaches, however, can negatively impact aspects of sexual function including erection and ejaculation.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

More recently, a minimally invasive surgical approach involving employing an anchor assembly to compress the prostate and open the urethra has been found to be effective in treating BPH. This tissue sparing procedure is designed to retract encroaching lobes of the prostate to improve LUTS and flow rate.

There remains a need for the development of approaches and methods that can be used for various procedures where it is desired to lift, compress, support or reposition tissues or organs within the body for the purpose of treating sexual dysfunction. In particular, there is a need for an apparatus and approaches for manipulating prostatic tissue, the urethra, and surrounding tissues to specifically improve LUTS and sexual dysfunction.

The present disclosure addresses these and other needs.

SUMMARY

Briefly and in general terms, the present disclosure is directed towards an apparatus and method for deploying an anchor assembly within a patient's body for the purpose of treating sexual dysfunction. The apparatus and anchor assembly are used to move and hold or compress tissue involved in one or more of urinary and sexual functions.

In one aspect, the disclosed method is intended to move and hold or compress tissue for the purpose of treating sexual dysfunction. Anatomy involved in male sexual function is accessed and a delivery device is provided and housed with structure for moving, manipulating or compressing tissue involved in sexual function. The tissue to be treated is identified and the treatment structure is implanted to improve sexual function. In one aspect, the treatment structure is an anchor assembly. In related aspects of the disclosure, approaches are taken to increase pelvic nitric oxide (NO). Additionally, or alternatively, the disclosed method of tissue manipulation or compression contemplates diminishing Rho-Kinose and thereby lessen calcium sensitivity and improve sexual function. The disclosed methods can also be performed to improve bladder outlet obstruction in a manner resulting in a sensory feedback through the automatic nervous system and subsequent decreases in sympathetic tone which may have a role in sexual function.

A system for treating sexual function is disclosed. In one particular aspect, the system includes a means for moving, manipulating or compressing prostatic, urinary tract or male reproductive tissue, and a delivery device housing the means for moving and holding or compressing tissue. The delivery device is also equipped with structure to accomplish permanently implanting the means for moving and holding or compressing tissue to treat sexual dysfunction. The means can be embodied in one or more anchor assemblies.

The apparatus of the present disclosure can also include various subassemblies which are mobilized via an actuator or other manually accessible structure. The operation of the subassemblies is coordinated and synchronized to ensure accurate and precise implantation of an anchor assembly to improve sexual function. In one embodiment, the delivery device is embodied in a tissue approximation assembly. The tool includes a case assembly enclosing an anchor delivery and assembly structure, a needle spool assembly and a suture spool assembly. Extending from the case assembly is a shaft assembly. Also, extending through the shaft assembly are a pusher assembly, a needle, and a cutter assembly. Operatively associated with the needle spool and suture spool assemblies are a needle actuator and a needle retraction actuator (e.g., a lever). An assembly actuator is operatively associated with the anchor assembly structure. Safety lock and lock-out structures are also operatively associated with the needle actuator and assembly actuator. Activation of the needle actuator accomplishes the advancement of a needle assembly and a first component of an anchor assembly attached to a connector member, to an interventional site. Activation of the needle retraction actuator withdraws the needle assembly leaving the first component of the anchor assembly at the interventional site. Thereafter, manipulation of the assembly actuator results in lockingly engaging a second anchor component with the connector member and cutting the connector member below the second anchor component.

In one particular aspect, the present invention is directed towards a delivery device which accomplishes the delivery of a first or distal anchor assembly component at a first location within a patient's body and the delivery of a second or proximal anchor assembly component at a second location within the patient so as to manipulate tissue in a manner to improve lower urinary tract symptoms (LUTS) and/or sexual function. The device also accomplishes imparting tension during delivery to a connector to hold it while attaching the proximal anchor in situ. The procedure can be viewed employing a scope inserted in the device. Also, the delivery device can be sized and shaped to be compatible inside a sheath in the range of 17 to 24F, preferably a 19F sheath or smaller.

Additionally, in a contemplated embodiment of an anchor delivery system, actuating a needle deploy actuator results in a needle being advanced within a patient to an interventional site. Activating a needle retraction lever accomplishes the withdrawal of the needle and deployment of a first anchor component of an anchor assembly at the interventional site. Depression of a second actuator facilitates the incorporation of a second component into the anchor assembly and its release at the interventional site. The anchor delivery system with its actuators and lever provide for a single-handed, one operator delivery of a distal anchor component and proximal anchor component spaced apart with a connector member between them. Various locking and sequencing mechanisms are provided for both operational as well as safety reasons.

The anchor assembly can be configured to accomplish approximating, retracting, lifting, compressing, supporting or repositioning tissue within the body of a human or animal subject that relate to LUTS and sexual function. Moreover, the apparatus configured to deploy the anchor assembly as well as the anchor assembly itself are configured to complement and cooperate with body anatomy.

In one embodiment, the anchor delivery device includes a handle assembly with an actuator attached thereto. The actuator is associated with a body of the handle assembly and is operatively attached to the needle and structure that advances the first anchor member. A second actuator is operatively associated with structure that accomplishes assembling the second anchor member to the connector member. Additionally, the handle assembly is equipped with structure that is configured in one contemplated embodiment, to effect the cutting of the connector member and deployment of the first anchor member, second anchor member, and connector at an interventional site.

Moreover, various alternative and complimentary methods of use are also contemplated. That is, in some applications of the invention, the invention is used to additionally or alternatively improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has a myriad of other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 21 is a perspective view in partial cross-section, depicting partial ejection of a needle assembly;

FIG. 22 is a perspective view in partial cross-section, depicting advancement of a needle assembly;

FIG. 26 is a perspective partial cross-sectional view, depicting withdrawal of a needle assembly leaving a connector element;

FIGS. 29-32 are perspective views, depicting components of one embodiment of a shaft assembly;

FIGS. 44-46 are perspective views, depicting features of one embodiment of a cutter assembly of the delivery device;

FIG. 47 is a cross-sectional view, depicting positioning of an anchor within the cutter assembly;

FIGS. 48-52 are various views, depicting further features of a cutter assembly;

FIGS. 58-60 are perspective views, depicting features of a pusher assembly;

DETAILED DESCRIPTION OF THE PREFERRED EMBODIMENTS

Figure 1:
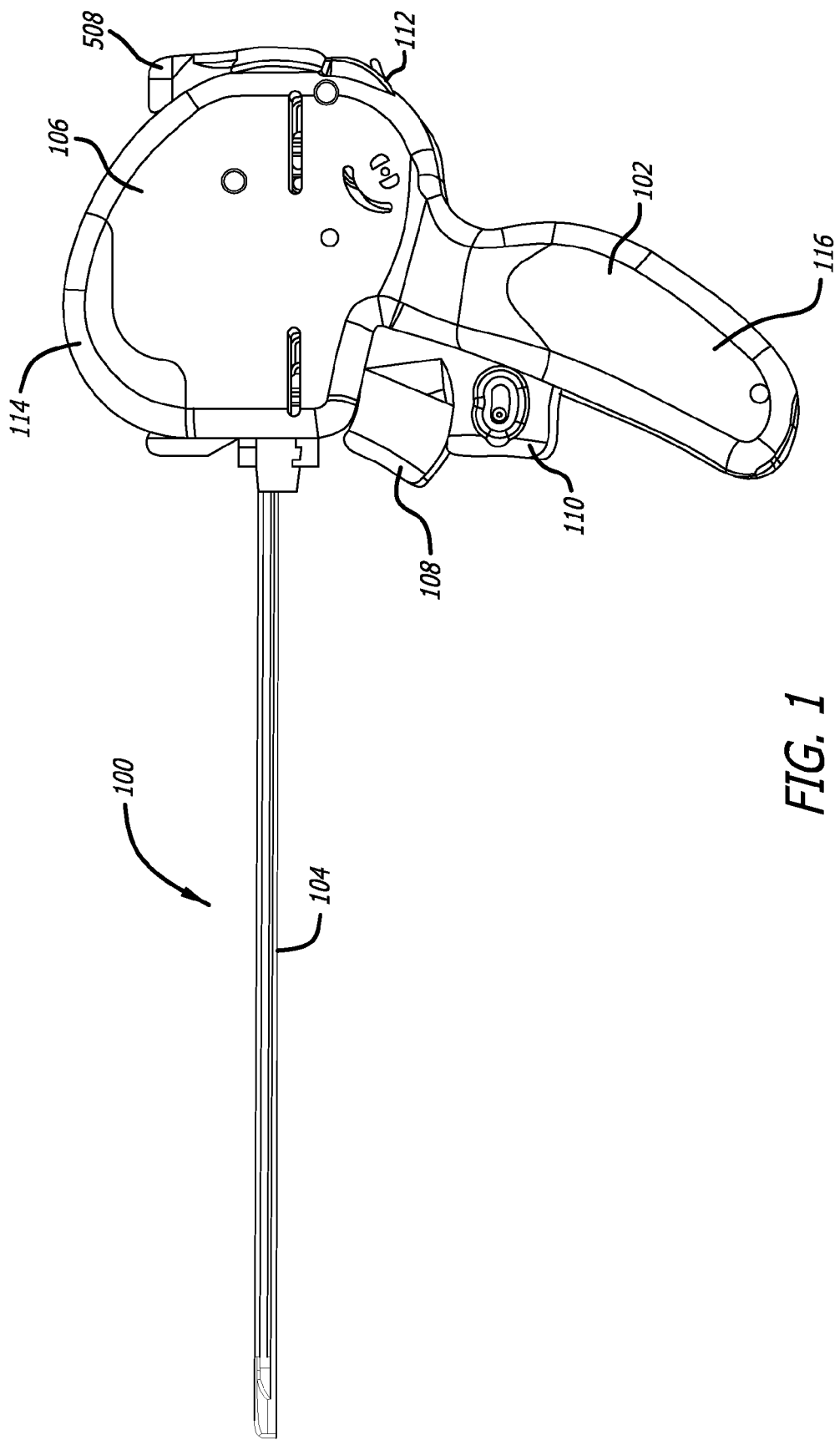
FIG. 1 is a left side view, depicting one embodiment of an anchor delivery system.

Turning now to the figures, which are provided by way of example and not limitation, the present disclosure is directed to a device configured to deliver an anchor assembly within a patient's body for the purpose of treating sexual dysfunction. The disclosed apparatus can be employed for retracting, lifting, compressing, approximating, supporting or repositioning tissues, organs, anatomical structures, grafts or other material found within a patient's body. Such tissue manipulation is intended to facilitate the treatment of diseases or disorders.

In an aspect of the present invention, one portion of an anchor assembly or implant is positioned and implanted against a first section of anatomy. A second portion of the anchor assembly or implant is then positioned and implanted adjacent a second section of anatomy for the purpose of retracting, lifting, compressing, approximating, supporting or repositioning the second section of anatomy with respect to the first section of anatomy as well as for the purpose of retracting, lifting, compressing, approximating, supporting or repositioning the first section of anatomy with respect to the second section of anatomy. It is also to be recognized that both a first and second portion of the anchor assembly can be configured to accomplish the desired retracting, lifting, compressing, approximating, supporting or repositioning of anatomy due to tension supplied during delivery via a connector assembly affixed to the first and second portions of the anchor assembly or implant.

As stated, the relationship between LUTS and sexual dysfunction has been established. In contrast to traditional surgical treatments, a tissue sparing procedure involving the disclosed anchor assembly that improves LUTS and flow rate is disclosed for treating sexual dysfunction. The method is designed to retract the encroaching lobes of the prostate by the use of small anchors placed through the prostate tissue so as to sit at the prostatic capsule. Each anchor positioned at the prostatic capsule is attached to a second anchor that is positioned against the urethral wall. The internal urethral anchor is then placed along a length of non-absorbable suture connecting the two anchors, so as to retract the hyperplasic tissue between the urethral wall and the prostatic capsule, thereby opening the prostatic urethra and relieving the obstruction. Because the urethral anchor is a small, thin-walled structure that is pushed into the urethral wall, no excess material (such as is found with cylindrical stents) protrudes from the urethral wall to act as a nidus for encrustation such that there is a positive impact on erectile and ejaculatory function.

Long established surgical treatments such as simple prostatectomy and TURP can cause retrograde ejaculation and negatively impact all aspects sexual function including erection and ejaculation. The disclosed minimally invasive treatment for LUTS that, in contrast to other surgical treatments is tissue sparing and involves anchors delivered transurethrally to separate the lobes of the prostate that encroach on the urethral lumen. By separating these lobes, the urethral lumen is expanded thus improving flow and IPSS.

It has been found that the disclosed approaches and method improves both erections and ejaculation. This improvement occurs shortly after surgery and appears to be durable for at least 6 months. Nitric oxide (NO) is known to be deficient in the prostate, bladder, and urethra in patients with BOO and the proposed method is intended to decrease NO. The proposed method is also intended to act through the Rho-kinase pathway. There can be increased Rho-kinase and thereby calcium sensitivity in the prostate smooth muscle in men with BPH and in the corpora cavernosa in men with ED. By improving LUTS, Rho-kinase can be diminished which would lessen calcium sensitivity and improve erections. An improved global satisfaction in health which is reflected in a nonspecific fashion can also favorably affect sexual outcomes. Finally, by improving BOO there is a sensory feedback through the autonomic nervous system and subsequent decrease in sympathetic tone which may improve erectile function.

Figure 2:
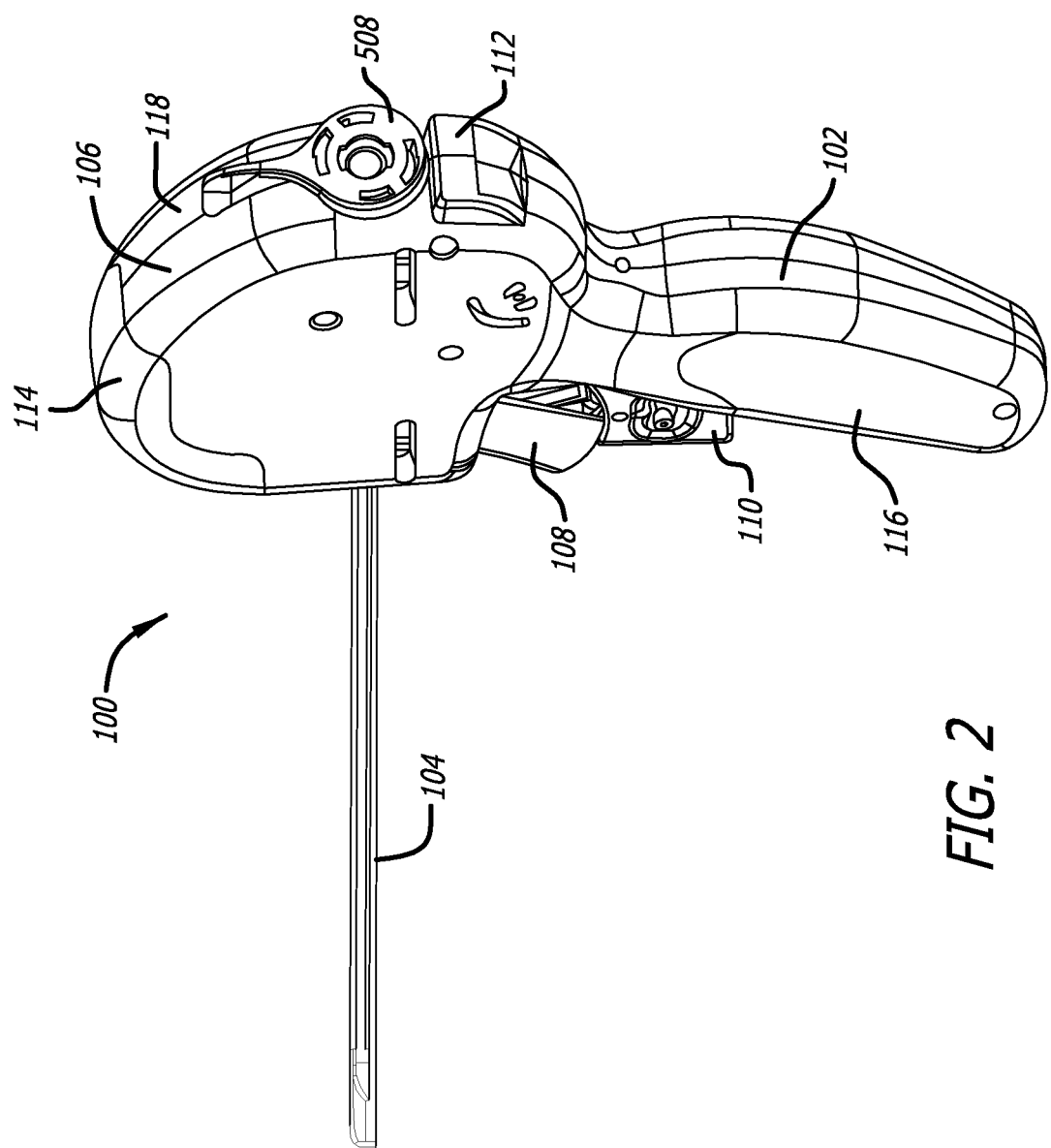
FIG. 2 is a perspective view, depicting the anchor delivery system of FIG. 1.
Figure 3:
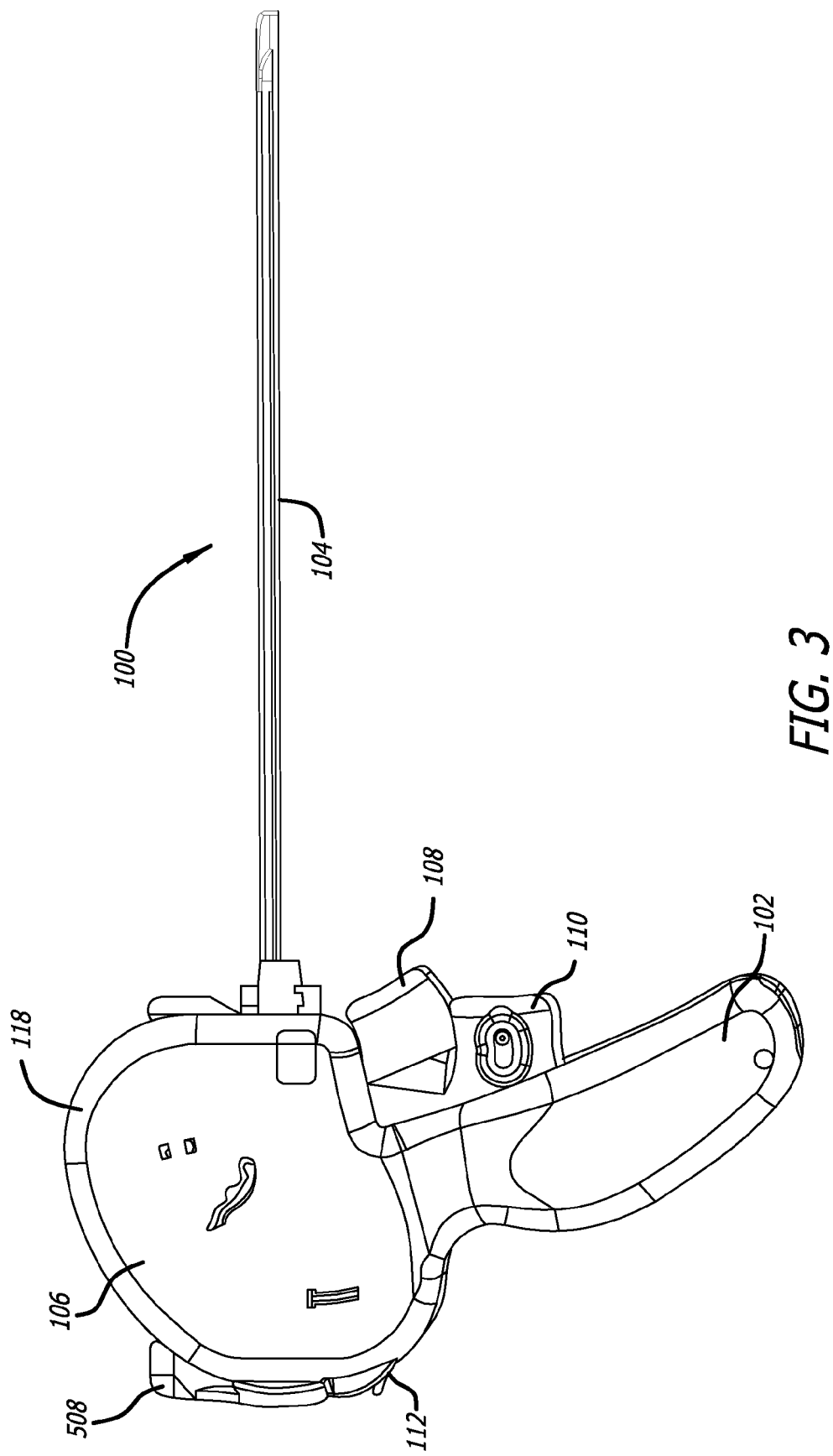
FIG. 3 is a right side view, depicting the anchor delivery system of FIG. 1.

Referring now to FIGS. 1-3, there is shown one embodiment of an anchor delivery device 100 which can be used to treat sexual dysfunction. This device is configured to include structure that is capable of both gaining access to an interventional site as well as assembling and implanting one or more anchor assemblies or implants within a patient's body. In one embodiment, the device 100 is configured to assemble and implant a single anchor assembly or implant. The device is further contemplated to be compatible for use with a 19F sheath. The device additionally includes structure configured to receive a conventional remote viewing device (e.g., an endoscope) so that the steps being performed at the interventional site can be observed.

Prior to use of the present device 100, a patient typically undergoes a five day regiment of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to an elongate tissue access assembly 104. The elongate tissue access assembly 104 houses components employed to construct an anchor assembly and is sized to fit into a 19F cystoscopic sheath for patient tolerance during a procedure in which the patient is awake rather than under general anesthesia. The tissue access assembly is stiff to allow manual compression of tissue at an interventional site by leveraging or pushing the handle assembly 102.

The anchor delivery device 100 further includes a number of subassemblies. A handle case assembly 106 including mating handle parts which form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members which facilitate assembly and delivery of an anchor assembly at an interventional site. A needle actuator 108 is provided and as described in detail below, effectuates the advancement of a needle assembly (loaded with a first component of an anchor assembly) to an interventional site. In a preferred embodiment, the needle assembly has a needle that moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the first anchor component. This action and the structure involved is also described in detail below. Finally, the delivery device 100 is equipped with a rear or proximal anchor actuator assembly 112 which as fully described below, upon actuation, accomplishes assembly of a second component to the anchor assembly and release of the anchor assembly at the interventional site.

Figure 4:
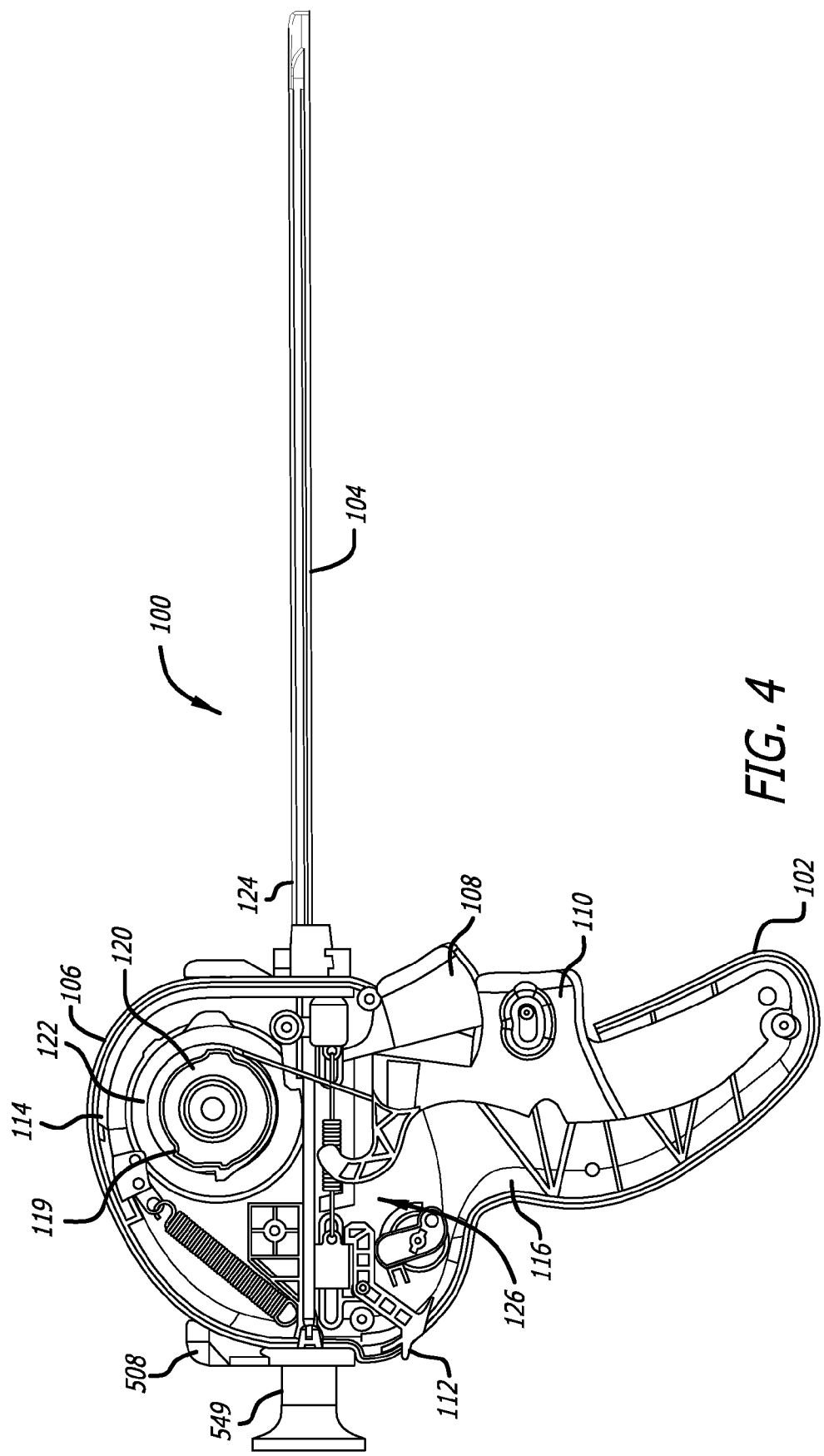
FIG. 4 is a side view, depicting the anchor delivery system of FIG. 3 with a portion of the casing removed and including a scope.
Figure 5:
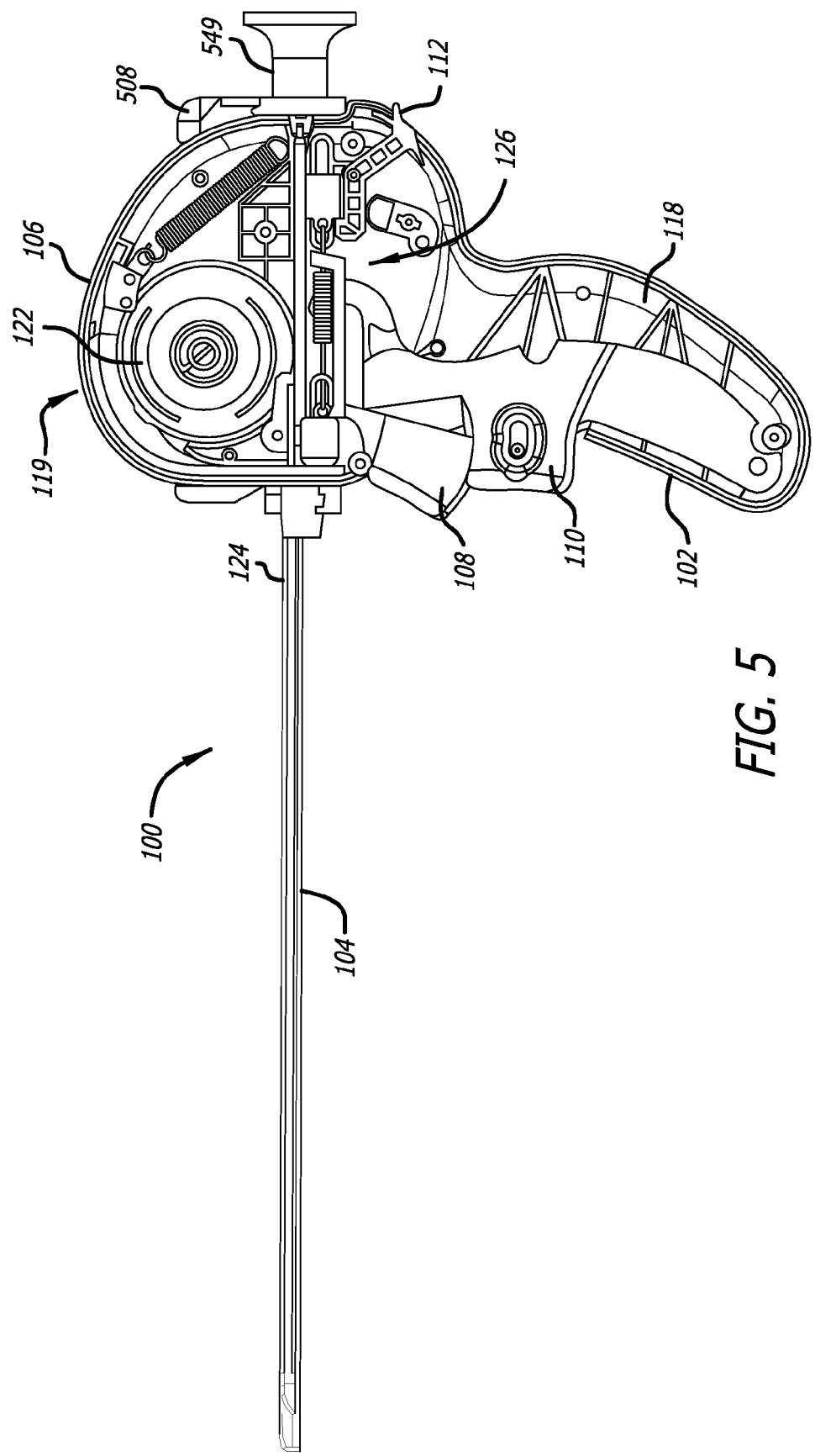
FIG. 5 is a left side view, depicting the anchor delivery device of FIG. 1 with a portion of the casing removed and including a scope.

Turning now to FIGS. 4-5 in addition to FIGS. 1-3, a number of the subassemblies of the delivery device 100 are introduced, the function and structure of each of which are addressed in detail below. In the embodiment depicted, the case assembly 106 has three mating parts, a left top case 114, a left bottom case 116, and a right case 118. It is within the scope of the present disclosure that the case assembly be made of a variety of numbers of parts. In addition to mating to enclose subassemblies, the case parts also include structural features for providing rigidity and support for the enclosed components.

Housed within the case assembly 106 are a distal anchor delivery mechanism 119 including a needle spool assembly 120 and a suture spool assembly 122 (referred to interchangeably herein as connector spool assembly 122). The rotational axes of the needle spool assembly and suture spool assembly are the same. A shaft assembly 124 includes a portion residing within the case assembly 106 and a portion extending from a forward end of the case assembly. Attached to and operatively associated with the shaft assembly 124 is a proximal anchor drive assembly 126. The drive assembly 126 is also housed within the case assembly 106. FIGS. 4 and 5 illustrate the juxtapositional relationships of the various subassemblies.

Figure 6:
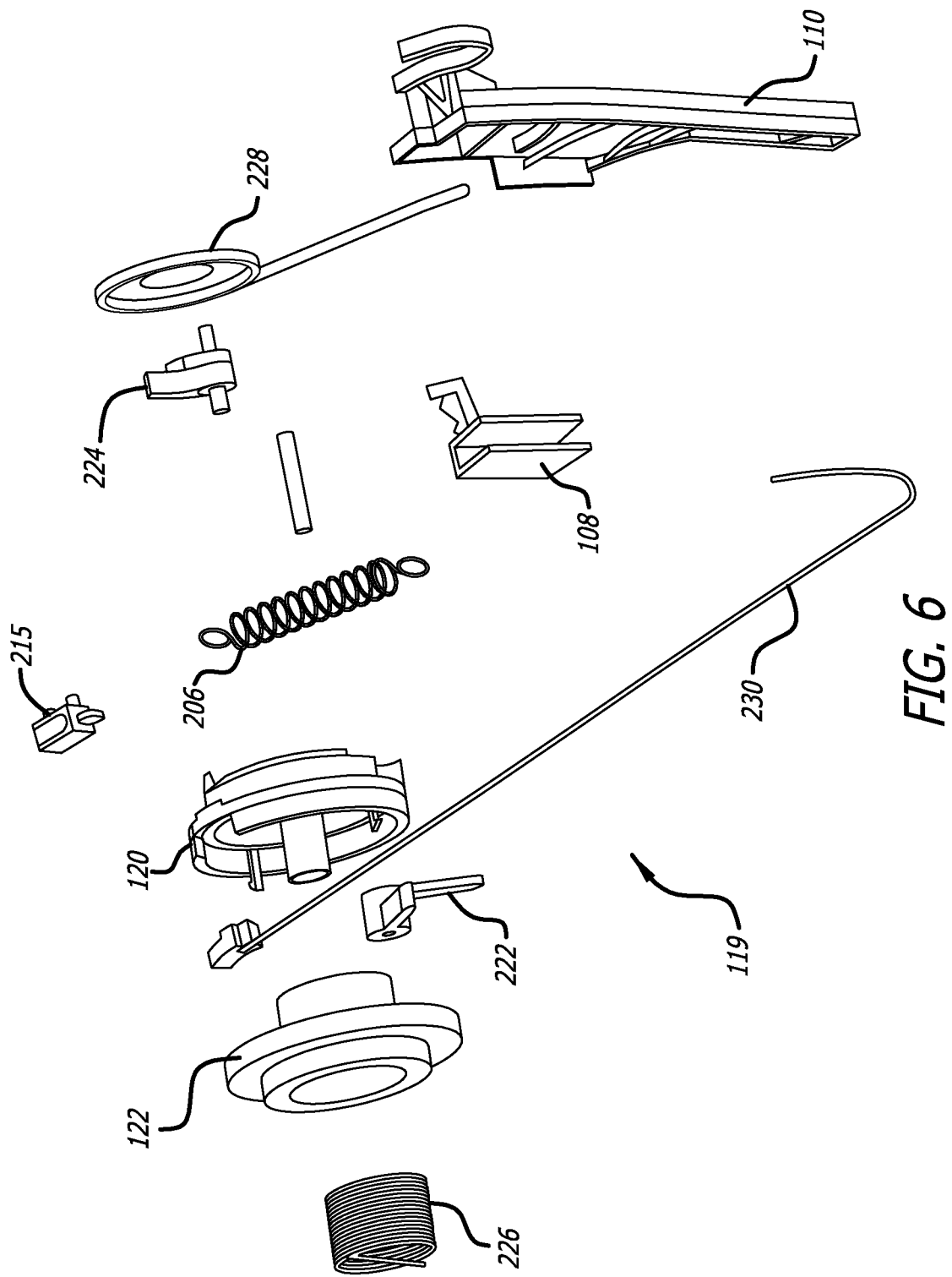
FIG. 6 is an exploded view, depicting components of a distal anchor delivery assembly.

With reference to FIG. 6, details concerning an embodiment of the structure of a distal anchor delivery mechanism 119 are presented. As described further below, the needle spool assembly 120 cooperates with the needle actuator 108 and needle retraction lever 110 to advance and then withdraw a needle assembly at an interventional site.

The needle spool assembly 120 is a generally disc-shaped structure having a number of landings and projections for engaging and receiving various structures of the distal anchor delivery mechanism 119.

A needle deploy spring 206 functions to rotate the needle spool 120 (referred to interchangeable herein as connector spool 120) and to project a tip of the needle through tissue with force and speed. One end of the deploy spring 206 is attached to the device casing and the opposite end is engaged with a shuttle 215. The shuttle 215, in turn, is operatively and releasably associated with the needle spool assembly 120. In one approach, it is contemplated that the device 100 be configured so that the needle is deployed to a single depth to pierce through a predominant population of urethral-prostatic distances in patients having an enlarged prostate.

The assembly further includes a needle deploy pawl 222 which is operatively associated with the needle actuator 108. As shown and described below, the needle actuator pivots the needle deploy pawl 222 away from engagement with the needle spool assembly 120, thereby permitting rotation of the same. The rotation of the needle spool assembly 120 is accomplished by forces generated by the deploy spring 206.

An unsheathing pawl 224 is also provided and configured at one end to engage the needle spool 120. At another end of the unsheathing pawl 224 there is structure configured to engage the suture spool assembly 122 (described below) to thereby fix its rotational position while the needle spool assembly 120 rotates. A tension spring 226 is positioned within a center bore of the suture spool 122 to provide tension to a connector or suture projecting from the suture spool 122. A lever lock and tape 228 is also provided to lock the lever 110 until after actuation of the needle actuator 108. The lever lock and tape 228 has a central axis or rotating point which is common with that of the needle spool 120 and suture spool 122 assemblies and also functions to retract a needle assembly upon depression of the lever 110. Also shown in FIG. 6 is the needle assembly 230.

Figure 7:
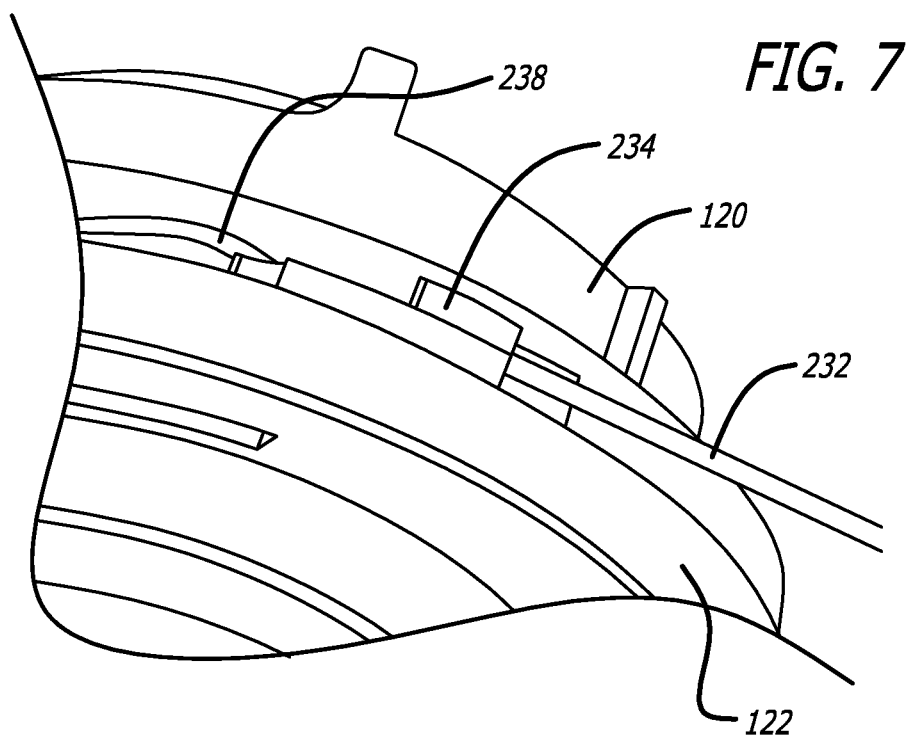
FIG. 7 is an enlarged view, depicting a proximal portion of the needle assembly attached to the needle drive spool assembly.
Figure 8:
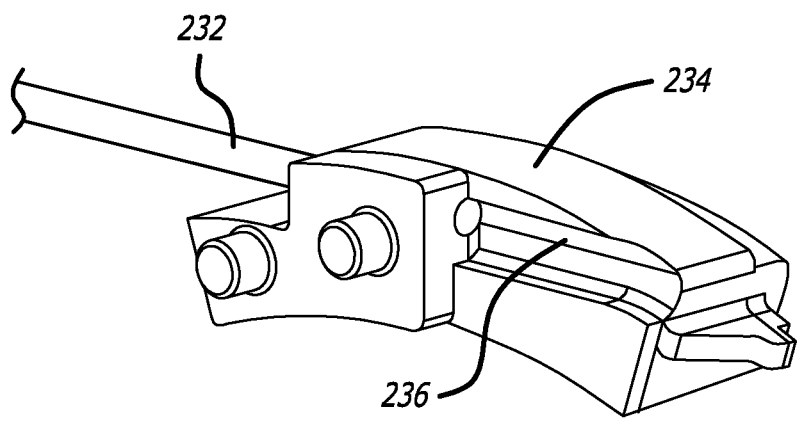
FIG. 8 is a perspective view, depicting further details of the connector depicted in FIG. 7.

As shown in FIGS. 7 and 8, a proximal end of a needle assembly 230 can be sized and shaped for connecting with the needle spool 120. In one approach, the proximal end 232 of the needle assembly 230 is equipped with a needle end bracket 234 for receipt within a corresponding recess formed near a periphery of the needle spool 120. Through such connections, rotation of the needle spool 120 can result in advancing and withdrawing lengths of a needle assembly. In this regard, as shown in FIG. 7, a peripheral recess formed in the needle spool 120 is provided to take up lengths of a needle assembly. Further, a recess 236 is formed in the needle end bracket 234 for guiding a proximal end of a connector of an anchor assembly to within a channel 238 formed in the needle spool 120. The needle spool channel 238 provides a path to the suture spool 122 (as described below).

Figure 9:
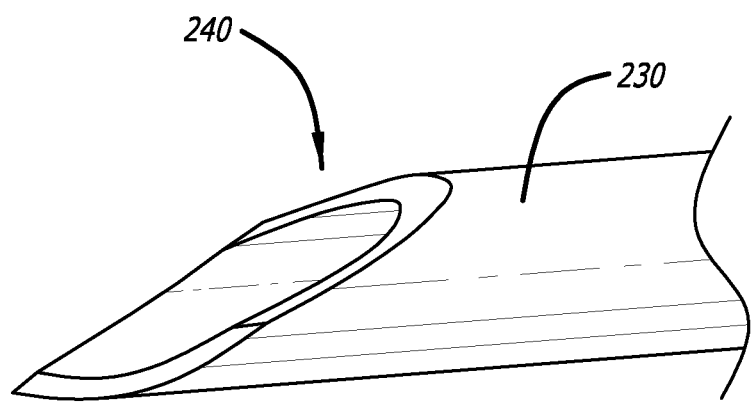
FIG. 9 is an enlarged view, depicting a distal terminal end of a needle assembly.
Figure 10:
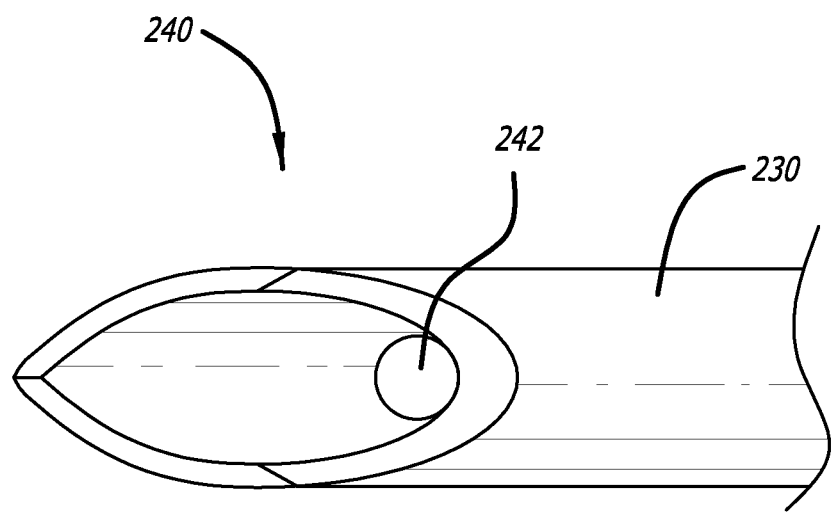
FIG. 10 is an enlarged rotated view, depicting further details of the needle of FIG. 9.

A distal end 240 of a generally tubular needle assembly 230 is shown in FIGS. 9 and 10. The distal end 240 defines a sharpened profile for piercing through tissue. In one particular approach, the distal end 240 embodies a 23° primary bevel geometry and a heal 242 of the bevel so as to closely match a 0.015" diameter connector structure of an anchor assembly. In this way, potential snags between the connector structure and needle assembly can be minimized or avoided.

Figure 11:
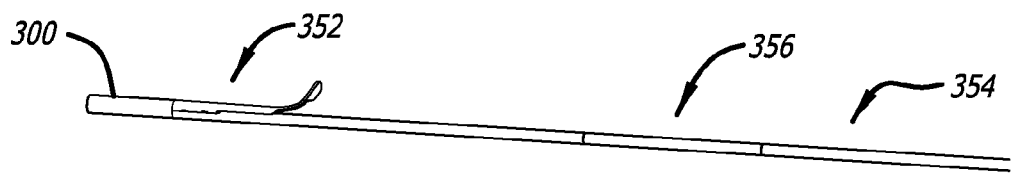
FIG. 11 is a side view, depicting a distal component and connector of an anchor assembly.
Figure 12:
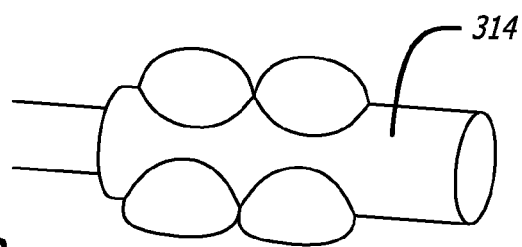
FIG. 12 is an enlarged side view, depicting a proximal terminal end of the connector of FIG. 11.
Figure 13:
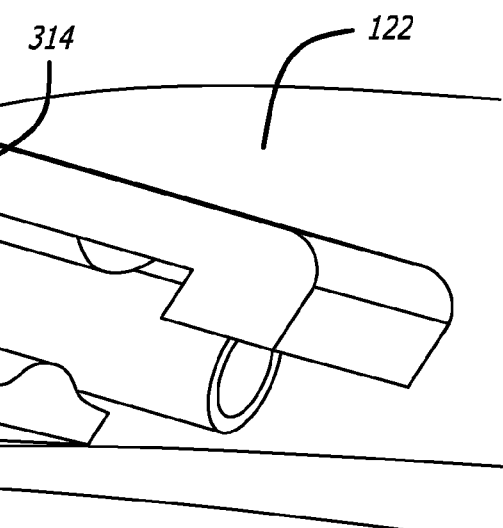
FIG. 13 is an enlarged view, depicting a connection between the proximal terminal end of the connector on a spool assembly.

One form of a distal anchor 350 and connector member 352 of an anchor assembly is shown in FIG. 11. It is the proximal end of the connector 352 which is fixed to the suture spool 122 by a ferrule 314 (See FIGS. 12 and 13). An annular space formed about the suture spool 122 is provided to receive a length of the pusher 354. The ferrule termination 314 offers a secure and inexpensive method for attaching the connector assembly 352 to the suture spool 122. The ferrule 314 can be easily pressed into receiving features of the spool assembly 122 and can be readily removed after the device is test fired on the production line. In an alternative embodiment, the connector to the suture spool can also define a plastic molded snap ferrule. In other alternative embodiments, the ferrule 314 can be replaced with an over molded component or an integral feature such as a bump in the connector member 352.

Figure 14:
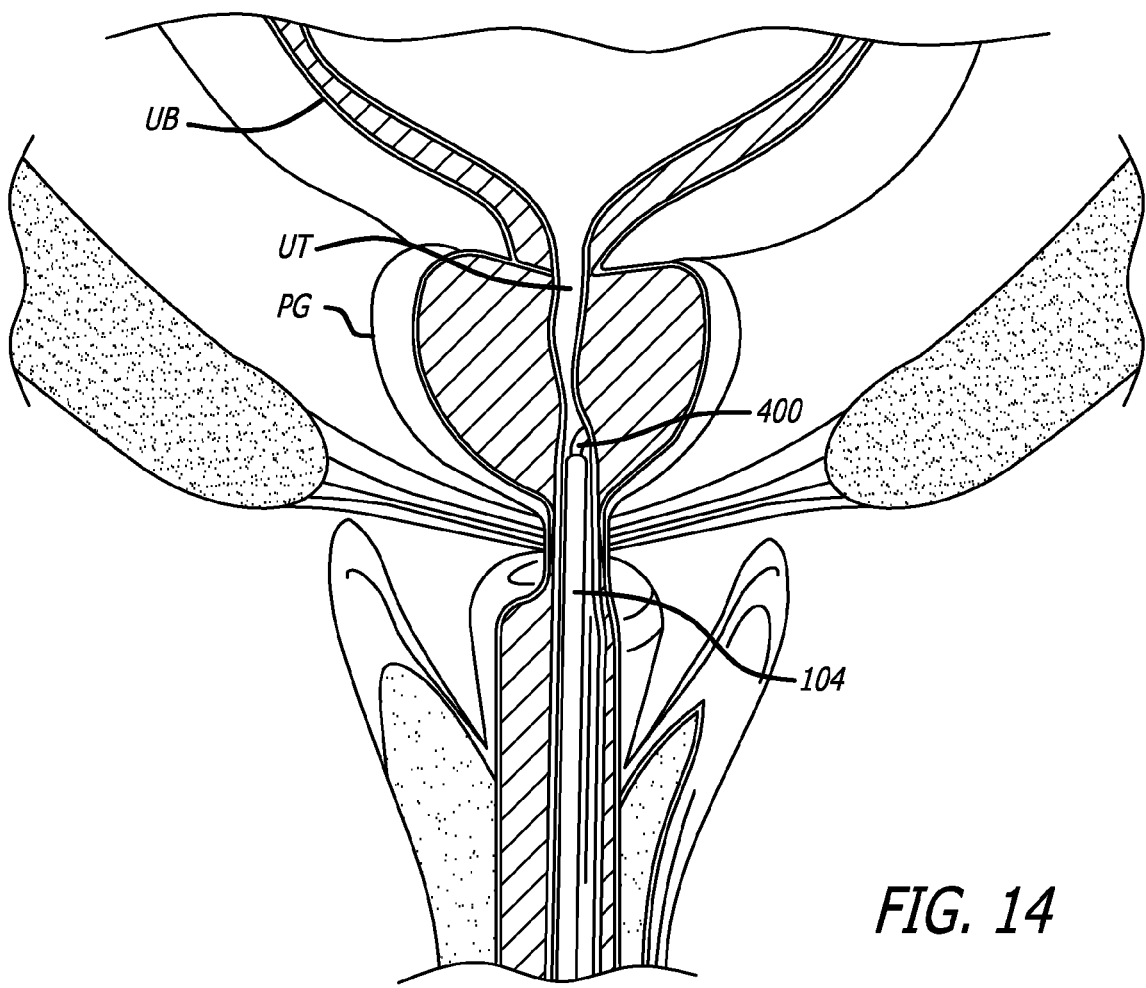
FIG. 14 is a cross-sectional view, depicting a first step involving an interventional procedure.

In one particular, non-limiting use in treating a prostate to improve LUTS (See FIG. 14), the elongate tissue access portion 104 of a delivery device can be placed within a urethra (UT) leading to a urinary bladder (UB) of a patient to position the device for implanting one or more anchor assemblies. Prior to the procedure, a transrectal ultrasound (TRUS) is contemplated to be performed. Using a transverse view, measurements will be made to determine the distances between the urethra and the prostatic capsule and to determine the extent of any middle lobe obstruction. Following induction of anesthesia, the patient can be placed in lithotomy position, prepped and draped as standard operating procedure. Cystourethroscopy can then be performed using a 19F cystoscope sheath, in the standard manner. The anchor delivery device pre-loaded with an anchor is then passed down the lumen of the sheath in the same manner as a resectoscope. The cystoscope is then positioned at the hyperplastic lobe and then rotated to the pre-determined direction (typically 2 o'clock or 10 o'clock), using the transverse prostatic measurements gained by TRUS. Applying firm pressure against the wall of the preferred lateral lobe, a 19 gauge needle can then be advanced from the delivery device and passed through the prostate tissue and pubic fascia so that the needle is positioned just outside the prostatic capsule. Fluoroscopy and/or TRUS can be used to assure that the needle is deployed in the correct trajectory and did not enter the bladder. Once satisfactory needle deployment is achieved, the capsular anchor is delivered through the needle by advancing a delivery pusher, situated within the needle. The needle is then retracted, and the suture is tensioned automatically. The urethral anchor was then deployed at the desired point against the prostatic urethral wall under direct endoscopic guidance, so as to retract the anchored lobe and open the urethra. During urethral anchor deployment, the excess suture is trimmed and the anchor released into position against the urethra. After cystoscopic confirmation of satisfactory retraction of the anchored lobe, the procedure can be repeated on the contralateral side, if necessary. An assessment can be conducted to determine the number of implants to be placed in each lateral lobe. On completion of the procedure, a cystoscope was introduced to evaluate any immediate retraction of the lateral lobes. A post-operative transverse TRUS image is then completed for comparison with the pre-operative view. Pre and post-operative cystoscopic images can also be taken.

Figure 15A:
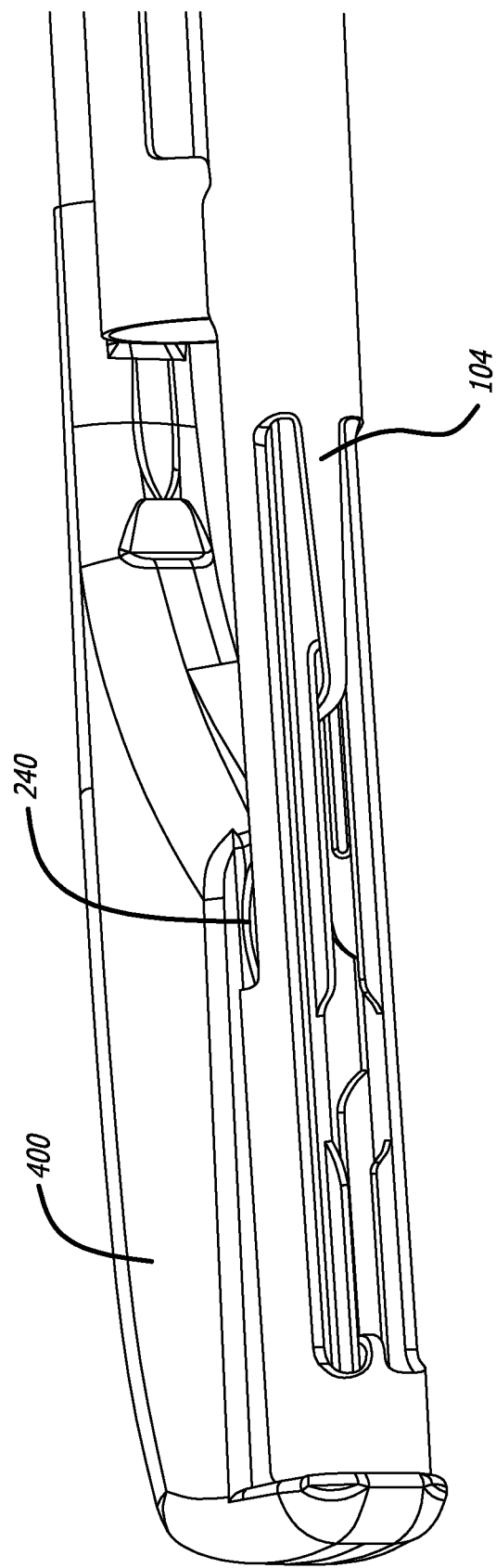
FIG. 15A is a perspective view partially in cross-section, depicting a distal terminal end of a delivery device.
Figure 15B:
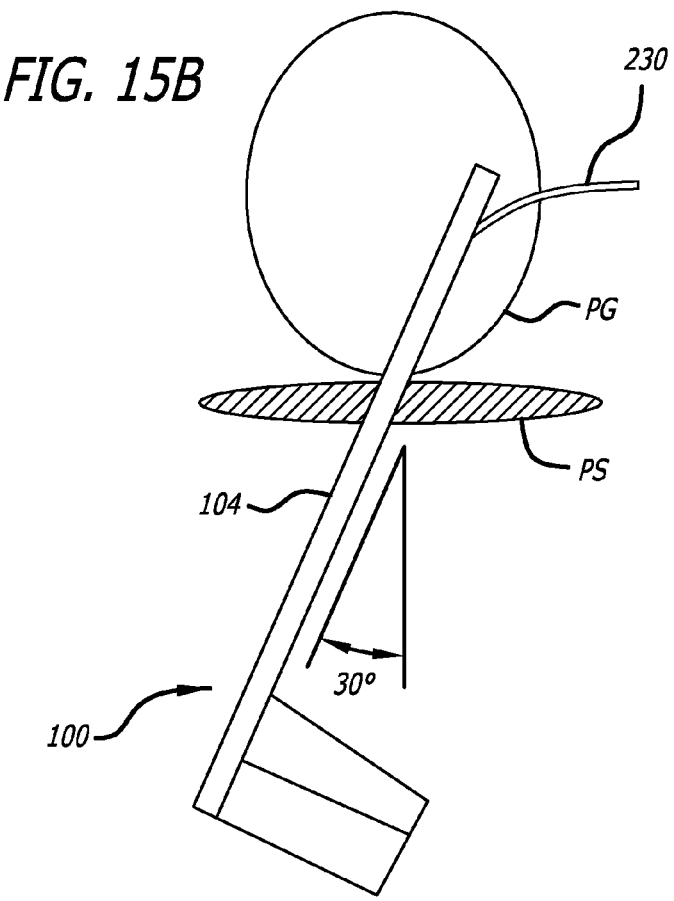
FIG. 15B is a schematic representation approximately in coronel plane, illustrating the angling of the anchor delivery tool within anatomy.
Figure 15C:
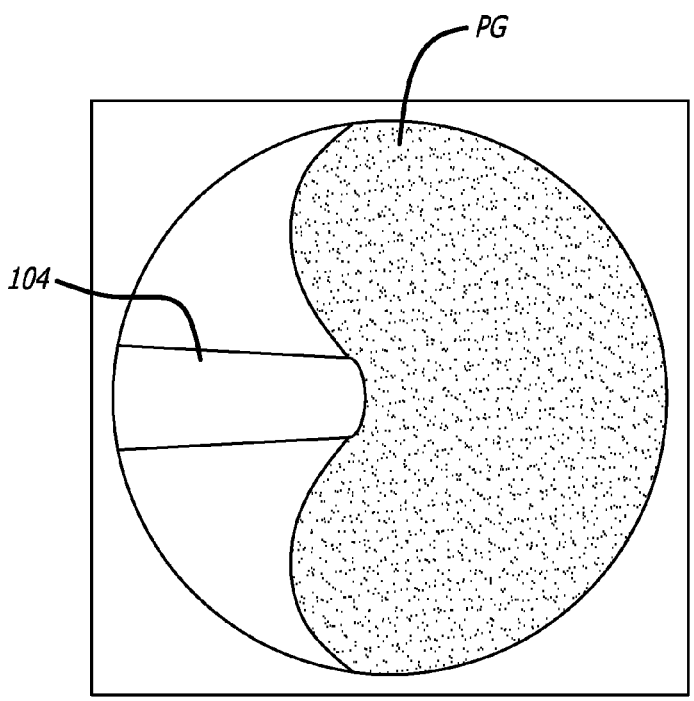
FIG. 15C is an enlarged view, depicting proper placement of treatment structure against tissue anatomy.

In one particular approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate portion 104 is advanced within the patient until a leading end 400 thereof reaches a prostate gland (PG). In a specific approach, the side(s) (i.e., lobe(s)) of the prostate to be treated is chosen while the device extends through the bladder and the device is turned accordingly. The device is first positioned at the bladder neck and then retracted approximately 1 cm while keeping the device parallel to the prostatic fossa and preserving mucosa. As shown in FIG. 15 A, when so placed, the distal end 240 of the needle assembly is withdrawn within the leading end 400 of the device. The distal end of the elongate portion can be used to push the urethra into the prostate gland. The inside of the prostate gland (i.e., adenoma) is spongy and compressible and the outer surface (i.e., capsule) of the prostate gland is firm. By the physician viewing with the endoscope, he/she can push the urethra into the prostate gland compressing the adenoma and creating the desired opening through the urethra. To accomplish this, the physician rotates the tool anterior between 9 and 10 o'clock for the patient's side left lobe and between 2 and 3 o'clock for the patient's side left lobe. The physician then pivots the tool laterally about the pubic symphysis PS, generally about 20 to 30 degrees relative to the patient's midline (See FIG. 15B which depicts an image approximately in coronal plane). Viewing through the endoscope, the physician wants to have about the same amount of tissue protruding on both sides of the elongate shaft (See FIG. 15C).

Figure 16:
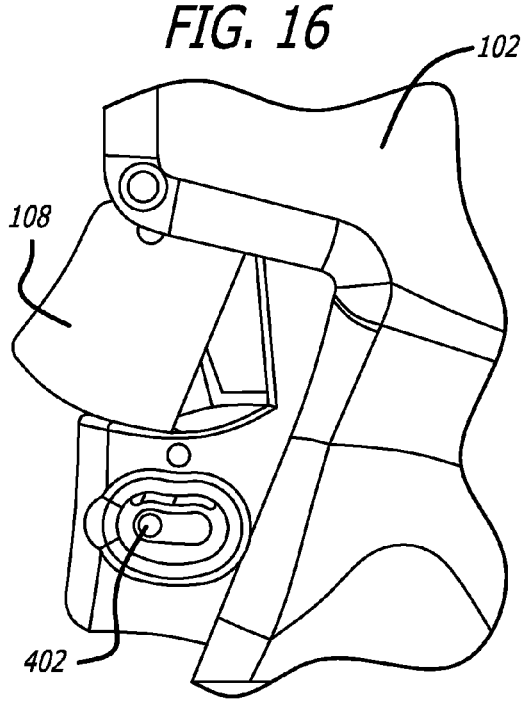
FIGS. 16-19 are side views, depicting unlocking and depression of an actuator of a delivery device.
Figure 17:
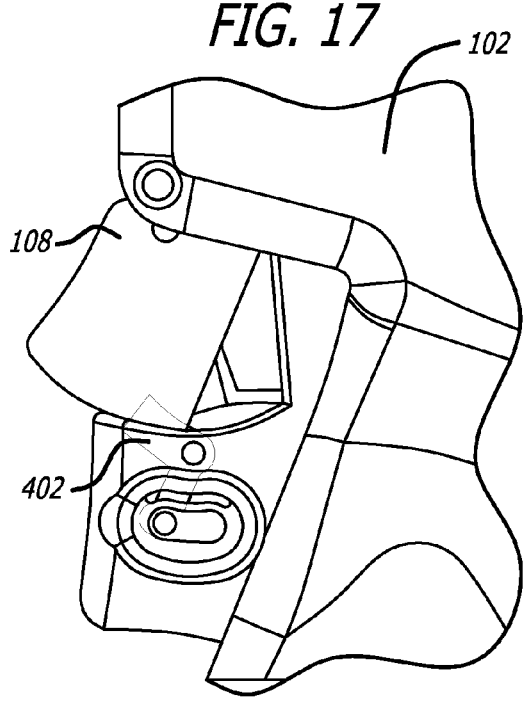
Figure 18:
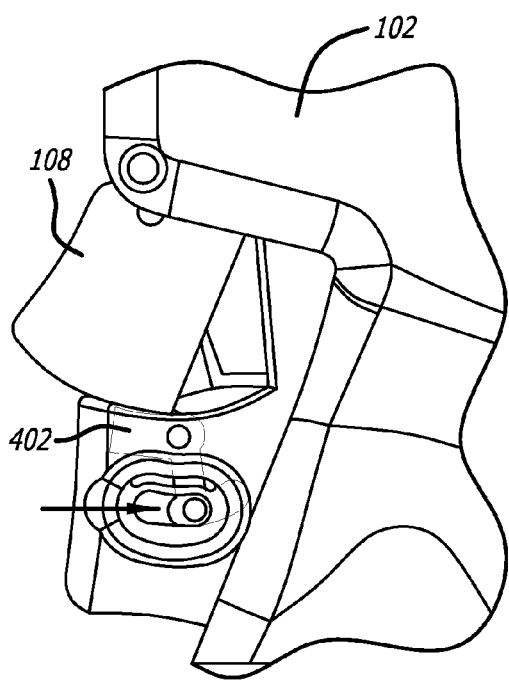
Figure 19:
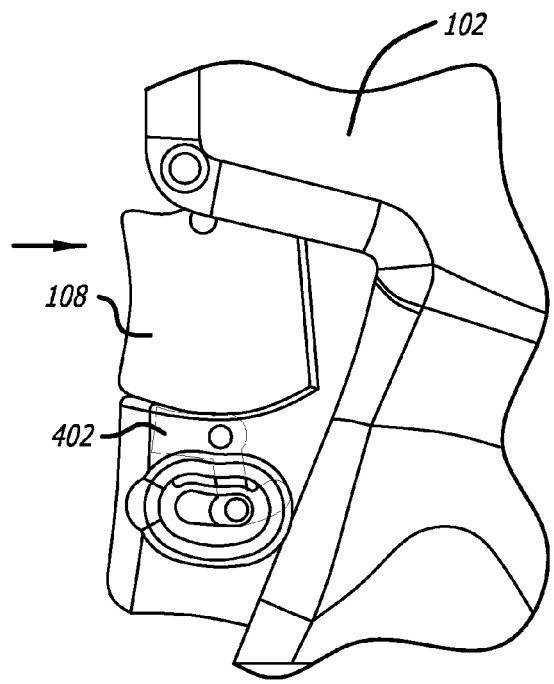

As shown in FIGS. 16 and 17, the delivery device is at this stage configured in a ready state. The needle actuator 108 and the needle retracting lever 110 are in an inactivated position. The needle actuator 108 is locked by a pivoting safety mechanism 402 in an inactive position. To unlock the needle actuator (See FIGS. 18 and 19), the safety mechanism 402 is rotated out of engagement with the needle actuator 108 by applying a lateral force on a projection of the safety mechanism 402.

Figure 20A:
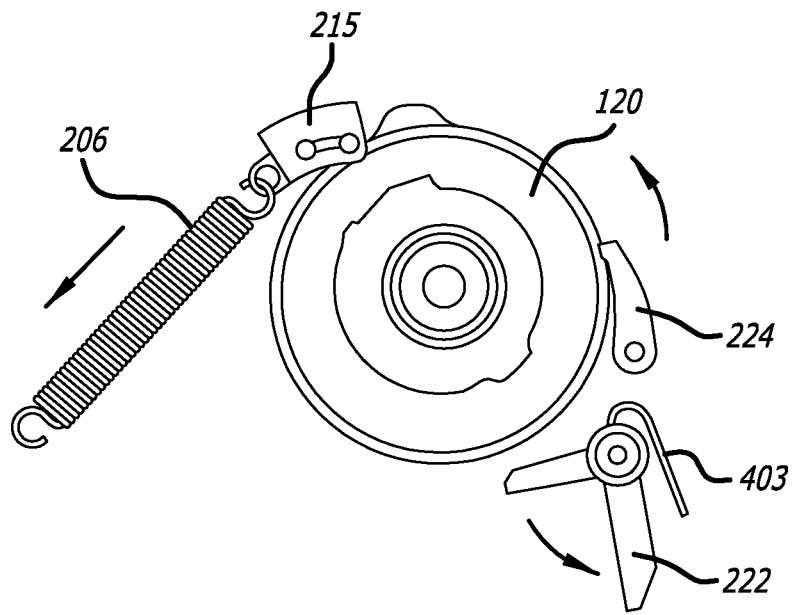
FIGS. 20A-B are views of selected internal components of the delivery device, depicting action of the needle and connector spools of a delivery device.
Figure 20B:
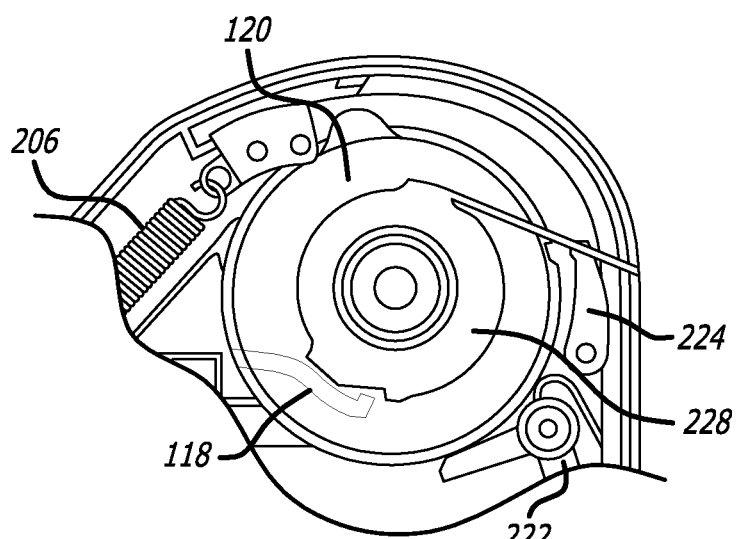

Upon depression of the needle actuator 108 (FIG. 19), an upper end of the actuator 108 engages and rotates the needle deploy pawl 222 out from engagement with the needle spool 120 (See FIGS. 20A and B). This action overcomes the friction with needle spool 120. Disengagement of the deploy pawl 222 from the needle spool 120, permits the needle deploy spring 206 through its connection via the shuttle 215, to rotate the needle spool 120. The needle spool 120 rotates until the unsheathing pawl 224 catches an external surface of the suture spool 122 and until the needle spool 120 bottoms out against the case 228. At the end of the needle stroke, the lever lock and tape 228 becomes disengaged from the right case 118. The shuttle in this embodiment disengages from the needle spool so the needle deploy spring 206 can no longer apply a force to the needle spool 120 via the shuttle 215.

Figure 23:
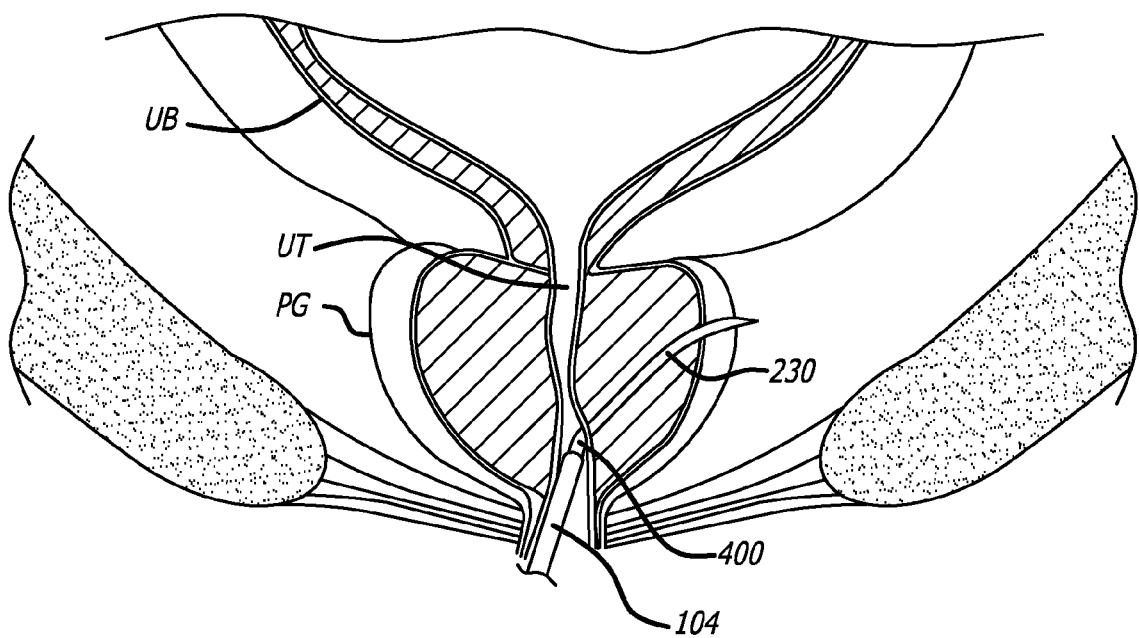
FIG. 23 is a cross-sectional view, depicting advancement of a needle assembly at an interventional site.

At the leading end 400 of the delivery device, as shown in FIGS. 21 and 22, such action results in the needle assembly being advanced from within the elongate member 104. As is to be appreciated, the needle is ejected by the needle deploy spring 206 in this embodiment in a direction commensurate with the direction the handle assembly extends. Moreover, the needle assembly can be configured so that it curves back toward the handle as it is ejected. In use in a prostate intervention (See FIG. 23), the needle assembly 230 is advanced through and beyond a prostate gland (PG). To facilitate the same, the device can be pivoted 20° to 30° laterally (pivoting about pubic symphisis). Additionally, the device can be rotated anteriorly to lift a prostatic lobe (as described previously). The spring deployment helps to ensure the needle tip passes swiftly through the tough outer capsule of the prostate without "tenting" the capsule or failing to pierce the capsule. In an alternate embodiment, the needle could be manually deployed by the user. In one approach, the needle 230 is made from Nitinol tubing and can be coated with Parylene N. Such a coating helps compensate for frictional or environmental losses (i.e. wetness) which may degrade effectiveness of needle penetration.

Figure 24A:
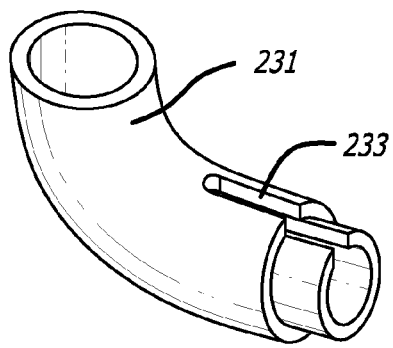
FIGS. 24A-C are perspective and partial cross-sectional views, depicting an alternative approach to a needle assembly.
Figure 24B:
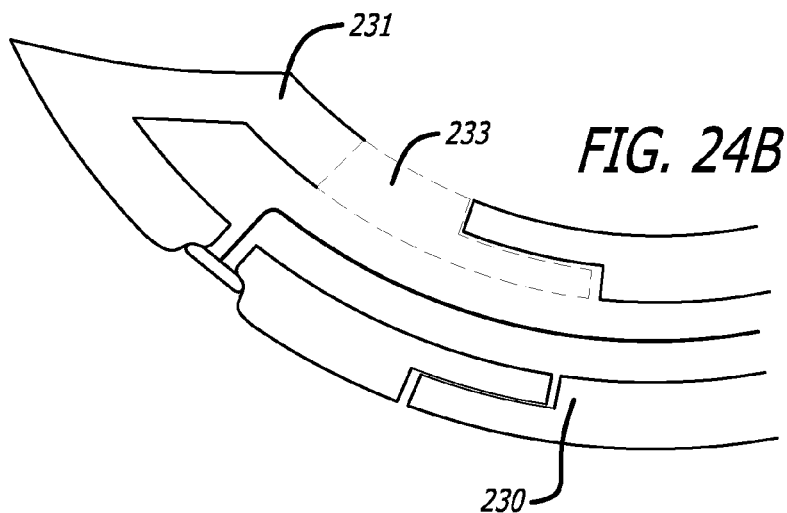
Figure 24C:
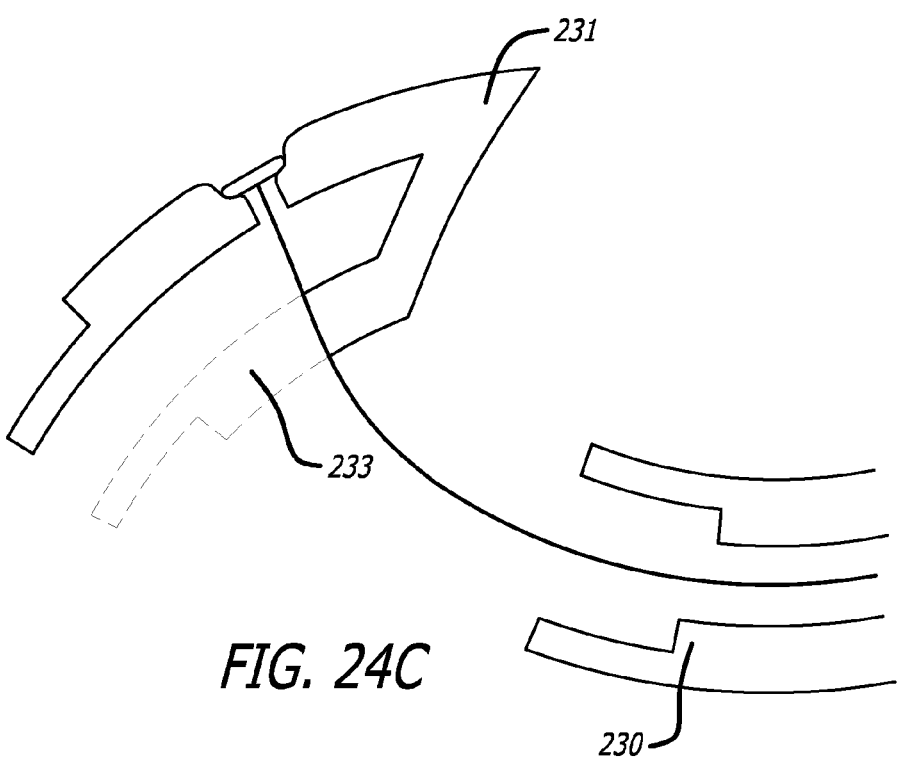

It is also contemplated that the needle assembly 230 can include an integral tip and capsular anchor 231 which is releasably configurable at a distal end of the needle assembly 230 (See FIGS. 24A-C). Upon needle retraction, the tip-anchor 231 remains on an outside of a prostate capsule. The tip-anchor 231 can have a solid tissue piercing surface providing increased strength and structure for passing through tissue. Moreover, being configured to be released from a proximal length of the needle assembly 230, such a proximal portion can assume a smaller diameter since the capsular anchor 231 does not need to reside within the needle assembly 230. A smaller profile needle assembly can in turn lead itself to providing more flexibility in delivery apparatus structure and aid in advancing the assembly to an interventional site. This approach also can avoid any interference which may occur with an approach involving ejecting an anchor from within a hollow needle. Further, the tip-anchor 231 can include a slot 233 which facilitates flipping of the anchor into a position on the outside of a prostate capsule.

Figure 25A:
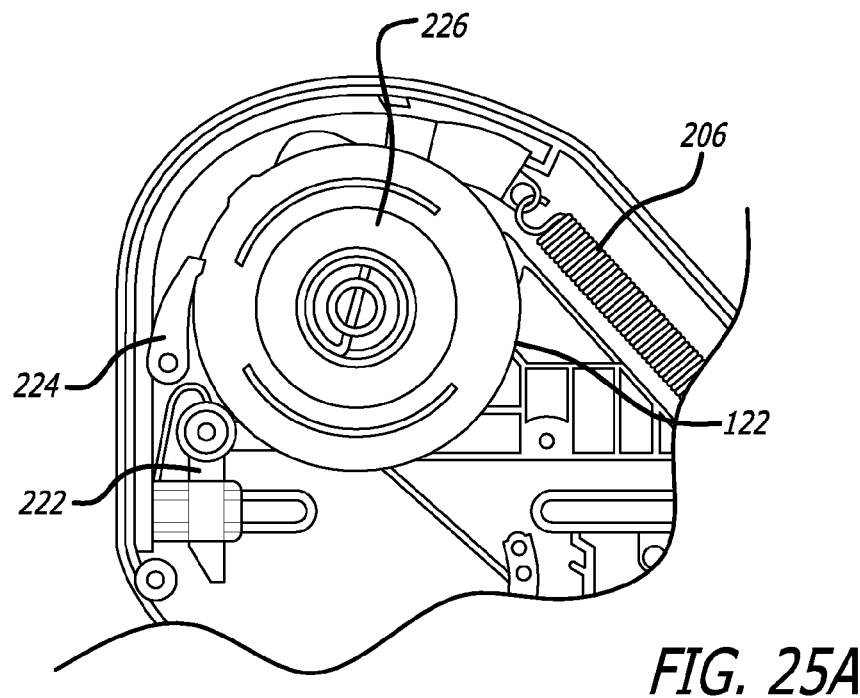
FIGS. 25A-B are partial cross-sectional views, depicting further details concerning action of internal components of a delivery device upon actuation of a lever assembly.
Figure 25B:
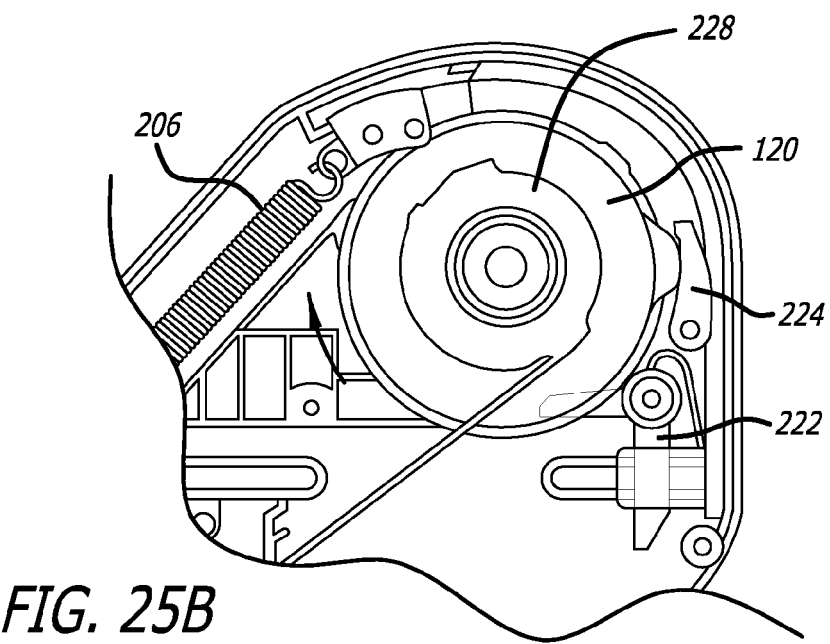
Figure 27:
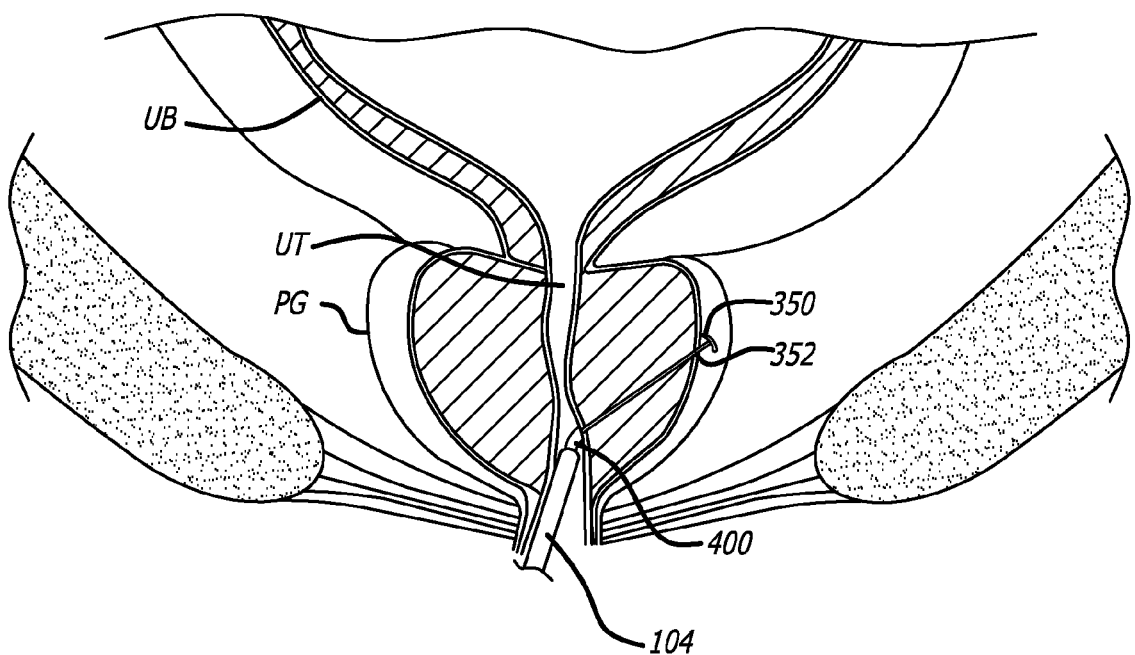
FIG. 27 is a cross-sectional view, depicting delivery of a first component of an anchor assembly at an interventional site.

After complete depression of the needle actuator 108 and the unlocking of the needle retraction lever 110, the needle retraction lever 110 can be actuated (See FIGS. 25A-B). When so actuated, the tape portion of the lever lock and tape 228 cooperates with the lever 110 to rotate the needle spool 120 in an opposite direction while the suture spool 122 is held stationary. Such action results in a withdrawal of the needle assembly 230, leaving the connector 352 of an anchor assembly in an extended position (See FIG. 26). In one embodiment, the needle 230 is withdrawn further than its original position within the device pre-deployment. When extended, the connector 352 extends through the needle window and is centered by suture guide structure (as described below). As shown in FIG. 27, in a prostatic interventional procedure, the same results in delivering a first or distal anchor component attached to the connector 352 beyond an outer surface of a prostate gland (PG) with the connector 352 within a penetration tract in the prostate gland extending toward the terminal end 400 of a delivery device.

The tensioning spring 226 provides the tension forces which helps to ensure the distal anchor is pulled back into firm contact with a desired tissue plane such as, for example, the outer capsular surface of the prostate gland (FIG. 25A). Notably, the spring in a preferred embodiment provides a force such as up to 1-2 pounds or more of tension. In another embodiment, a spring can be used to automatically retract the needle assembly.

The timing of the needle retraction and tensioning is accomplished through the interaction of the unsheathing pawl 224 and the suture spool 122. As shown in FIGS. 20A-B, 24 and 25, the unsheathing pawl 224 is configured to permit a rotation of the suture spool 122 which occurs during needle actuator depression until the unsheathing pawl 224 registers within grooves formed in the suture spool 122. Actuation of the needle retraction lever 110 causes a deflection of the unsheathing pawl 224 (See FIG. 25B) which disengages the unsheathing pawl 224 from the suture spool 122. Since the suture spool 122 is at this point disengaged from the operation of the spring arbor as described above, the suture spool 122 is permitted to rotate in an opposite direction. This rotation continues until the suture spool bottoms out on the needle spool 120. Complete depression of the lever 110 also then results in the lever locking against the case assembly 106. The tensioning spring 226 is then left to automatically provide a consistent tensioning force on a connector of an anchor assembly. Such tensioning results in seating a distal or first anchor component 350 as desired within an interventional site such as shown in FIG. 27 as well as to minimize a distance between two anchor members of an implanted anchor assembly. The tension generated after seating the anchor component 350 can be different from that during delivery of the connector of the anchor assembly.

A more detailed description of the shaft assembly now follows as does a description of the operation of the structure achieving assembly of a second or proximal anchor component to a connector of an anchor assembly and release of a complete anchor assembly at the interventional site.

Figure 28A:
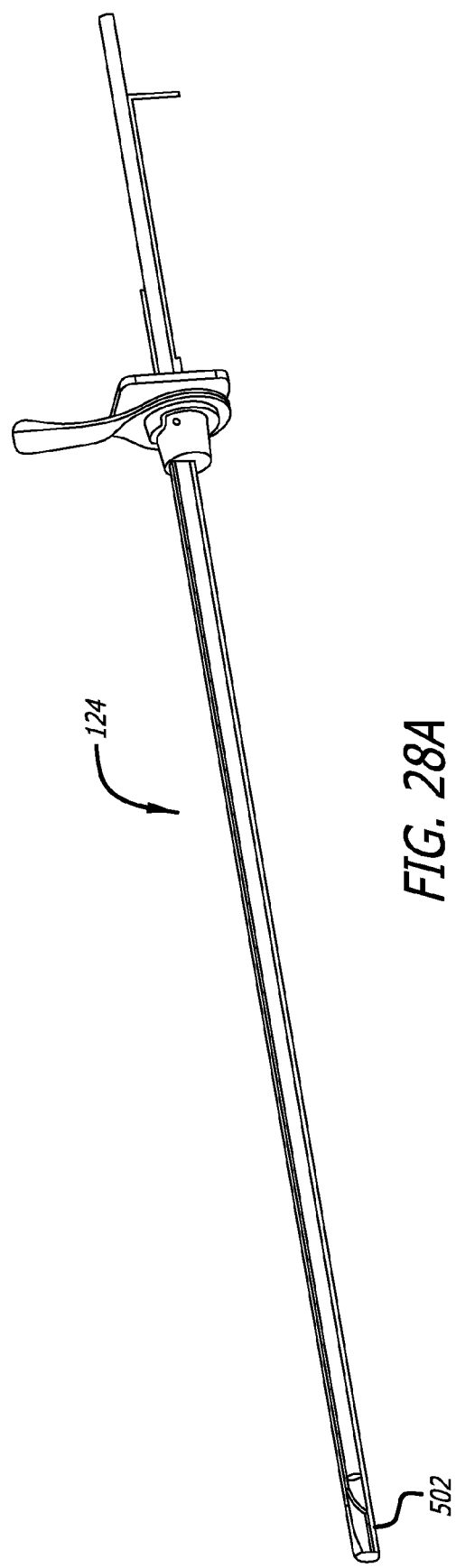
FIGS. 28A-B are perspective and exploded views, depicting various components of a shaft assembly of the delivery device.
Figure 28B:
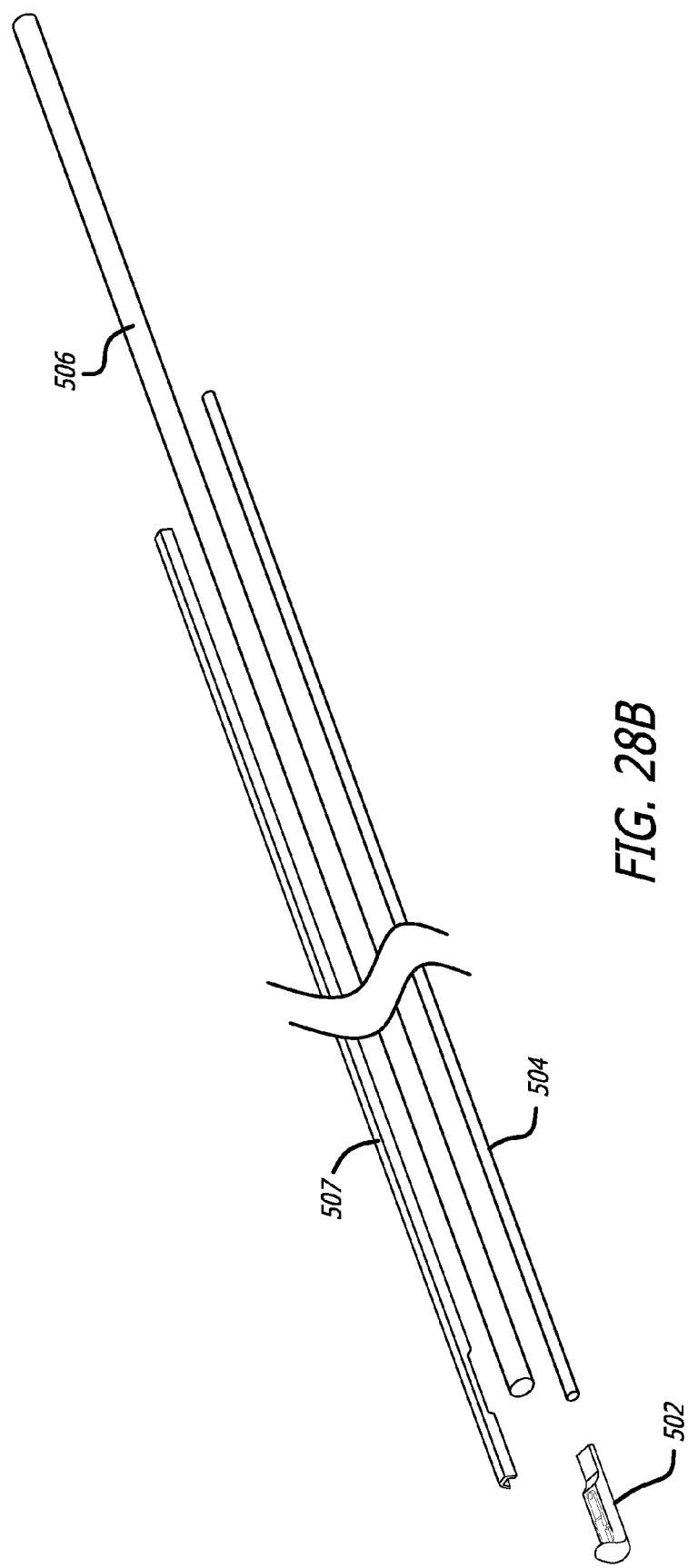

With reference to FIGS. 28A-B, there is shown an embodiment of a shaft assembly 124. Components of the shaft reside within the device case assembly 106 and include structure attached to and cooperating with proximal anchor delivery and assembly structure. A terminal end portion 400 of the shaft assembly 124 includes an atraumatic distal tip 502. Proximally located to the tip 502 is a tubular shaft assembly 504 which is sized and shaped to slidably receive the needle assembly. An internal portion of the tip 502 is curved so that a needle projecting therefrom extends in a direction generally corresponding to that of a handle element of the delivery device. Configured longitudinally adjacent the tubular shaft assembly is a scope tube 506 which is sized and shaped to receive a scope as described previously. Configured below and longitudinally adjacent the scope tube 506 is an elongate cover 507 which is sized to receive elongate portions of the cutter and pusher assemblies.

As shown in FIGS. 29-32, the shaft assembly 124 can alternatively be formed from modular pieces. For example, a telescope tube 506 can be employed as a backbone about which a molded tip 502 and a shaft extension 509 are configured. An atraumatic tip sleeve 591 can be placed over the tip 502 and an elongate cover 507 can be placed longitudinally along the shaft extension 509. This modular shaft assembly permits the use of injection molded components to form the shaft. Injection molded components are less expensive and can lead themselves to easy and quick assembly. Moreover, different materials can be chosen for the various shaft components to thereby provide desired shaft stiffness. Further, in one contemplated approach, a clear sheath hood 515 can be configured about the distal tip 502 so that a matching of a sheath and a distal portion of the device can be better accomplished.

Figure 33A:
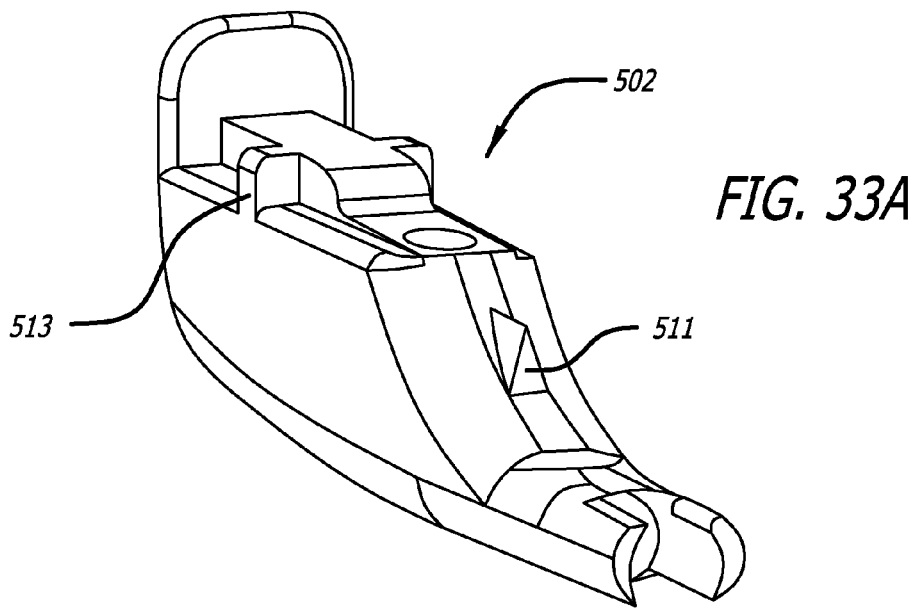
FIGS. 33A-34 are perspective views, depicting embodiments of a terminal end of the delivery device.
Figure 33B:
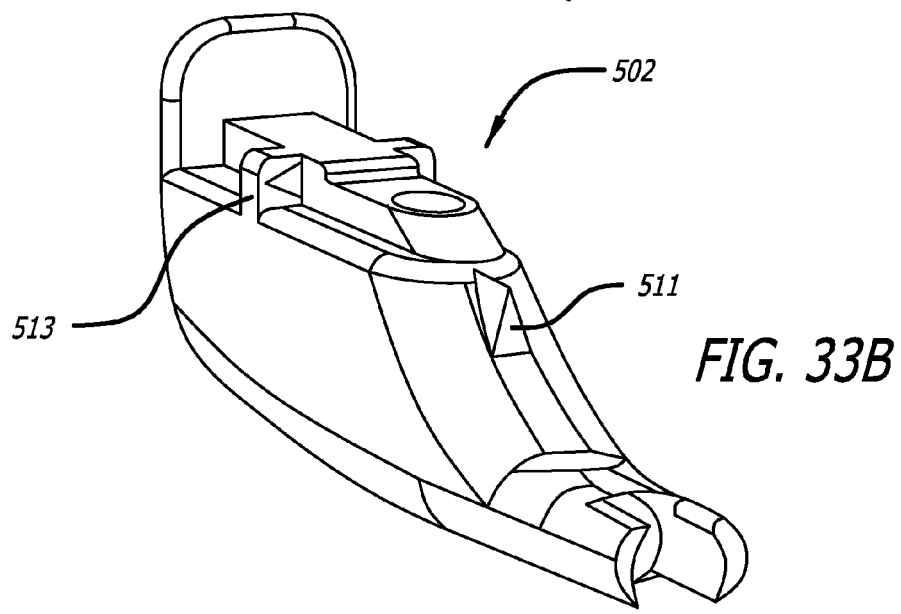
Figure 34:
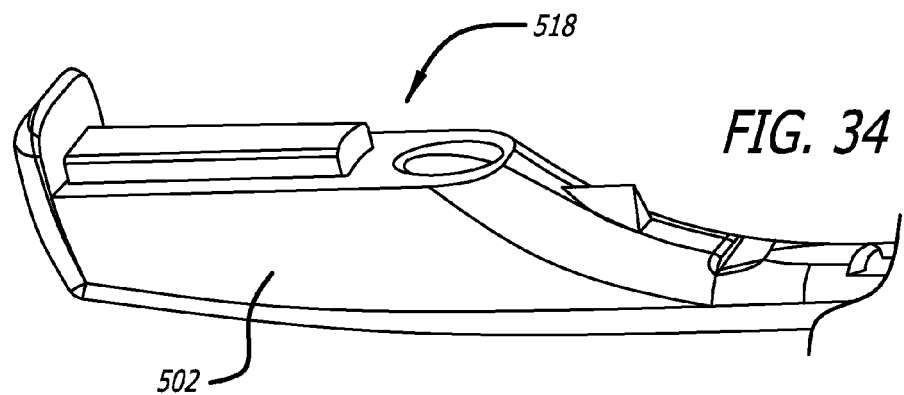

During use of the present device, viewing of the interventional site is accomplished through a telescope which can involve a foreshortening effect in the field of view. In addition, because of the speed of the needle and the end of the tool being pressed into the tissue and the lobes protruding on each side, the operator may not know or see where the needle assembly will exit the device and/or engage tissue. Therefore, a needle directing arrow 511 can be included on the tip 502. The distal tip 502 can also include indicators which facilitate providing the operator with further orientation guides. In one approach (FIG. 33A), an indicator 513 can be placed on lateral projections of the tip 502. Another approach can involve an indicator 513 defining a laterally directed arrow 511 (See FIG. 33B). Thus, the tip indicator 513 can be pushed directly against tissue to show where the needle will exit and subsequently where a proximal anchor will land. In yet another approach (FIG. 34), a reflective surface 518 can be configured on the distal tip 502 distal to where the connector exits the tip 502. In this way, light can be reflected back onto the connector to thus light up the area and improve visualization of the connector when the area is dark. A circular, elliptical, parabolic or straight cut can be made and provided with a reflective surface. These features can alternatively be incorporated into a cover assembly as a separate part or adhered to the cover with atraumatic tape or be part of the tap itself. The features in some embodiments take advantage of a light source associated with the viewing apparatus being employed and reflect light back providing a bright appearance. The relatively perpendicular angle of the indicators with respect to the light source results in significant contrast. In one embodiment, a small fiber optic resides in the shaft assembly, such as parallel to the cover on the outside or inside the cover parallel to the cutter, using the same light source as the endoscope/telescope. The fiber can have a right angle output so that the light shines onto the tissue.

Figure 35:
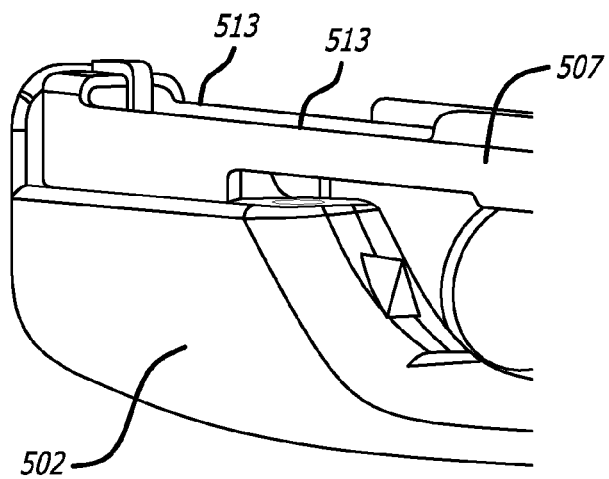
FIGS. 35-37 are perspective views, depicting contemplated features of a cover assembly.
Figure 36:
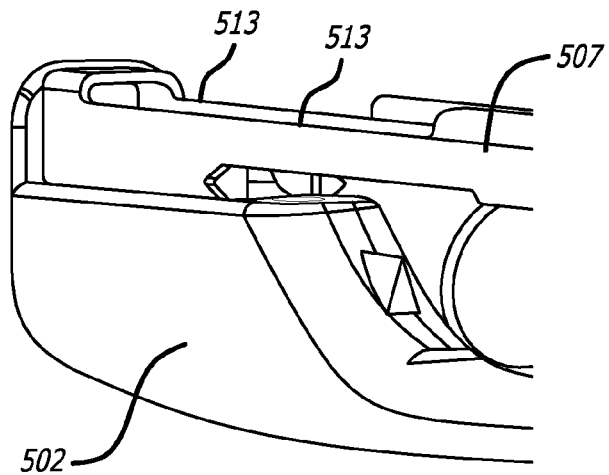
Figure 37:
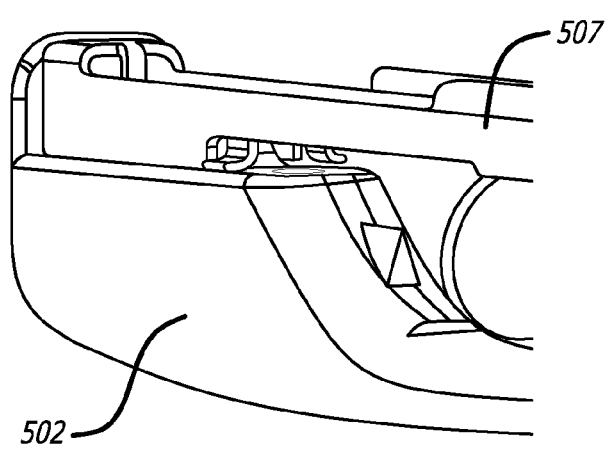

In another approach to providing the operator with orientation, as stated, the cover 507 can include indicators. As shown in FIGS. 35-37, the cover 507 can include indicators 513 on faces generally perpendicular to the viewing orientation. It is to be noted that such indicators can assume various shapes such as rectangles and arrows.

Figure 38:
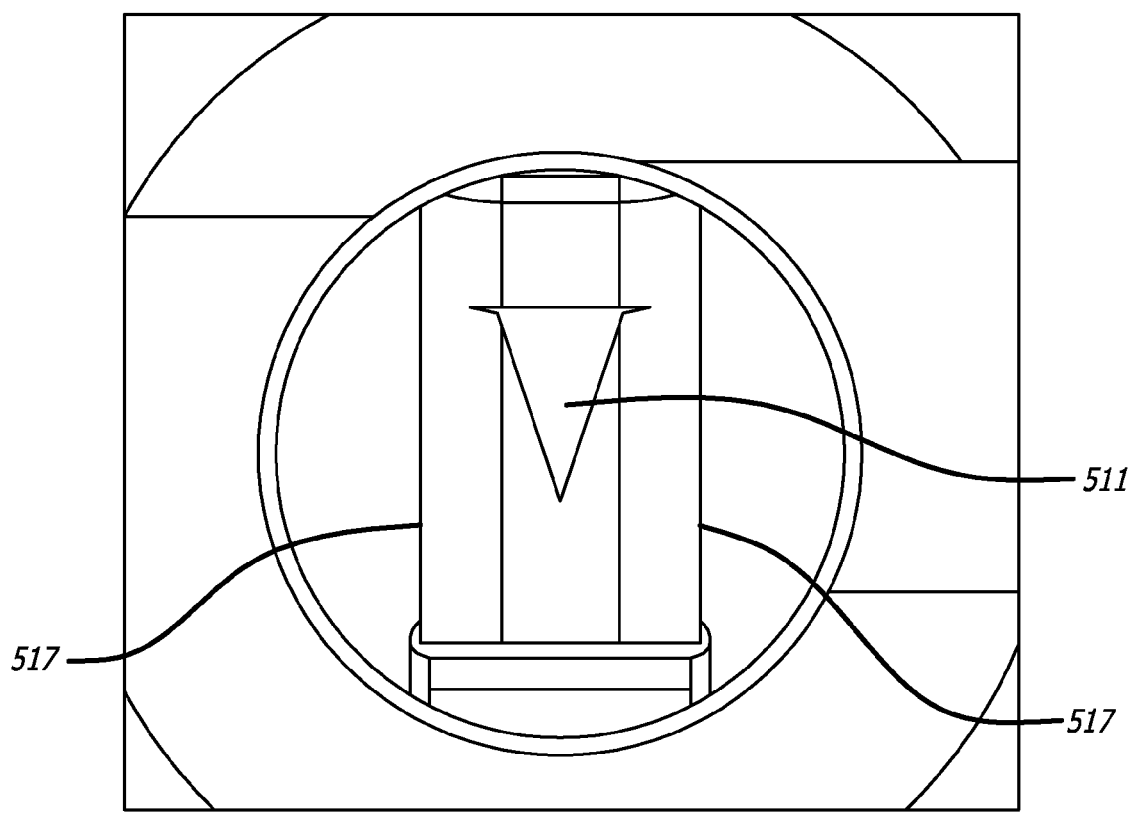
FIG. 38 is a schematic view, depicting further orientation features contemplated for the delivery device.

In a related approach (See FIG. 38), the present device can include vertical indicators 517 to aid in keeping a connector of the anchor assembly centered relative to a proximal anchor component during assembly and delivery of the anchor assembly. There is a controlled delay between the application of tension to a connector and the delivery of a proximal anchor at an interventional site. During this delay, the connector can potentially get off-center or move too far distal relative to the proximal anchor component. The vertical lines 517 thus aid an operator with manually guiding the connector into an optimal position such as placing the connector parallel to or between the vertical line indicators 517. The indicators can be formed from small wires running vertically in the scope view distal of the scope and proximal of a centered connector position. The tip or cutter can also be modified to include such vertical lines formed for example, by etching.

Figure 39:
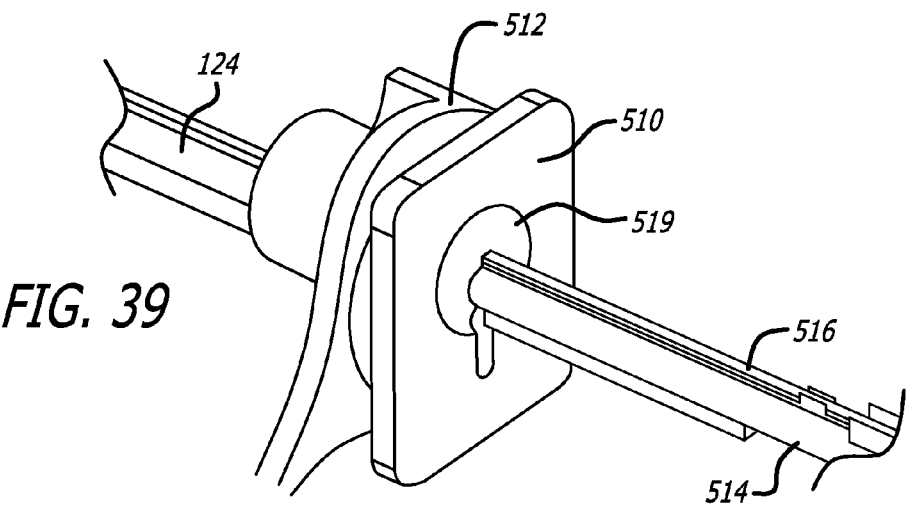
FIGS. 39 and 40 are a perspective view and side view, depicting one approach to a sheath mount assembly and shaft seal assembly.
Figure 40:
Figure 41:
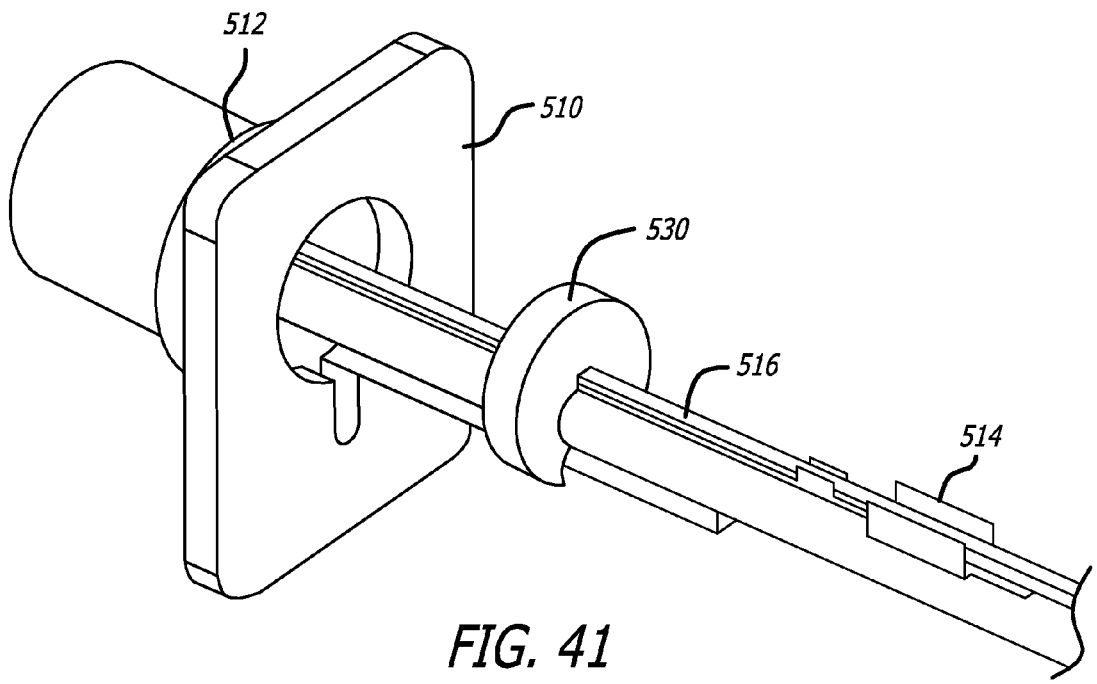
FIGS. 41 and 42A-B are perspective views, depicting an alternative approach to a shaft seal assembly.
Figure 42A:
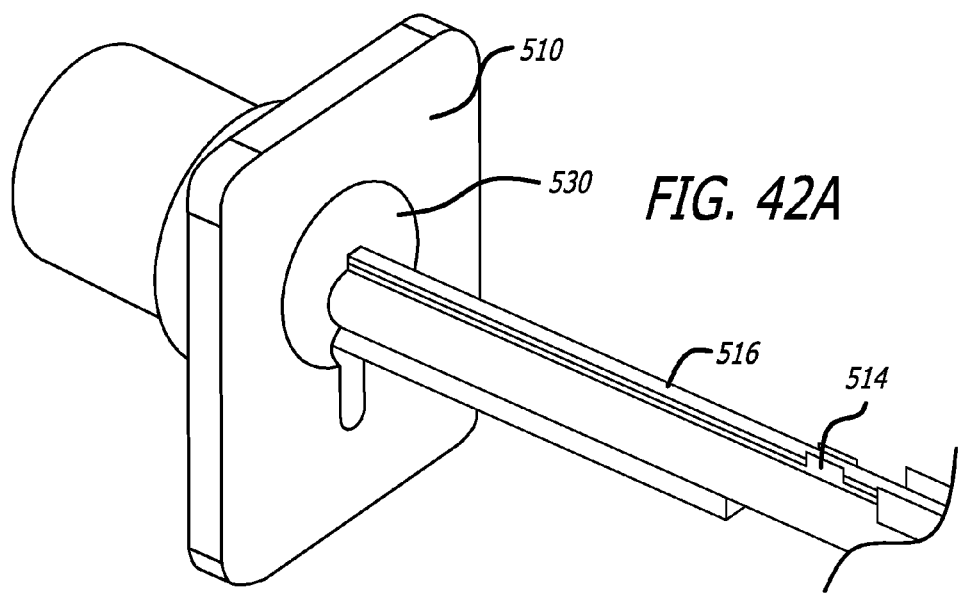
Figure 42B:
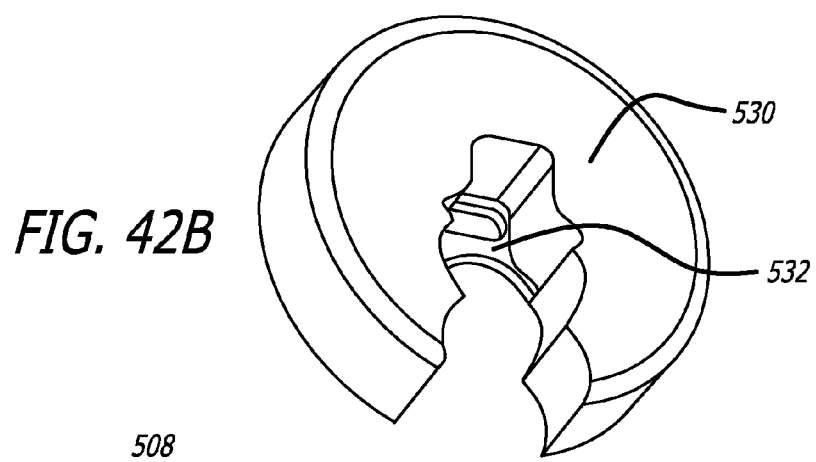

With reference to FIGS. 39-40, at a proximal end of the shaft assembly 124 is a sheath mount assembly 510 including a screw lock 512. Configured to extend through this structure are proximal portions of a cutter assembly 514 and a pusher assembly 516. Both the cutter and pusher assemblies include elongate portions extending toward a distal end 400 of the shaft assembly 124. The screw lock 512 of the sheath mount assembly 510 can be screwed to a terminal end of an introducer sheath assembly (not shown). The sheath mount 510 can include an elongate seal 519 (FIG. 40) which functions to seal and minimize fluid ingress into the handle portion of a delivery device. A proximal end of the seal 519 includes a lateral extension 521 which engages a proximal surface of the sheath mount to prevent the seal 519 from migrating distally and potentially jamming or stalling the cutter or pusher. In another approach (FIGS. 41-42B), a disc-like seal 530 is configured to be captured between the sheath mount 510 and case halves during assembly. The seal 530 restricts the flow of fluids (i.e., saline or irrigation solution) through the cutter/pusher area via a thin wiper feature. The seal 530 slightly compresses into the sheath mount 510 and is indexed over an outer profile of the shaft 124. The seal 530 stretches over the shaft and has a 0.010 inch thick wiper element 532 at the cutter/pusher interface to limit friction and reduce fluid flow.

Figure 43:
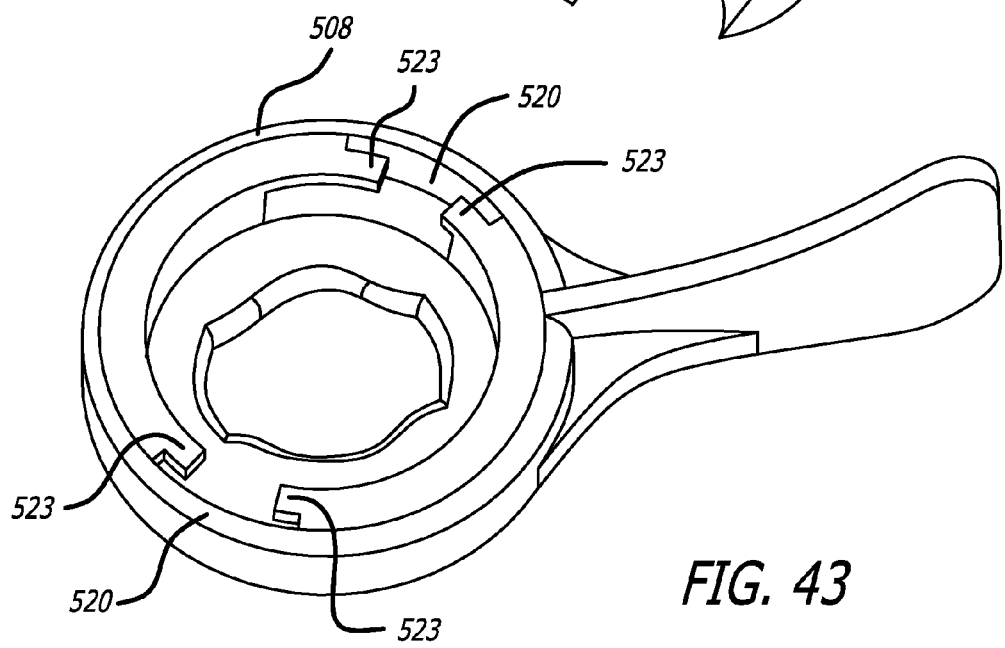
FIG. 43 is a perspective view, depicting structure defining a scope lock.

As shown in FIG. 43, the scope mount screw lock assembly 508 (See also FIGS. 1-5) includes a screw lock 520 for mating with the casing of the present device and a central opening for receiving a scope 549 which has a longitudinal dimension sufficient to extend longitudinally substantially a length of the scope tube 506. The central opening is shaped to lockingly receive the scope. The screw lock 520 includes two pairs of cantilevers 523 that form undersized gaps for tabs (not shown) formed on the device casing to press through. During use, the locks 520 remain engaged with the tabs due to the gaps therebetween being undersized. It is intended that the screw lock be configured so that the gap in the middle of the lock 520 places the weakest point of the lock in a position unlikely to be pulled on by the user or operator.

Figure 44:
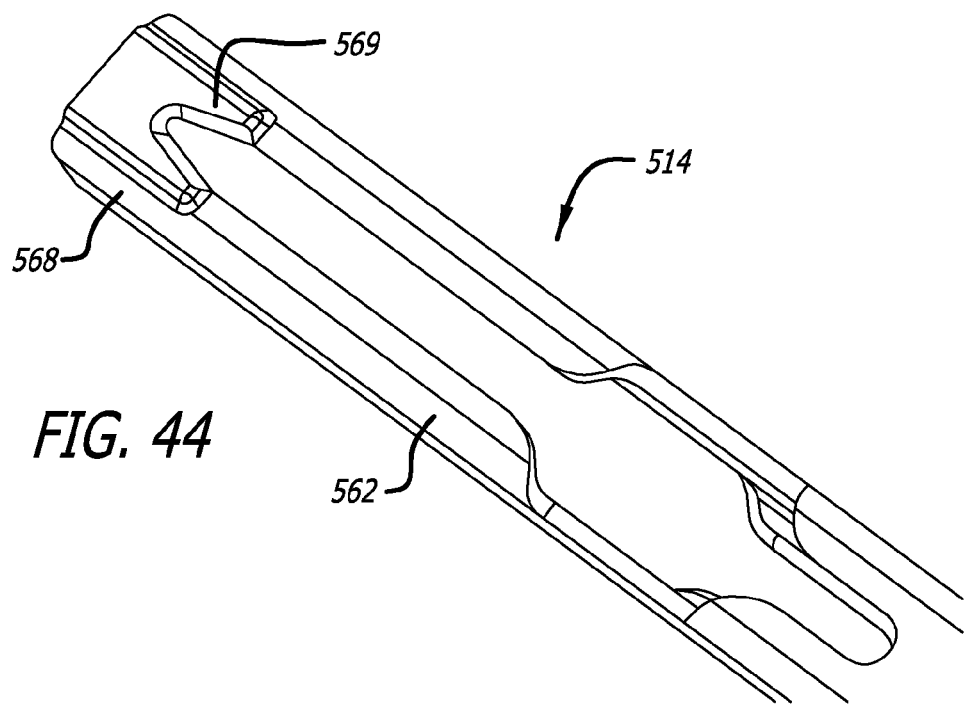
Figure 45:
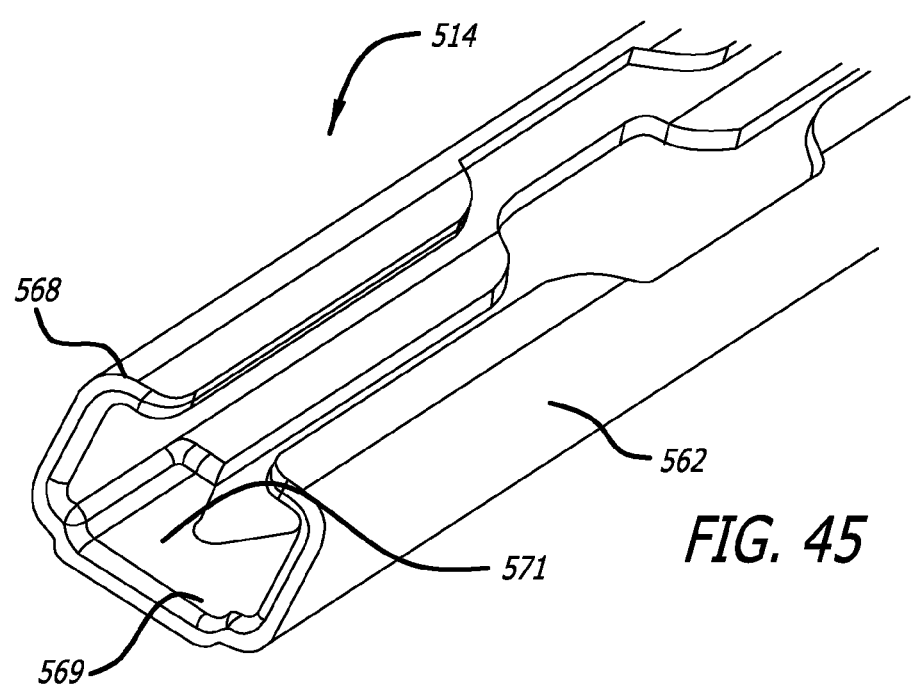

As best shown in FIGS. 44 and 45, an embodiment of the cutter assembly 514 includes elongate cutter tube 562. A distal end 568 of the cutter tube 562 is configured with a blade 569 so that once the cutter assembly 514 is withdrawn, the blade can sever as desired a connector of an anchor assembly. In one particular embodiment, the cutter 514 can be formed from ground 17-4PH stainless steel blank. Various structures are contemplated for incorporation into the cutter assembly to facilitate a clean severing of a connector as well as to aid in assembling a proximal component of an anchor assembly to the connector. For example, as best seen in FIG. 45, the cutter blade 569 includes a coined out underside that is intended to be offset from a bottom side of a proximal anchor by about 0.0035+0.0010 inches to cut a nominal 0.015 inch diameter connector. In this way, the proximal anchor can exit a cutter without deforming or compressing a suture or connector tag, and the strength of the connector to anchor connection is maintained.

As shown in FIGS. 46-48, the cutter 514 can define a generally rectangular elongate single body that can be formed by stamping and bending. An interior of the body is sized and shaped to receive a proximal anchor component 550. A proximal end portion of the cutter 564 can further include anti-buckling tabs 551 and extensions 553 intended to snap fit to a cutter block (described below). Lance-out structures 555 are also contemplated to be spaced along the cutter body which facilitate alignment of the cutter 514 within the shaft assembly.

Figure 50:
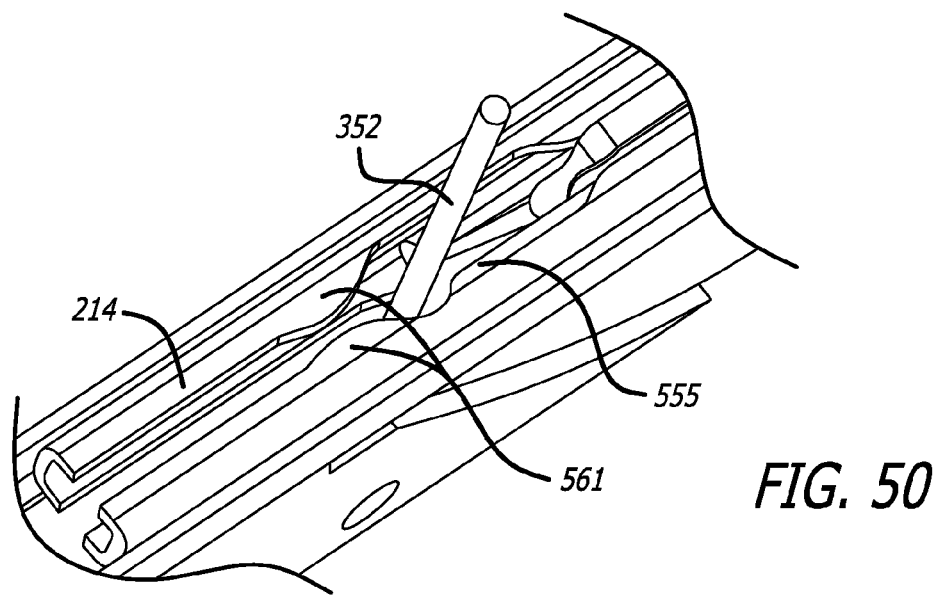

To eliminate snagging of a connector, walls defining a needle window 557 formed in the cutter 514 can be contoured to help properly guide the connector into a suture capture area 559. As best seen in FIG. 49, a proximal portion of the needle window 557 defines a gradual slope for directing the connector within the capture area 559. In a related approach (FIG. 50), bumps 561 can be formed on connector guiding structure to further aid in properly positioning a connector 352 for engagement with a proximal anchor component 555.

Figure 51:
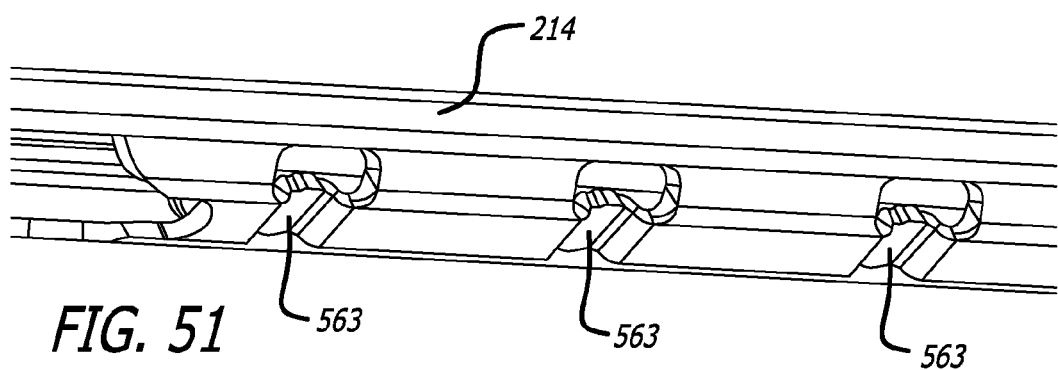
Figure 52:
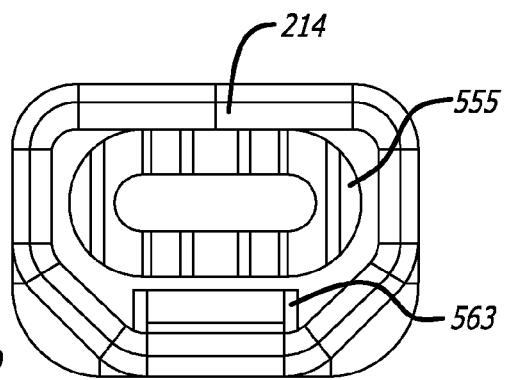

Moreover, as depicted in FIGS. 51 and 52, the cutter 214 can further include skew limiting projections 563 extending internally within the generally tubular cutter 214. As best seen in FIG. 52, the projections 563 help to maintain proper positioning of a proximal anchor component 555 within the cutter 214.

Figure 53:
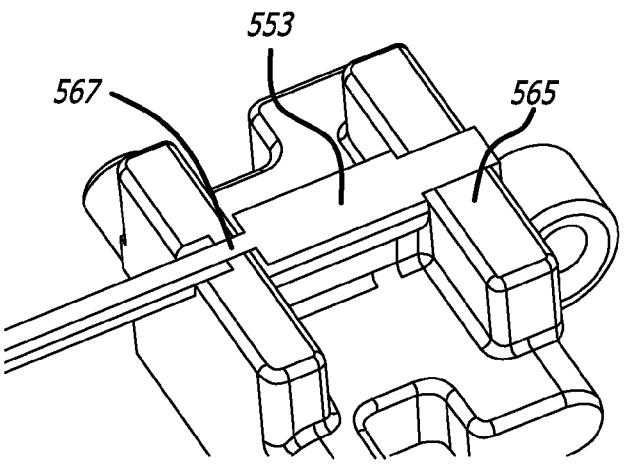
FIGS. 53-55 are perspective views, depicting proximal end connectors of the cutter assembly.
Figure 54:
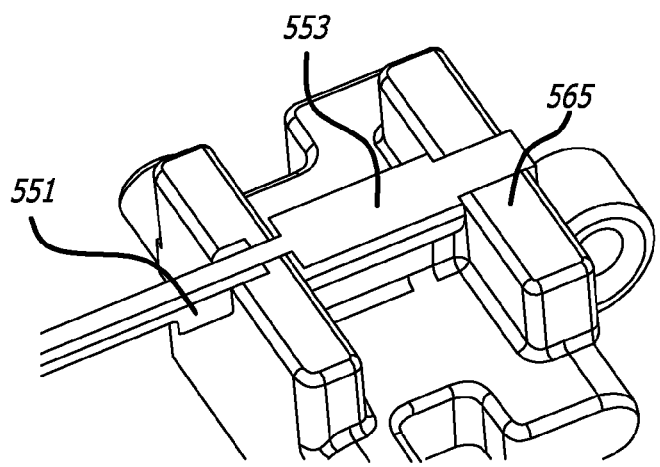
Figure 55:
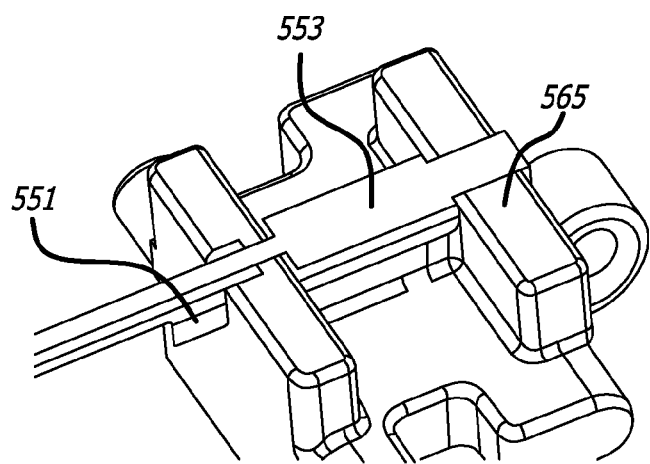
Figure 56:
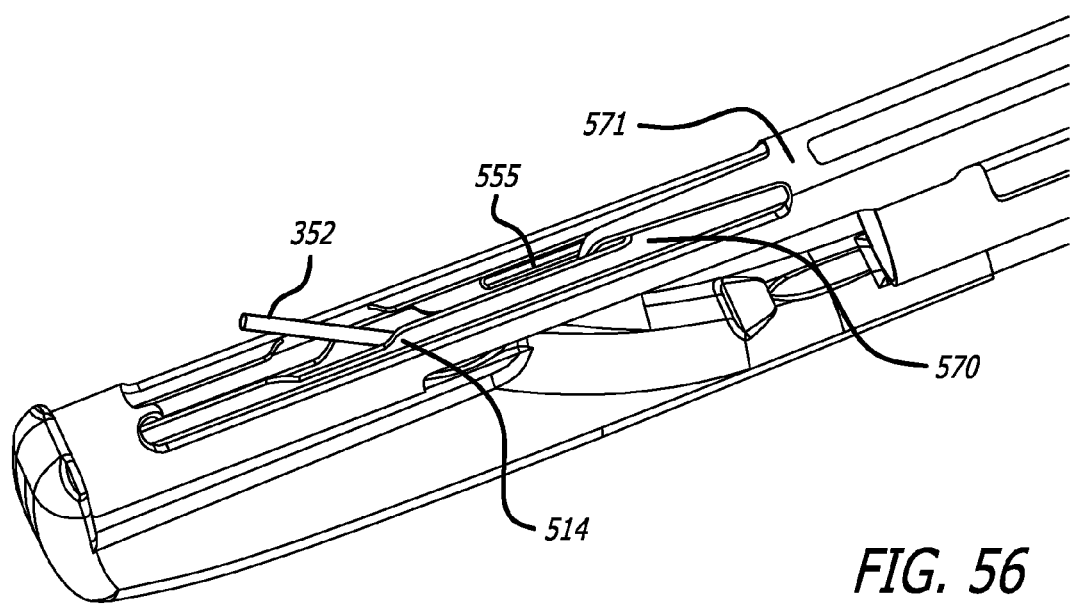
FIGS. 56-57 are perspective views, depicting features of a suture guide.
Figure 57:
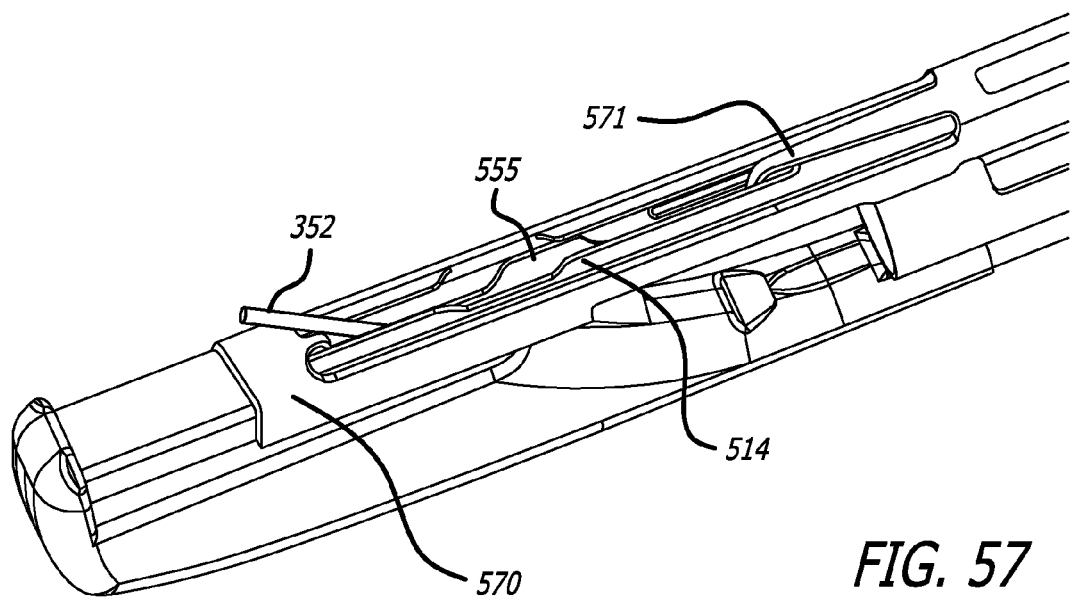
Figure 61:
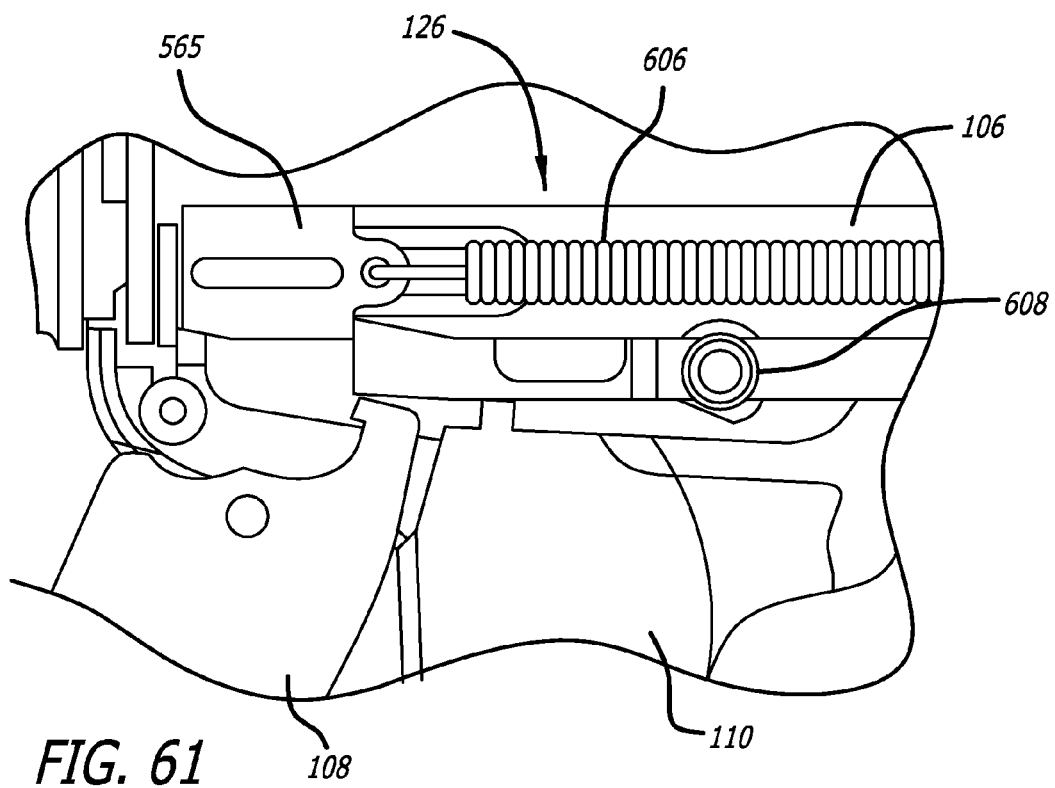
FIGS. 61-62 are partial cross-sectional views, depicting action of the lever permitting subsequent use of the cutter assembly as viewed from one side of the device.

Approaches to attaching the cutter 214 to a cutter block 565 are shown in FIGS. 53-55. As shown in FIG. 53, a point of potential buckling 567 of the cutter assembly can coincide with its connection to a cutter block 565. To offset such buckling, the anti-buckling tabs 551 can be configured adjacent a distal face of the cutter block 565 (FIG. 54). Such anti-buckling tabs 551 can alternatively or additionally be folded at a 30° angle to help index the cutter with respect to the cutter block 565. In each of these approaches, the extensions 553 snap fit to receiving structures of the cutter block 565.

In a further aspect, the present device can include a suture alignment slide 570 configured to slide under a cover 571 and over the cutter 514. The cover 571, in turn, includes a finger projector 573 which is sized and shaped to control and guide the movement of a proximal anchor 555. The alignment slide 570 indexes the connector 352 to a centerline of the cutter 514. It also operates to pull the connector 352 proximally for indexing within the proximal anchor component 555 to thus enhance connector capture by the anchor component 555. In other embodiments, a distal end of the needle housing itself can alternatively or additionally include a slot or notch for properly registering the connectors during device use and particularly when tension is being applied to the connector.

In order to accomplish the attachment of the proximal anchor 555 to the connector 352, a pusher assembly 575 is configured to extend within the cover 571 (See FIGS. 58-60). The pusher assembly 525 can include a proximal portion 577 which extends to the handle of the device (connected to pusher block as described below) and a distal portion 579 which attaches to the proximal portion 577. The distal portion 579 can further include an extension 581 sized to receive the length of a proximal anchor 555. The thickness of the extension 581 is chosen to ensure a 0.004 inch gap between a cutter and a bottom portion of the proximal anchor 555 so that a connector tag remains after its severing by the cutter. The cover 571 can further include an anchor stop 583 which is configured at a distal end of the cover 571. The anchor stop 583 is sized and shaped to protect the proximal anchor 555 from becoming trapped within the cover 571 after its engagement with the proximal anchor 555.

Figure 62:
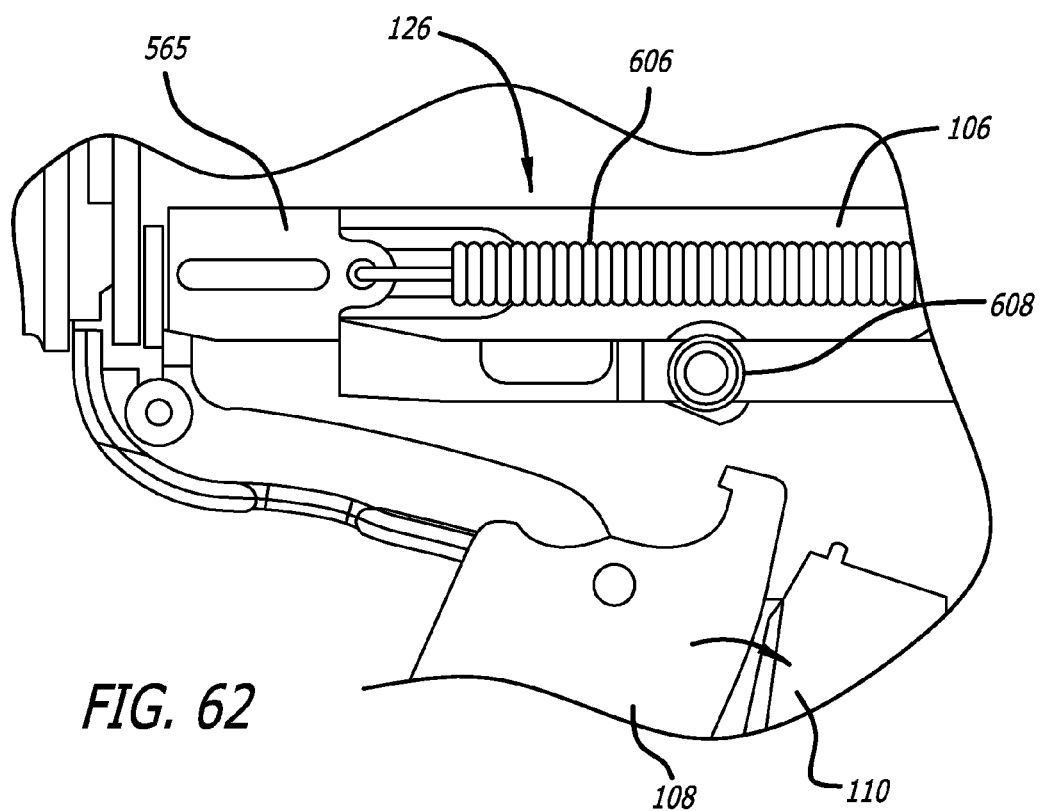

Details of an embodiment of the proximal anchor drive assembly 126 are depicted in FIGS. 61-67. The proximal anchor drive 126 includes the cutter block 565 operatively connected to a pusher block 604 by a spring 606. Longitudinal motion of each of the cutter and pusher blocks 565, 604 are guided by recesses formed in the casing 106 of the device. A cutter pawl 608 is further provided to control the timing of the action of the cutter and pusher blocks 565, 604. Initially, the operation of the proximal anchor drive 126 is locked out by the lever 110 (FIG. 61) as well as the proximal anchor actuator assembly 112. Upon depression of the lever 110 as described above in connection with the refraction of the needle, the lever 110 is moved such that its engagement with the cutter pawl 608 is removed (FIG. 62). It is in this condition that the proximal anchor drive 126 can be activated once the proximal anchor actuator assembly 112 is unlocked.

Figure 63:
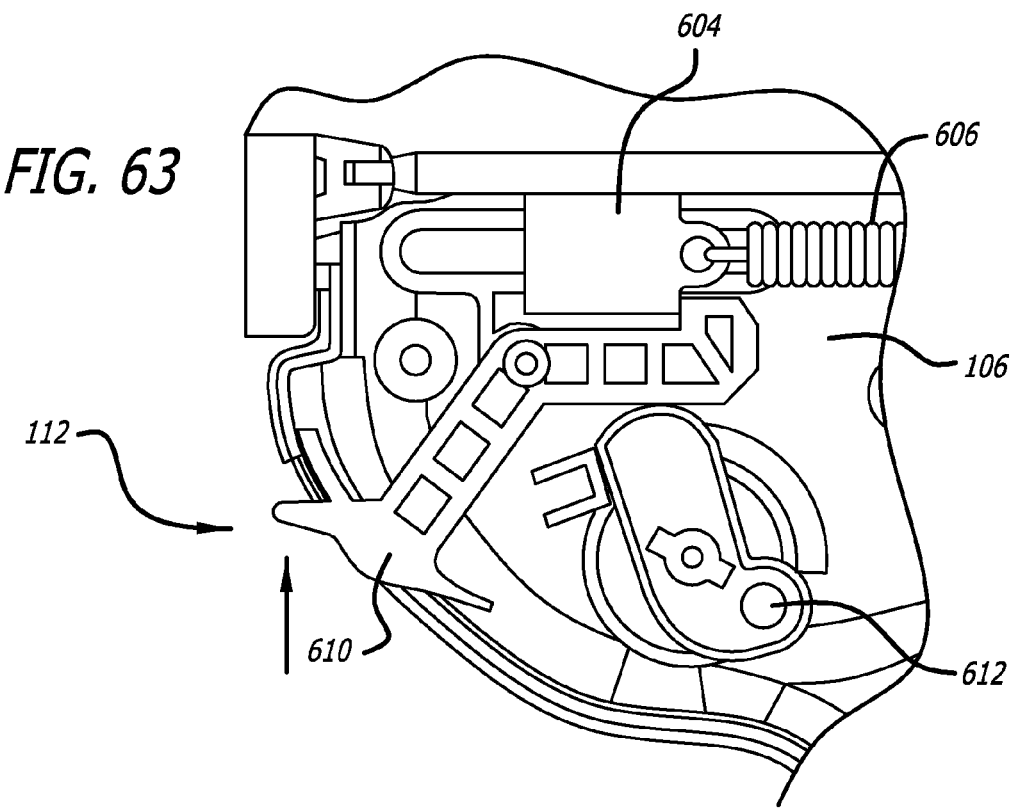
FIGS. 63-64 are partial cross-sectional views, depicting action of internal components of an interlock assembly of the proximal anchor actuator as viewed from the opposite side relative to FIGS. 61-62.
Figure 64:
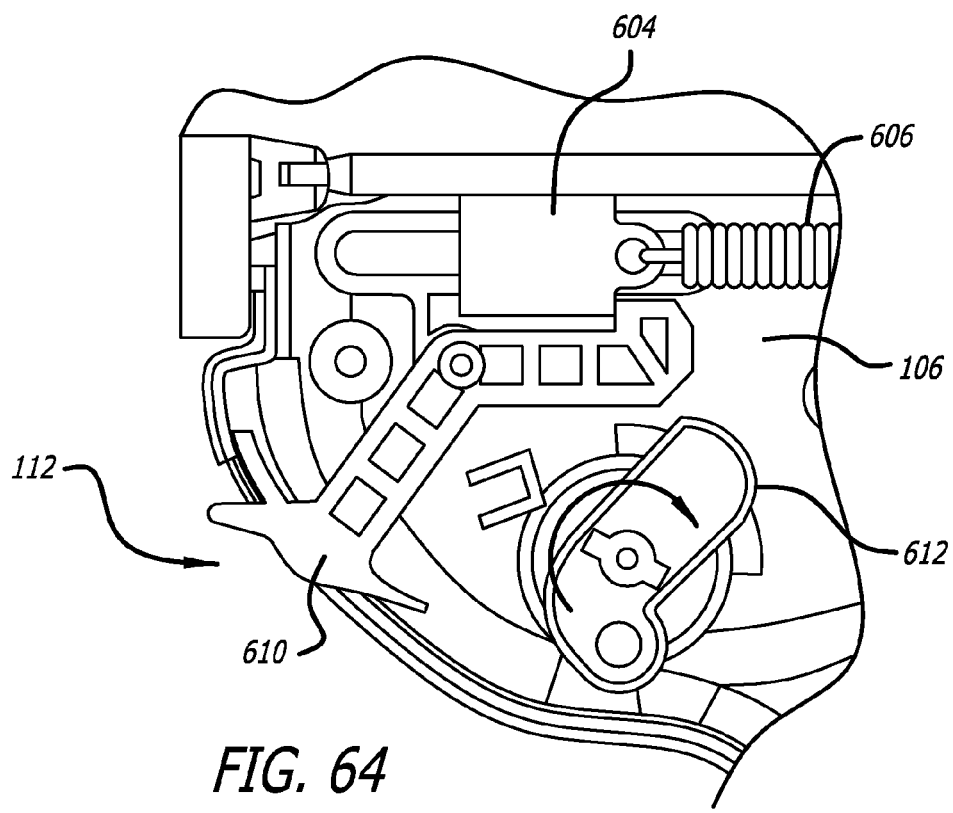
Figure 65:
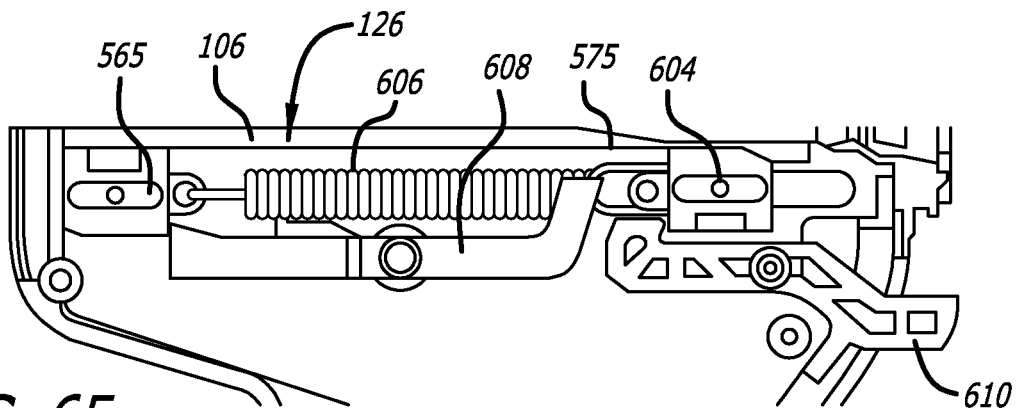
FIGS. 65-67 are partial cross-sectional views, depicting action of interval components upon activation of the proximal anchor actuator as viewed from same side as FIGS. 61-62.
Figure 66:
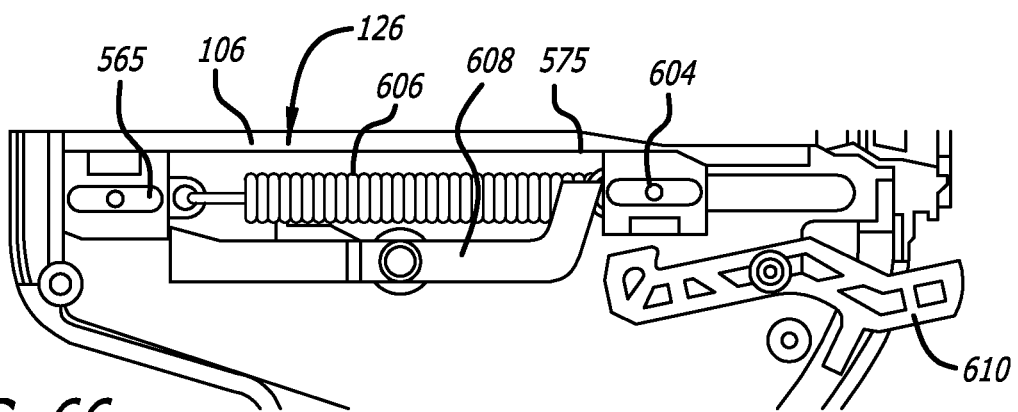
Figure 67:
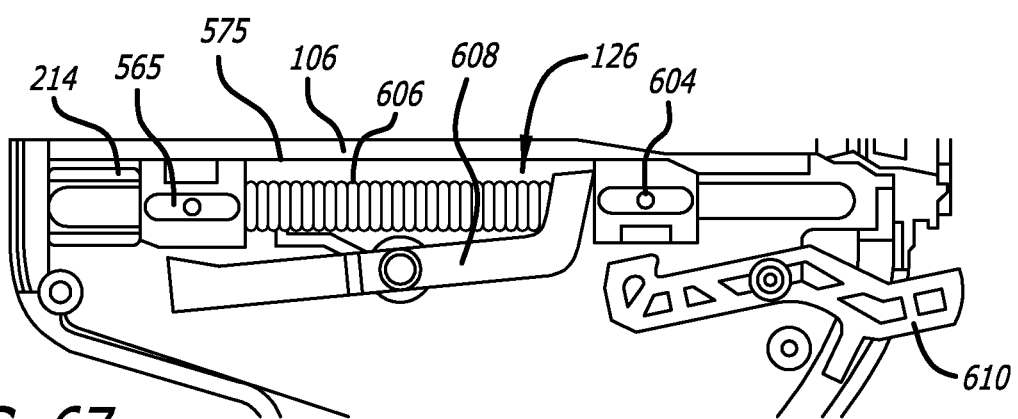

The proximal anchor actuator assembly 112 is configured at a back end of the casing 106 and includes a pusher pawl 610 and a pusher pawl interlock 612 (See FIGS. 63 and 64). The pusher pawl interlock 612 can be unlocked by the retraction lever 110 away from engagement with the pusher pawl 610 to thereby unlock the proximal anchor drive 126. Next, the pusher pawl 610 can be rotated by the operator to activate the proximal anchor drive 126 (See FIGS. 65 and 66). By so rotating the pusher pawl 610, the pusher block 604 is released and the spring 606 causes the pusher block 604 to slide forwardly. Through its connection to the pusher of the pusher block 604, the pusher assembly 575 is advanced distally which, in turn, results in the proximal anchor component 555 engaging the connector 352 (See also FIG. 60).

Next, the pusher block 604 contacts a first end of the cutter pawl 608 causing its second end to rotate away from the engagement with the cutter block 565. It is to be noted that the timing of first advancing a proximal anchor component 555 and then cutting a connector 352 to length can be controlled by the force applied by the spring 606, the distance the pusher block 604 is to travel, and/or the location of the first end of the cutter pawl 608. A proximal end of the cutter 214 is attached to the cutter block 565. As the cutter block 565 moves proximally, the cutter 214 is withdrawn.

Figure 68:
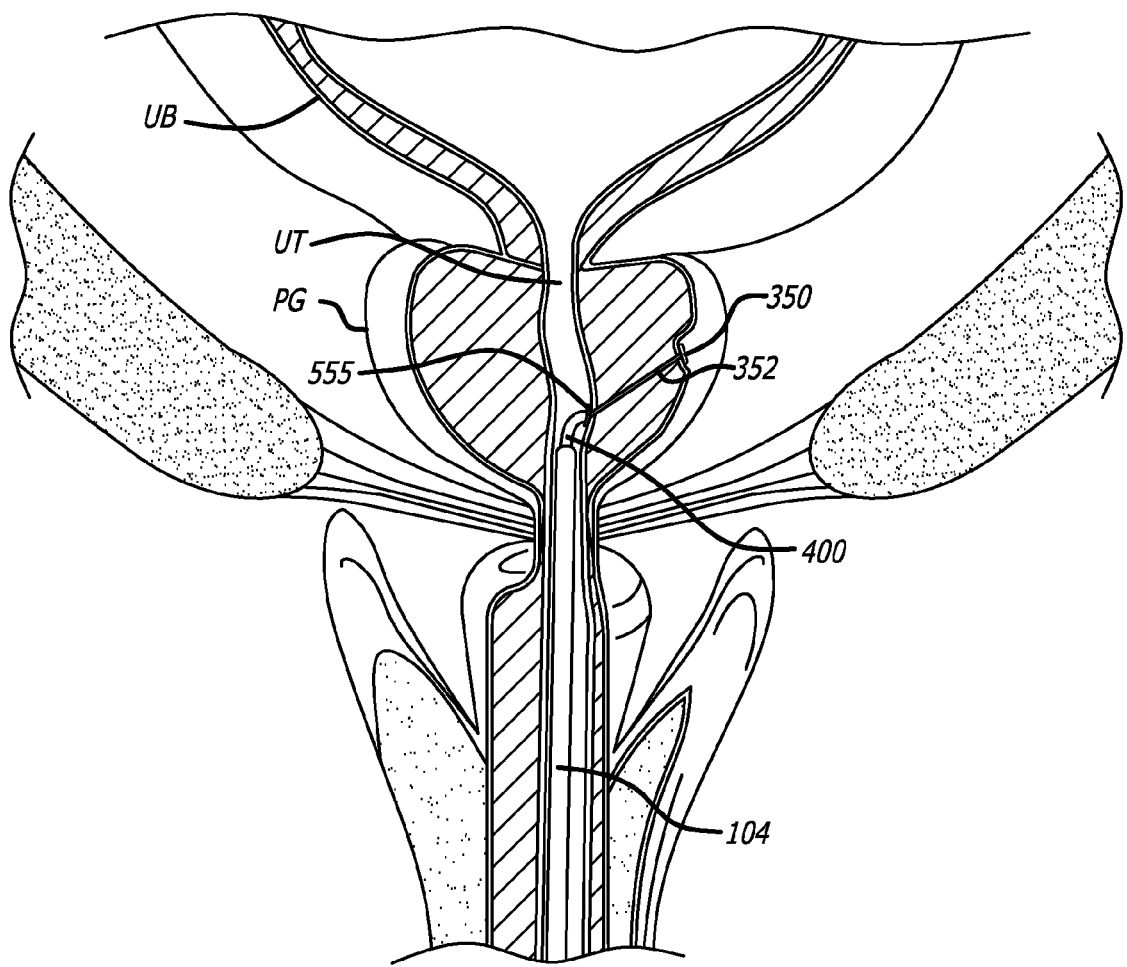
FIG. 68 is a cross-sectional view, depicting release of a second anchor component within an interventional site.
Figure 69:
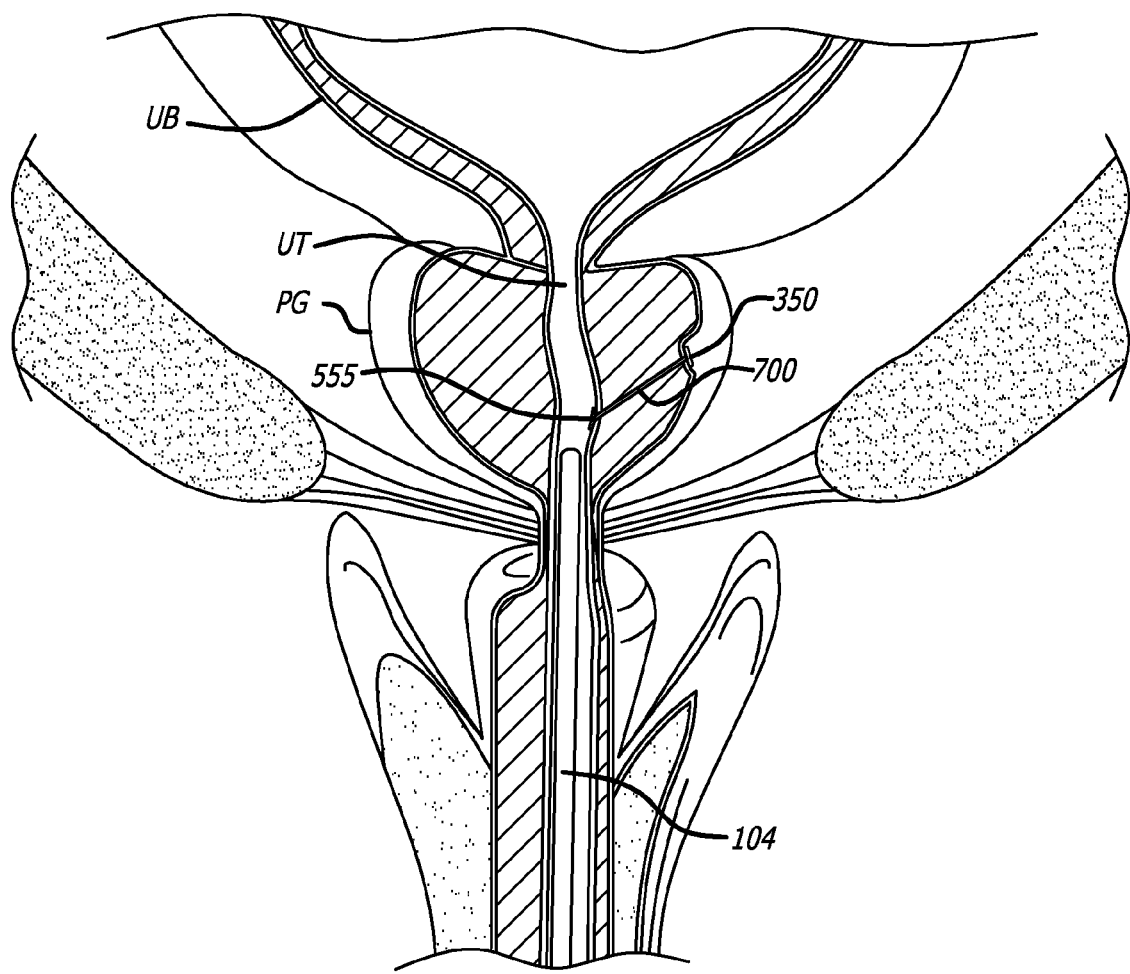
FIG. 69 is a cross-sectional view, depicting release of an assembled anchor assembly within an interventional site.
Figure 70:
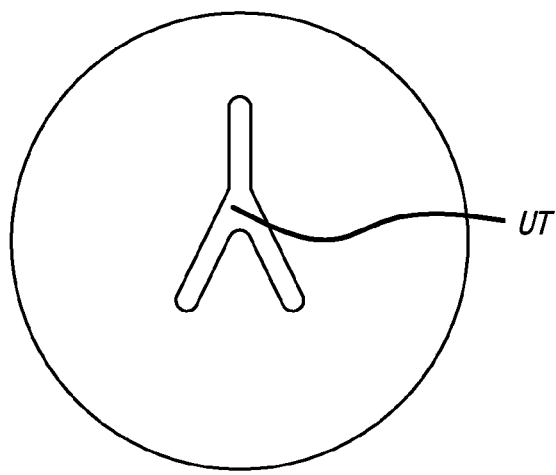
FIG. 70 is a cross-sectional view looking along the axis of the urethra within an enlarged prostate, depicting an untreated interventional site.
Figure 71:
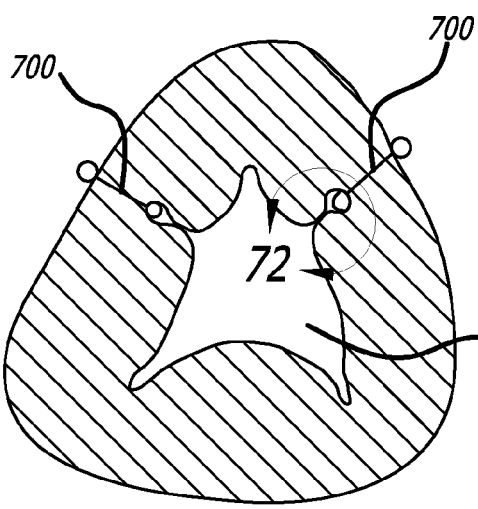
FIG. 71 is a cross-sectional view looking along the axis of the urethra within an enlarged prostate, depicting implantation of two anchor assemblies at an interventional site.
Figure 72:
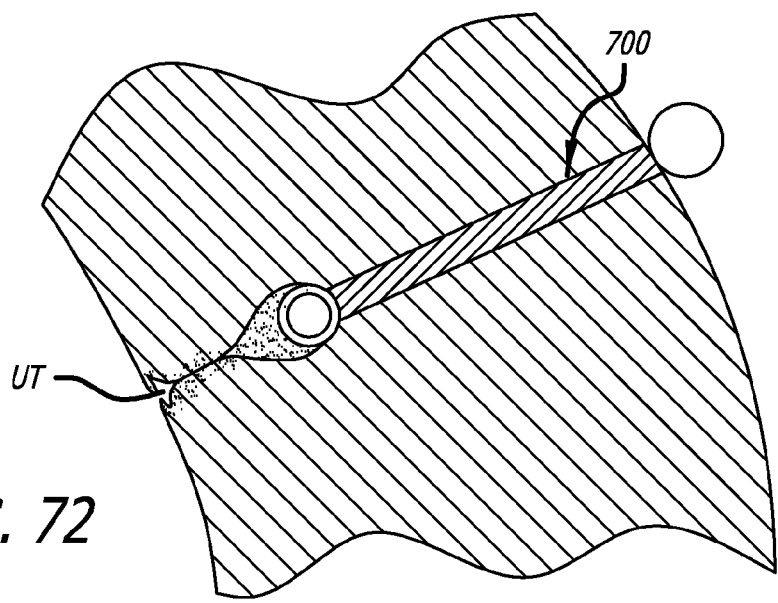
FIG. 72 is an enlarged view of a portion of FIG. 71.

Accordingly, release of the pusher assembly advances the second component 555 of an anchor assembly into locking engagement with a connector of an anchor assembly (See FIG. 60). Such action causes the pusher 575 to advance the anchor component 555 onto a connector (e.g., a suture) while the connector is being held by the tool with sufficient force and the anchor is advanced with sufficient speed and force to seat the anchor 555 with reliable retention force. Within a patient's body, as shown in FIG. 68, the anchor assembly is configured across anatomy within the interventional site. Upon withdrawal of the cutter assembly, the blade portion thereof is brought across the connector 352 thereby severing it close to the second anchor component 555 leaving a short tag. The resultant implanted anchor assembly 700 is shown in FIGS. 69, 71 and 72. FIG. 71 depicts a partial cross-sectional view of the urethra (UT) widened due to the anchor assembly compressing the surrounding enlarged prostate tissue due to the fact that the outer capsular tissue is rather strong, substantially non-compressible and non-displaceable while the adenoma of the prostate gland is compressible and the urethral wall displaceable. By way of comparison, FIG. 70 depicts a partial cross-sectional view of an untreated interventional site of the urethra (UT) narrowed by the surrounding enlarged prostate tissue.

The second anchor component can be embodied in a slotted anchor configured to secure to a connector. The slotted proximal anchor can include a flattened-tubular back end that resembles a flattened tube in shape, with a width in lateral cross-section that is greater than its thickness. The slotted proximal anchor also includes a pair of spaced apart prongs extending from the back end of the slotted proximal anchor to the front end of the slotted proximal anchor. The spaced prongs join together at a slot inception. The prongs are shaped and sized of a configuration and of a rigidity to substantially prevent deflection of the prongs. The prongs can include inwardly facing protrusions that are configured to capture and deform the connector between the protrusions and prevent the connector from disengaging from the slotted anchor device once engaged. The mechanism of suture attachment and strength of the assembly is a combination of compression of the suture between the stiff slotted prongs of the anchor as well as disruption of the suture surface by the discreet edges of the slotted, flattened-tubular anchor. The discreet edges provide a lower contact surface area between anchor prongs and suture and focuses the compressive forces in focal points that cause the suture to conform around both internal recesses and external faces. It is also to be recognized that various further embodiments of slotted anchors or anchors forming a clip are also contemplated. In particular, various embodiments of structures which accordingly provide alternative approaches to attach to a connector can be employed. That is, the anchors can be deformable, deflectable, latching, nested, meltable and/or coiled in structure.

Accordingly, the present invention contemplates both pushing directly on anchor portions of an anchor assembly as well as pushing directly upon the connector of the anchor assembly. Moreover, as presented above, the distal or first anchor component is advanced and deployed through a needle assembly and at least one component of the proximal or second anchor component is advanced and deployed from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly 700 is configured so that the assembly invaginates within target tissue, such as within natural folds formed in the urethra by the opening of the urethra lumen by the anchor assembly (See FIGS. 71-72). In fact, in situations where the anchor assembly is properly placed, wispy or pillowy tissue in the area collapses around the anchor structure. Eventually, the natural tissue can grow over the anchor assembly 700 and new cell growth occurs over time (see FIG. 69). Such cooperation with target tissue facilitates healing and avoids unwanted side effects such as calcification or infection at the interventional site.

Subsequent to the interventional procedure, the patient can be directed to take alpha blockers for 2-4 weeks. Anti-inflammatory medicine can also be taken.

A multi-centre single-arm, prospective, non-randomized study in the context of improving LUTS for the purpose of improving sexual function was performed to evaluate the feasibility and safety of the anchor implantation procedure. Patients were treated by a single urologist who has received in-service training for the procedure prior to the commencement of the study.

Male subjects were enrolled in this study if they met the following inclusion criteria: 1) diagnosis of lateral lobe symptomatic BPH., 2) >54 years, 3) IPSS Symptom score>13, 4) peak urine flow rate (Qmax)>5 ml/sec-<12 ml/sec on a voided volume>125 ml., 5) prostate volume≥20 gm, ≤100 gm, 6)

anesthesia risk group ASA class I-III, 7) normal microscopic urinalysis and 8) a stable PSA over previous two years, or had a pre-treatment transrectal ultrasound and prostate tissue biopsy, if clinically indicated in the opinion of the investigator. If a prostate tissue biopsy had been performed within 6 months of the treatment date, then a further biopsy was not required.

The exclusion criteria included:

a. Mental capacity, dementia or inability to give informed consent.

b. Subject in retention, or with previous history of urinary retention.

c. Post void residual volume>250 ml by transabdominal ultrasound.

d. Prostate gland with obstructive median lobe or prominent bladder neck requiring intervention.

e. History of illness/symptoms or surgery that may confound results of study, or pose additional risk to subject.

f. Patient with a life expectancy of less than 2 years.

g. Previous prostate surgery, dilatation, stent, laser, hyperthermia (i.e. non-pharmaceutical prostate treatment).

h. PSA>10 ng/ml.

i. Known, or suspected urological conditions which may effect voiding function such as confirmed or suspected malignancy of the bladder or prostate, previous pelvic irradiation or radical pelvic surgery, neurogenic bladder and/or sphincter abnormalities, cystolithiasis or haematuria within 3 months, urinary tract infection, urethral strictures, bladder neck contracture, active clinical prostatitis, bladder pathologies or diabetes mellitus affecting bladder function.

j. Compromised renal function (serum creatinine>1.58 mg/l or 0.1 mmol/L) (ref: medcalc version 5.3 palm/os.) (medcalc.med-ia.net)

k. Previous rectal surgery, other than hemorrhoidectomy, that could have distorted the pelvic anatomy, or any implants in the pelvic/femoral region.

l. Subject interested in future fertility.

m. Concomitant medications: including β-blockers, antihistaminics, anticonvulsants, and antispasmodics within 1 week of treatment unless there is documented evidence that the subject has been on the same drug dose for at least 6 months with a stable voiding pattern (the drug dose should not be altered or discontinued for entrance into or throughout the study).

n. Anti-coagulant medication other than ASA or clopidogrel. ASA and clopidogrel must be ceased 7 days prior to the procedure.

o. 5-α-reductase inhibitors within 6 months of pre treatment evaluation unless there was documented evidence that the subject has been on the same drug dose for at least 6 months with a stable voiding pattern (the drug dose should not be altered or discontinued for entrance into or throughout the study).

p. Antidepressants, anticholinergics, or α-blockers within 1 week of the pretreatment evaluation.

q. Anti-androgens or GnRH analogs within 2 months of pretreatment evaluation.

r. Any abnormal coagulopathy.

s. Evidence of current UTI.

t. Evidence of current infectious process.

Erectile function was assessed by the 5 question version of the International Index of Erectile Function (IIEF-5, or SHIM-5). Ejaculation function was assessed by the Male Sexual Health Questionnaire (MSHQ). An initial post-operative assessment was completed before hospital discharge or within 48 hours. Patient follow-up visits were scheduled at 2 weeks, 6 weeks, 3 months, and 6 months post treatment.

Figure 74:
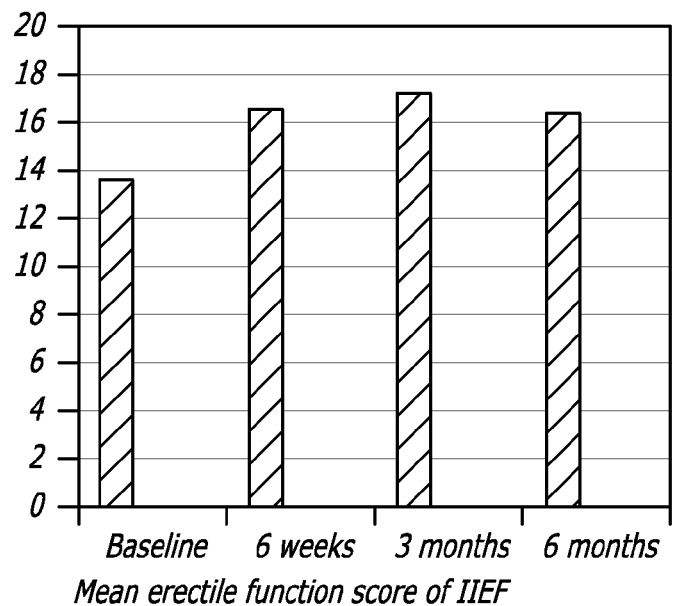
FIGS. 74-76 are graphical representations, depicting results of a sexual dysfunction treatment.
Figure 75:
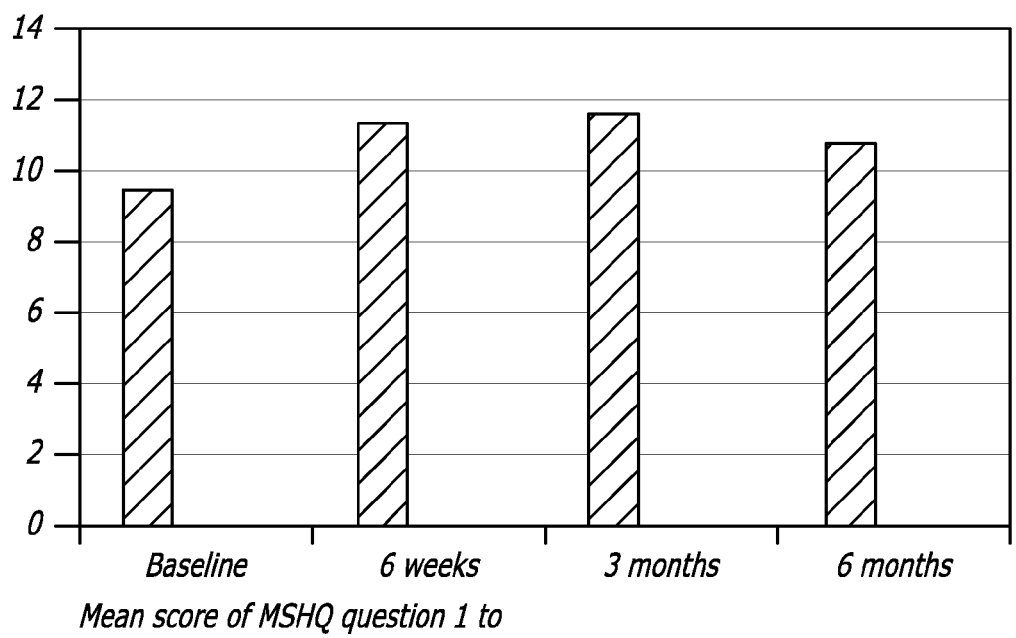
Figure 76:
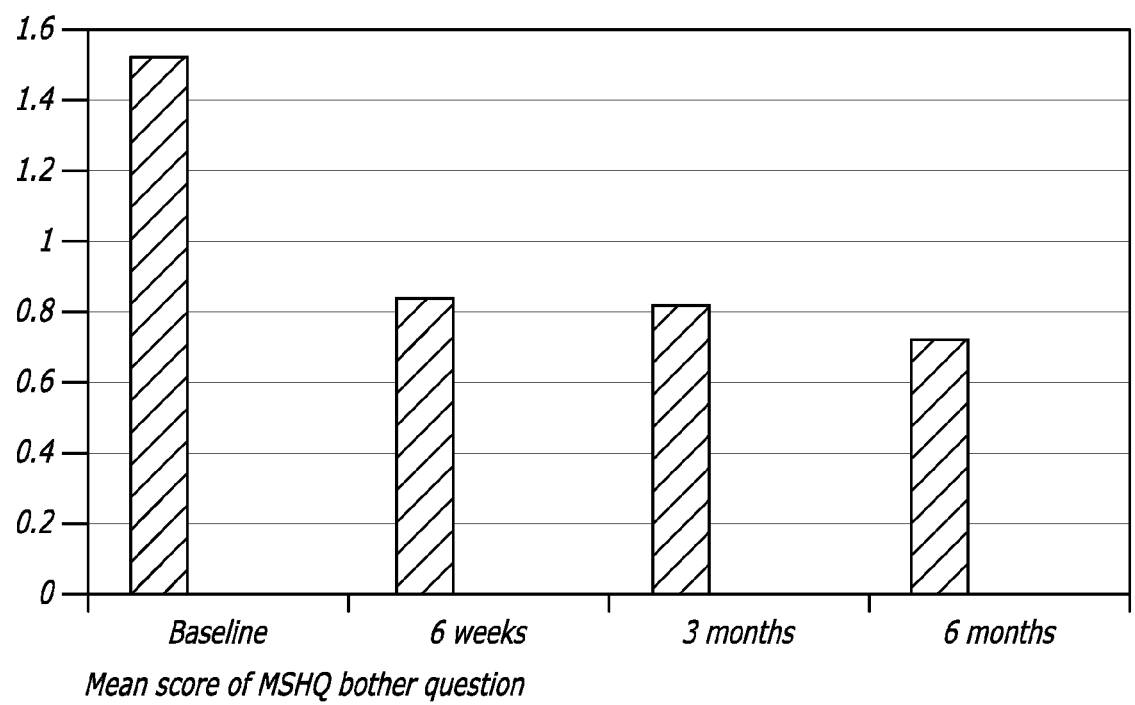

Results of the multi-center single-arm, prospective, non-randomized study are shown in FIGS. 74-76. The mean baseline score for the erectile questions of the IIEF was 13.76 demonstrating moderate to severe ED. At 6 weeks, 3 months, and 6 months the mean scores were 16.67, 17.46, and 16.50 respectively (p<0.05). The mean baseline score for the MHSQ questions 1-3 was 9.48. At 6 weeks, 3 months, and 6 months the mean scores were 11.63, 11.83, and 11.05 (respectively) (p<0.05). The mean score for the MSHQ question pertaining to bother was 1.52. At 6 weeks, 3 months, and 6 months the mean scores were 0.85, 0.83, and 0.74 (respectively) (p<0.05). Accordingly, improvements in sexual function were exhibited as a result of the presently disclosed anchor implantation procedure.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Figure 73:
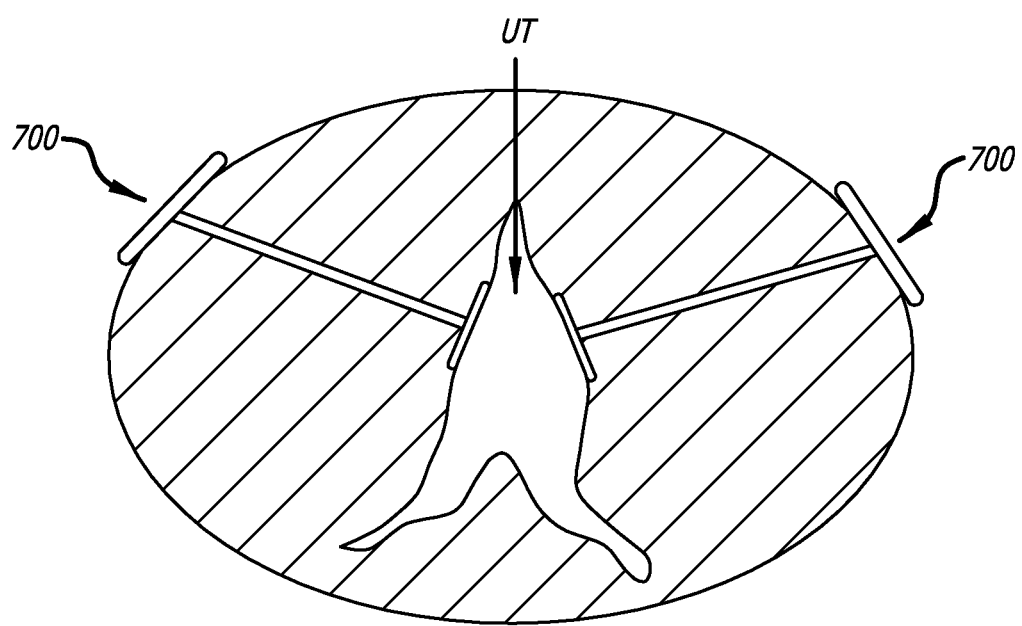
FIG. 73 is a cross-sectional view, depicting another view of two anchor assemblies implanted at an interventional site.

It has been observed that placing the anchors at various desired positions within anatomy can extract the best results. For example, when treating a prostate, one portion of an anchor assembly can be placed within an urethra and a second component beyond the outer surface of the prostate. It has been found that implanting the anchor assemblies by using the distal end of the device to displace the prostate lobe on either side (while the tension spring is taking up slack in the connector after the delivery needle has been refracted) while deploying the second anchor component so that the ten o'clock and two o'clock positions (when looking along the axis of the urethra) are supported or retained, effectively holds the anatomy open and also facilitates invagination of the anchor portion within natural tissue. Typically, one to two pairs of anchor assemblies are implanted to create an anterior channel along the urethra within the prostate gland (See FIG. 73). This is particularly true in the regions of anatomy near the bladder and the juncture at which the ejaculatory duct connects to the urethra.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector 95 can for example, be coated with a polymer matrix or gel coating which retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is to be recognized that the timing of the dual advancement of the needle and connector assemblies and subsequent relative motion between the assemblies is coordinated. That is, the needle assembly first provides access to an interventional site and then the connector assembly is left extending beyond a terminal end of the needle assembly through the relative motion of the needle and connector assemblies.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors which can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism which pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A method of treating sexual dysfunction, comprising:
accessing anatomy involved in male sexual function;
providing a delivery device housing an anchor assembly;
identifying tissue to be manipulated for treating sexual dysfunction;
implanting the anchor assembly to manipulate tissue for treating sexual dysfunction; and
assessing erectile function prior and subsequent to implantation of the anchor assembly.

2. The method of claim 1, further comprising manipulating tissue to treat benign prostatic hyperplasia.

3. The method of claim 1, further comprising manipulating tissue to improve lower urinary tract symptoms.

4. The method of claim 1, further comprising arranging the anchor assembly to treat bladder outlet obstruction.

5. The method of claim 1, further comprising assessing nitric oxide levels in one or more of a prostate, a bladder and an urethra prior and subsequent to implantation of the anchor assembly.

6. The method of claim 1, further comprising assessing Rho-Kinase levels prior and subsequent to implantation of the anchor assembly.

7. The method of claim 1, further comprising implanting a plurality of anchor assemblies.

8. A method of treating sexual dysfunction, comprising:
accessing anatomy involved in male sexual function;
providing a delivery device housing an anchor assembly;
identifying tissue to be manipulated for treating sexual dysfunction;
implanting the anchor assembly to manipulate tissue for treating sexual dysfunction; and
assessing ejaculation function prior and subsequent to implantation of the anchor assembly.

9. The method of claim 8, further comprising manipulating tissue to treat benign prostatic hyperplasia.

10. The method of claim 8, further comprising manipulating tissue to improve lower urinary tract symptoms.

11. The method of claim 8, further comprising arranging the anchor assembly to treat bladder outlet obstruction.

12. The method of claim 8, further comprising implanting a plurality of anchor assemblies.

\* \* \* \* \*